US012663419B2

(12) United States Patent
Kralicek et al.

(10) Patent No.: US 12,663,419 B2
(45) Date of Patent: Jun. 23, 2026

(54) BIOSENSOR DEVICE AND METHODS

(71) Applicant: SCENTIAN BIO LIMITED, Auckland (NZ)

(72) Inventors: Andrew Vladimir Kralicek, Auckland (NZ); Colm Carraher, Auckland (NZ); Nihan Aydemir, Auckland (NZ); Jadranka Travas-Sejdic, Auckland (NZ); Roshan Khadka, Auckland (NZ); Natalie Olivia Victoria Plank, Wellington (NZ); Thanihaichelvan Murugathas, Jaffna (LK)

(73) Assignee: SCENTIAN BIO LIMITED, Auckland (NZ)

( * ) Notice: Subject to any disclaimer, the term of this patent is extended or adjusted under 35 U.S.C. 154(b) by 852 days.

(21) Appl. No.: 17/251,137

(22) PCT Filed: Jun. 13, 2019

(86) PCT No.: PCT/IB2019/054932
    § 371 (c)(1),
    (2) Date: Dec. 10, 2020

(87) PCT Pub. No.: WO2019/239360
    PCT Pub. Date: Dec. 19, 2019

(65) Prior Publication Data
    US 2021/0255184 A1    Aug. 19, 2021

(30) Foreign Application Priority Data
    Jun. 13, 2018    (NZ) ........................................ 743418

(51) Int. Cl.
    *G01N 33/566*    (2006.01)
    *G01N 21/552*    (2014.01)
    (Continued)

(52) U.S. Cl.
    CPC ......... *G01N 33/566* (2013.01); *G01N 21/554* (2013.01); *G01N 27/4145* (2013.01);
    (Continued)

(58) Field of Classification Search
    CPC ............. G01N 33/566; G01N 33/5432; G01N 33/5438; G01N 33/6872; G01N 21/554;
    (Continued)

(56) References Cited

U.S. PATENT DOCUMENTS

| 6,024,924 A | 2/2000 | Schoning et al. |
| 6,204,263 B1 | 3/2001 | Lu et al. |

(Continued)

FOREIGN PATENT DOCUMENTS

| CA | 2616144 A1 | 3/2009 |
| CN | 104650220 | 5/2015 |

(Continued)

OTHER PUBLICATIONS

Fujii et al., English translation of JP-2018059786-A, 2018 (Year: 2018).*

(Continued)

*Primary Examiner* — Shizhi Qian

(74) *Attorney, Agent, or Firm* — LEYDIG, VOIT & MAYER, LTD.

(57) ABSTRACT

A sensor device comprising an insect odorant receptor complex, comprising an OrX and an Orco, in electrical communication with a substrate, wherein the sensor device is configured to detect a change in an electrical characteristic of the substrate; a sensor device component comprising an insect odorant receptor complex, comprising an OrX and an Orco, in electrical communication with a substrate; methods for manufacture and use of the sensor device and sensor device component; and methods of use of the sensor to detect an analyte.

11 Claims, 24 Drawing Sheets

(51) Int. Cl.
  *G01N 27/414* (2006.01)
  *G01N 33/543* (2006.01)
  *G01N 33/68* (2006.01)
(52) U.S. Cl.
  CPC ..... *G01N 33/5432* (2013.01); *G01N 33/5438*
    (2013.01); *G01N 33/6872* (2013.01); *G01N*
    *27/414* (2013.01); *G01N 2333/43573*
    (2013.01)
(58) Field of Classification Search
  CPC ............. G01N 27/4145; G01N 27/414; G01N
    27/026; G01N 2333/43573; G01N
    2291/0426; G01N 2291/0255; G01N
    2291/0256; G01N 2291/025; G01N
    29/022; B82Y 15/00; B82Y 40/00; C07K
    2319/21; C07K 14/43581; C07K
    14/43563; C07K 14/705
  See application file for complete search history.

(56) References Cited

U.S. PATENT DOCUMENTS

| | | | |
|---|---|---|---|
| 8,152,992 B2 | 4/2012 | Smela et al. | |
| 2006/0172279 A1 | 8/2006 | Smela et al. | |
| 2007/0054266 A1 | 3/2007 | Sato et al. | |
| 2011/0059544 A1 | 3/2011 | Hong et al. | |
| 2012/0028820 A1 | 2/2012 | Rhodes et al. | |
| 2013/0018599 A1* | 1/2013 | Peng .................... | H01L 29/778 |
| | | | 977/734 |
| 2013/0324522 A1 | 12/2013 | Vosshall et al. | |
| 2015/0065363 A1 | 3/2015 | Johnson, Jr. et al. | |
| 2017/0299602 A1 | 10/2017 | Johnson, Jr. et al. | |
| 2017/0355769 A1 | 12/2017 | Benatuil et al. | |
| 2019/0225659 A1* | 7/2019 | Takahashi .............. | C12N 15/85 |
| 2019/0346401 A1 | 11/2019 | Kralicek et al. | |

FOREIGN PATENT DOCUMENTS

| | | | | |
|---|---|---|---|---|
| CN | 108051489 A | 5/2018 | | |
| EP | 2848929 A1 * | 3/2015 | ......... | G01N 27/4145 |
| JP | H11-511564 A | 10/1999 | | |
| JP | 2012191904 A | 10/2012 | | |
| JP | 5854686 | 2/2013 | | |
| JP | 2018/059786 | 4/2018 | | |
| JP | 2018059786 A * | 4/2018 | | |
| KR | 100616608 | 2/2005 | | |
| KR | 101493065 | 1/2015 | | |
| WO | WO 2000/043410 A2 | 7/2000 | | |
| WO | WO 2000/050566 A2 | 8/2000 | | |
| WO | WO 2002/068593 A2 | 9/2002 | | |
| WO | WO 2002/077200 A2 | 10/2002 | | |
| WO | WO 2005/062780 A2 | 7/2005 | | |
| WO | WO 2009/136742 A1 | 11/2009 | | |
| WO | WO 2012/050646 A2 | 4/2012 | | |
| WO | WO 2012/154403 A2 | 11/2012 | | |
| WO | WO 2013155553 | 10/2013 | | |
| WO | WO 2014064443 | 5/2014 | | |
| WO | WO 2016031080 | 3/2016 | | |
| WO | WO 2017/122338 A1 | 7/2017 | | |
| WO | WO 2018/116186 A1 | 6/2018 | | |

OTHER PUBLICATIONS

Son et al., Bioelectronic nose using odorant binding protein-derived peptide and carbon nanotube field-effect transistor for the assessment of *Salmonella* contamination in food, Anal. Chem., 2016, 88, 11283-11287 (Year: 2016).*
Son et al., The bioelectronic nose and tongue using olfactory and taste receptors: Analytical tools for food quality and safety assessment, Biotechnology Advances, 2018, 36(2), 371-379 (Year: 2018).*
Dung et al., Applications and advances in bioelectronic noses for odour sensing, Sensors, 2018, 18(1), 103 (Year: 2018).*

Carraher C., Characterisation of the insect odorant receptor complex, PhD thesis of the University of Auckland, New Zealand, Sep. 2013 (Year: 2013).*
Anderson et al. (2009) "Molecular basis of female-specific odorant responses in Bombyx mori," Insect Biochemistry and Molecular Biology 39(3): 189-197.
Australian Exam Report No. 1 dated Aug. 2, 2022 in corresponding Application No. AU 2017383462 A1.
Bachtiar et al. (2013) "Multilayer Perceptron Classification of Unknown Volatile Chemicals from the Firing Rates of Insect Olfactory Sensory Neurons and Its Application to Biosensor Design," Neural Computation 25(1): 259-287.
Bachtiar et al. (publicly available Nov. 2014) "Using Multilayer Perceptron Computation to Discover Ideal Insect Olfactory Receptor Combinations in the Mosquito and Fruit Fly for an Efficient Electronic Nose," Neural Computation (Jan. 2015) 27(1): 171-201.
Bayburt et al. (2003) "Self-assembly of single integral membrane proteins into soluble nanoscale phospholipid bilayers," Protein Sci. 12(11): 2476-2481.
Bayburt et al. (2010) "Membrane protein assembly into Nanodiscs," FEBS Lett. 584(9): 1721-1727.
Booth et al. (2011) "Development of an electrochemical polypyrrole-based DNA sensor and subsequent studies on the effects of probe and target length on performance," Biosensors and Bioelectronics 28(1): 362-367.
Booth et al. (2012) "Effects of Redox Couple on the Response of Polypyrrole-Based Electrochemical DNA Sensors," Electroanalysis 24(6): 1311-1317.
Bowie et al. (1990) "Deciphering the message in protein sequences: tolerance to amino acid substitutions," Science 247(4948): 1306-1310.
Boyle et al. (2013) "Expanding the olfactory code by in silico decoding of odor-receptor chemical space," eLife 2: e01120, pp. 1-17.
Carey et al. (2010) "Odorant reception in the malaria mosquito *Anopheles gambiae*," Nature 464(7285): 66-71.
Carraher (2013) Charactisation of the Insect Odorant Receptor Complex. The University of Auckland, New Zealand, PHD thesis.
Carraher et al. (2013) "Recombinant expression, detergent solubilisation and purification of insect odorant receptor subunits," Protein Expr Purif 90(2): 160-169.
Carraher et al. (Nov. 2015) "Towards an understanding of the structural basis for insect olfaction by odorant receptors," Insect Biochemistry and Molecular Biology 66: 31-41.
Chinese First Office Action dated Jun. 30, 2021 in corresponding Application No. CN 2017800869324.
Chinese First Search dated Jun. 22, 2021 in corresponding Application No. CN 2017800869324.
Claudianos et al. (2014) "Odor memories regulate olfactory receptor expression in the sensory periphery," Eur. J. Neurosci. 39(10): 1642-1654.
Corcoran et al. (2014) "A novel method to study insect olfactory receptor function using HEK293 cells," Insect Biochem Mol Biol 54: 22-32.
Du et al. (2013) "Piezoelectric olfactory receptor biosensor prepared by aptamer-assisted immobilization," Sensors and Actuators B 187: 481-487.
Du et al. (2013) "Recent advances in olfactory receptor-based biosensors," Biosensors and Bioelectronics 42: 570-580.
Dweck et al. (Feb. 2015) "Olfactory proxy detection of dietary antioxidants in *Drosophila*," Curr Biol 25(4): 455-466.
Extended European Search Report dated Jul. 29, 2020 in corresponding Application No. EP 17885391.7.
Figueroa et al. (2010) "Large-scale investigation of the olfactory receptor space using a microfluidic microwell array," Lab Chip 10(9): 1120-1127.
Forstner et al. (2009) "A receptor and binding protein interplay in the detection of a distinct pheromone component in the silkmoth *Antheraea polyphemus*," International Journal of Biological Sciences 5(7): 745-757.
Geertsma et al. (2008) "Membrane reconstitution of ABC transporters and assays of translocator function," Nature Protocols 3(2): 256-266.

(56)          References Cited

OTHER PUBLICATIONS

Glatz et al. (2011) "Mimicking nature's noses: From receptor deorphaning to olfactory biosensing," Prog Neurobiol 93(2): 270-296.

Goldsmith et al. (2011) "Biomimetic chemical sensors using nanoelectronic readout of olfactory receptor proteins," ACS Nano 5(7): 5408-5416.

Grosse-Wilde et al. (2006) "A pheromone-binding protein mediates the bombykol-induced activation of a pheromone receptor in vitro," Chemical Senses 31(6): 547-555.

Grosse-Wilde et al. (2007) "Candidate pheromone receptors provide the basis for the response of distinct antennal neurons to pheromonal compounds," European Journal of Neuroscience 25(8): 2364-2373.

Guo et al. (2015) A novel platform based on immobilized histidine tagged olfactory receptors, for the amperometric detection of an odorant molecule characteristic of boar taint. Food Chem, 184, 1-6.

Hallem et al. (2006) "Coding of odors by a receptor repertoire," Cell 125(1): 143-160.

Heller et al. (2008) "Identifying the mechanism of biosensing with carbon nanotube transistors," Nano Lett. 8(2): 591-595.

Hill et al. (2002) "G protein-coupled receptors in Anopheles gambiae," Science 298(5591): 176-178.

Hopf et al. (Jan. 2015) "Amino acid coevolution reveals three-dimensional structure and functional domains of insect odorant receptors," Nat Commun. 13(6): 6077, pp. 1-7.

Hossein-Babaei et al. (2010) "Gas analysis by monitoring molecular diffusion in a microfluidic channel," Analytical Chemistry 82(19): 8349-8355.

Hossein-Babaei et al. (2012) "A miniature gas analyzer made by integrating a chemoresistor with a microchannel," Lab Chip 12(10): 1874-1880.

Hou et al. (2007) A novel detection strategy for odorant molecules based on controlled bioengineering of rat olfactory receptor 17. Biosens. Bioelectron. 22 (7), 1550-1555.

Huang (1994) "On Global Sequence Alignment," Computer Applications in the Biosciences 10: 227-235.

Hurot et al. (Jan. 2019) Highly sensitive olfactory biosensors for the detection of volatile organic compounds by surface plasmon resonance imaging. Biosens. Bioelectron. 123, 230-236.

International Preliminary Report on Patentability, dated Apr. 18, 2019, corresponding to International Application No. PCT/IB2017/058181 (filed Dec. 20, 2017), 6 pp.

International Search Report and Written Opinion, dated Apr. 3, 2018, corresponding to International Application No. PCT/IB2017/058181 (filed Dec. 20, 2017), 9 pp.

International Search Report and Written Opinion, dated Oct. 14, 2019, corresponding to International Application No. PCT/IB2019/054932, 10 pp.

Japanese Notice for Reasons for Refusal dated Nov. 26, 2021 in corresponding Application No. JP 2019-534131.

Japanese Search Report dated Nov. 11, 2021 in corresponding Application No. JP 2019-534131.

Jeanmougin et al. (1998) "Multiple sequence alignment with Clustal X," Trends Biochem. Sci. 23(10): 403-405.

Jones et al. (2005) Functional conservation of an insect odorant receptor gene across 250 million years of evolution. Curr. Biol. 15 (4), R119-21.

Jones et al. (2011) "Functional agonism of insect odorant receptor ion channels" with Corrections (11297-11298), Proc. Natl. Acad. Sci. U S A 108(21): 8821-8825.

Jordan et al. (2009) "Odorant receptors from the light brown apple moth (Epiphyas postvittana) recognize important volatile compounds produced by plants," Chemical Senses 34(5): 383-394.

Kannan et al. (2011) "High-Sensitivity, Label-Free DNA Sensors Using Electrochemically Active Conducting Polymers," Analytical Chemistry 83(9): 3415-3421.

Kiely et al. (2007) "Functional analysis of a Drosophila melanogaster olfactory receptor expressed in Sf9 cells," J. Neurosci. Methods 159(2): 189-194.

Kuang et al. (2010) "Biomimetic Chemosensor: Designing Peptide Recognition Elements for Surface Functionalization of Carbon Nanotube Field Effect Transistors," ACS Nano 4(1): 452-458.

Kumar et al. (2013) "A conserved aspartic acid is important for agonist (VUAA1) and odorant/tuning receptor-dependent activation of the insect odorant co-receptor (Orco)," PLOS One 8(7): e70218.

Larisika et al. (2015) Electronic Olfactory Sensor Based on A. mellifera Odorant-Binding Protein 14 on a Reduced Graphene Oxide Field-Effect Transistor. Angewandte Chemie International Edition. 54, 13245-13848.

Leary et al. (2012) "Single mutation to a sex pheromone receptor provides adaptive specificity between closely related moth species," Proc Natl Acad Sci 109(35): 14081-14086.

Lee et al. (Sep. 2015) "Bioelectronic nose combined with a microfluidic system for the detection of gaseous trimethylamine," Biosensors and Bioelectronics 71: 179-185.

Liu et al. (2013) "Identification and functional characterization of sex pheromone receptors in beet armyworm Spodoptera exigua (Hubner)," Insect Biochemistry and Molecular Biology 43(8): 747-754.

Liu et al. (2013) "Insect olfactory receptors as essential detectors for volatile chemicals in biomimetic odorant sensors," Applied Mechanics and Materials 461: 822-828.

Lu et al. (2007) Odor coding in the maxillary palp of the malaria vector mosquito Anopheles gambiae. Current biology, 17(18), pp. 1533-1544.

Lu et al. (2014) "Olfactory biosensor using odorant-binding proteins from honeybee: Ligands of floral odors and pheromones detection by electrochemical impedance," Sensors and Actuators B: Chemical 193: 420-427.

Lu et al. (2016) Impedance spectroscopy analysis f human odorant binding proteins immobilized on nanopore arrays for biochemical detection. Biosensors and Bioelectronics. 79, 251-257.

Matsubara et al. (2004) "Application of on-chip cell cultures for the detection of allergic response," Biosensors and Bioelectronics 19(7): 741-747.

Misawa et al. (2010) "Highly sensitive and selective odorant sensor using living cells expressing insect olfactory receptors," Proc. Natl. Acad. Sci. U. S. A. 107(35): 15340-15344.

Mitsuno et al. (2008) "Identification of receptors of main sex-pheromone components of three Lepidopteran species," European Journal of Neuroscience 28(5): 893-902.

Mitsuno et al. (Mar. 2015) "Novel cell-based odorant sensor elements based on insect odorant receptors," Biosens. Bioelectron. 65: 287-294.

Miura et al. (2009) "A male-specific odorant receptor conserved through the evolution of sex pheromones in Ostrinia moth species," International Journal of Biological Sciences 5(4): 319-330.

Montagne et al. (2015) "Chapter Three—Advances in the identification and characterization of olfactory receptors in insects," Progress in molecular biology and translational science 130: 55-80.

Nowotny et al. (2014) "Drosophila olfactory receptors as classifiers for volatiles from disparate real world applications," Bioinspiration & Biomimetics 9: 046007, pp. 1-13.

Panigrahi et al. (2012) Olfactory receptor-based polypeptide sensor for acetic acid VOC detection. Materials Science and Engineering C. 32, 1307-1313.

Park et al. (2012) Ultrasensitive Flexible Graphene Based Field-Effect Transistor (FET)-Type Bioelectronic Nose. Nano Letters. 12, 5082-5090.

Pask et al. (2013) "The molecular receptive range of a lactone receptor in Anopheles gambiae," Chemical Senses 38(1): 19-25.

Pitts et al. (2004) A highly conserved candidate chemoreceptor expressed in both olfactory and gustatory tissues in the malaria vector Anopheles gambiae. Proc. Natl. Acad. Sci. U. S. A. 101 (14), 5058-63.

Plank et al. (2005) "Positioning of carbon nanotubes using soft-lithography for electronics applications," J. Vac. Sci. Technol. B Microelectron. Nanom. Struct. 23(6): 3178-3181.

Robertson et al. (2003) "Molecular evolution of the insect chemoreceptor gene superfamily in Drosophila melanogaster," PNAS Nov. 25, 2003 100 (suppl 2): 14537-14542.

(56)  References Cited

OTHER PUBLICATIONS

Sakurai et al. (2004) "Identification and functional characterization of a sex pheromone receptor in the silkmoth *Bombyx mori*," Proceedings of the National Academy of Sciences of the United States of America 101(47): 16653-16658.

Sankaran et al. (2011) "Odorant binding protein based biomimetic sensors for detection of alcohols associated with *Salmonella* contamination in packaged beef," Biosensors and Bioelectronics 26(7): 3103-3109.

Sato et al. (2014) Chemical vapor detection using a reconstituted insect olfactory receptor complex. Angewandte Chemie International Edition, 53(44), pp. 11798-11802.

Schott et al. (2013) "Insect Antenna-Based Biosensors for In Situ Detection of Volatiles," Advances in Biochemical Engineering and Biotechnology 136: 101-122.

Silbering et al. (2011) "Complementary function and integrated wiring of the evolutionarily distinct *Drosophila* olfactory subsystems," Journal of Neuroscience 31(38): 13357-13375.

Smart et al. (2008) "*Drosophila* odorant receptors are novel seven transmembrane domain proteins that can signal independently of heterotrimeric G proteins," Insect Biochem Mol Biol. 38(8):770-780.

Stern et al. (2007) "Importance of the debye screening length on nanowire field effect transistor sensors," Nano Lett. 7(11): 3405-3409.

Turner et al. (2014) "Mutational analysis of cysteine residues of the insect odorant co-receptor (Orco) from *Drosophila melanogaster* reveals differential effects on agonist- and odorant-tuning receptor-dependent activation," Journal of Biological Chemistry 289(46): 31837-31845.

Wang et al. (2010) "Molecular basis of odor coding in the malaria vector mosquito *Anopheles gambiae*," Proc Natl. Acad. Sci. USA 107(9): 4418-4423.

Wang et al. (2011) "Functional characterization of pheromone receptors in the tobacco budworm *Heliothis virescens*," Insect Molecular Biology 20(1): 125-133.

Wanner et al. (2010) "Sex Pheromone Receptor Specificity in the European Corn Borer Moth, *Ostrinia nubilalis*," Plos One 5(1): e8685, pp. 1-9.

Wasilewski et al. (2018) Advances in olfaction-inspired biomaterials applied to bioelectronic noses. Sensors and Actuators B:Chemical 257, 511-537.

Xu et al. (2012) "Moth Sex Pheromone Receptors and Deceitful Parapheromones," Plos One 7(7): e41653, pp. 1-9.

Zheng et al. (Jun. 2016) "Electrostatic gating in carbon nanotube aptasensors," Nanoscale 8(28): 13659-13668.

Zheng et al. (Nov. 2015) "Carbon nanotube field effect transistor aptasensors for estrogen detection in liquids," J. Vac. Sci. Technol. B 33(6): 06F904.

Zhu et al. (Aug. 2015) "Label-free electrochemical aptasensor for femtomolar detection of 17β-estradiol," Biosensors and Bioelectronics 70: 398-403.

Zhu et al. (Feb. 2015) "Distinguishing cytosine methylation using electrochemical, label-free detection of DNA hybridization and ds-targets," Biosensors and Bioelectronics 64: 74-80.

Lee et al. (2015) "Cell-based microfluidic platform for mimicking human olfactory system," Biosensors and Bioelectronics 74: 554-561.

Son et al. (2017) "A portable and multiplexed bioelectronic sensor using human olfactory and taste receptors," Biosensors and Bioelectronics 87: 901-907.

Termtanasombat et al. (2016) "Cell-Based Odorant Sensor Array for Odor Discrimination Based on Insect Odorant Receptors," J Chem Ecol 42: 716-724.

* cited by examiner (A)

BIOSENSOR DEVICE AND METHODS

CROSS-REFERENCE TO RELATED APPLICATIONS

This application is a U.S. National Stage Application filed under 35 U.S.C. § 371 of International Application No. PCT/IB2019/054932, filed Jun. 13, 2019, which claims the benefit of New Zealand Application No. 743418, filed Jun. 13, 2018. Both of these applications are hereby incorporated by reference in their entireties.

TECHNICAL FIELD

The invention relates to sensors and methods for detecting analytes.

BACKGROUND

Real-time detection of analytes such as Volatile Organic Compounds (VOCs), and soluble organic chemicals is a critical challenge for health and environmental monitoring, as well as food safety and water quality, and there are strong drivers to develop affordable and rapid analyte sensors.

Convenient, sensitive and specific analyte sensors would have diverse applications including monitoring analytes associated with food quality/safety (flavours, ripening, contamination, and spoilage), biosecurity (pest and diseases), environmental monitoring (hazardous pollutants), medical diagnostics (e.g. breath diagnostics) and security (illicit compounds and explosives).

Insect olfactory receptors (ORs) can distinguish among a wide range of natural and synthetic chemicals, including VOCs. Insect ORs function as heteromeric ligand-gated cation channels (FIG. 1), and are composed of an obligate co-receptor known as Orco and an odorant-specific tuning receptor (OrX).

Insect ORs are structurally and functionally very different from mammalian and *Caenorhabditis elegans* ORs which function as G protein-coupled receptors (GPCRs).

A number of authors have described cell based assays for insect OR function[1] using *Xenopus* oocytes[2], insect cell lines[3-5], and human HEK293 cells[6]. However, their application was largely limited to identifying the compound specificity of insect ORs, with some being used to identify activating and inhibitory compounds for insect pest behaviour control[7].

A number of published patent documents describe insect OR cell-assays[8-13]. All cover approaches to assay for novel activating and inhibitory compounds for insect pest control. In terms of cell-based sensors, two publications[14-15] describe use of cell lines expressing insect ORs in cell-based sensor formats. One publication demonstrates the use of *Xenopus* oocytes transfected with insect ORs to detect odorants using a two-electrode voltage clamp method[14], while the other[15] describe a cell line that expresses a pheromone receptor being grown on a glass microfluidic chip and pheromone binding being detected by calcium imaging using a fluorescent microscope.

Commercially available portable volatile sensing technologies are limited to electronic/chemical e-noses, whose performance is substantially inferior to insect olfactory systems, in terms of sensitivity and specificity. Furthermore, to the best of the applicant's knowledge, there are no commercial products based on insect OR-based systems discussed above. Other technologies such as ion mobility spectrometers and mass spectrometers provide an improved sensitivity and specificity over e-noses but are very expensive to purchase, require extensive user training and are not very mobile.

It is therefore an object of the invention to provide an improved sensor device utilising at least one insect receptor and/or at least to provide the public with a useful choice.

SUMMARY OF THE INVENTION

The invention provides a sensor device comprising an insect odorant receptor complex, comprising an OrX and an Orco, coupled to the display surface/substrate of the sensor.

To the best of the applicant's knowledge this is the first time a purified insect odorant receptor complex (OrX/Orco) has been functionally immobilised on a sensor display surface/substrate.

The inventors have surprisingly shown that the novel sensor provides a highly significant increase in sensitivity relative to previously used insect OR-based systems.

The Sensor Device

In the first aspect the invention provides a sensor device comprising an insect odorant receptor complex, comprising an OrX and an Orco, in electrical communication with a substrate, wherein the sensor device is configured to detect a change in an electrical characteristic of the substrate.

In one embodiment the change in the electrical characteristic results from an interaction between the OrX in the insect odorant receptor complex, and an analyte.

In a further embodiment the interaction is binding of the analyte to the OrX in the insect odorant receptor complex.

In a further embodiment the analyte is complementary to the OrX.

In a further embodiment the interaction between the analyte and the OrX is specific.

Detection of Analyte

Thus in one embodiment the sensor is capable of detecting binding of an analyte to the OrX by detecting the change in the electrical characteristic of the substrate.

In a further embodiment the sensor is capable of detecting, in an environment, the presence of an analyte that binds to the insect OrX in the insect odorant receptor complex.

Preferably detection is specific for the analyte.

Electrical Communication

In one embodiment in electrical communication means that the insect odorant receptor complex can influence the electrical characteristic of the substrate.

In a further embodiment the interaction between the analyte and the OrX in the insect odorant receptor complex results in a conformational change in the insect odorant receptor complex.

In a further embodiment the conformational change in the insect odorant receptor complex results in the change in the electrical characteristic of the substrate.

In a further embodiment the insect odorant receptor complex forms an ion channel sensitive to the presence or otherwise of the analyte.

Coupling of the Insect Odorant Receptor Complex to the Substrate

In a further embodiment the insect odorant receptor complex is coupled to the substrate.

Presentation of the Insect Odorant Receptor Complex

In a further embodiment the insect odorant receptor complex is present in a form that is capable of undergoing a conformational change in response to interaction with the analyte.

In a further embodiment the insect odorant receptor complex is present in a membrane mimic.

The membrane mimic may be selected from a liposome, an amphipole, a detergent micelle, a nanovesicle, a lipid bilayer, and a nanodisc.

The membrane mimic may comprise amphipathic molecules such as lipid molecules. Preferably, the amphipathic molecules comprise phospholipid molecules.

Preferably the membrane mimic is artificial.

The insect odorant receptor complex may also be present in a surfactant, which may be ionic or non-ionic.

Sensitivity of Detection

In one embodiment the sensor can detect the presence of the analyte at a concentration of less than $1\times10^{-3}$M, preferably less than $1\times10^{-3}$M, more preferably less than $1\times10^{-4}$M, more preferably less than $1\times10^{-5}$M, more preferably less than $1\times10^{-6}$M, more preferably less than $1\times10^{-7}$M, more preferably less than $1\times10^{-8}$M, more preferably less than $1\times10^{-9}$M, more preferably less than $1\times10^{-10}$M, more preferably less than $1\times10^{11}$M, more preferably less than $1\times10^{-12}$M, more preferably less than $1\times10^{-13}$M, more preferably less than $1\times10^{-14}$M, more preferably less than $1\times10^{-15}$M, more preferably less than $1\times10^{-16}$M, more preferably less than $1\times10^{-17}$M, more preferably less than $1\times10^{-18}$M, more preferably less than $1\times10^{-19}$M, more preferably less than $1\times10^{-20}$M.

Substrate

In one embodiment the substrate is selected from, or composed of, at least one of: an electrode, a semiconductor material, carbon nanotubes (CNTs), graphene, an oxide, doped silicon, a conducting polymer, a resonator component, an inert metal surface on a prism.

In one embodiment the resonator component is, or is composed of, a piezoelectric material, at least one piezoelectric crystal, a quartz crystal. In a preferred embodiment the resonator component is a quartz crystal resonator.

Electrical Characteristic

In one embodiment the electrical characteristic is selected from at least one of: conductivity, resistance, complex resistance, impedance, electrochemical impedance, electrochemical potential, surface plasmon resonance, the flow of current, and the resonance frequency of oscillations induced by an alternating electric field.

Detector Component

In a further embodiment the sensor comprises a detector component which measure the change in the electrical characteristic of the substrate.

Electrochemical Impedance Spectroscopy (EIS) Sensor Device

In one embodiment of the sensor device, the substrate is the working electrode of an electrochemical cell.

In a one embodiment the electrochemical cell, in addition to the working electrode, further comprises a counter electrode.

In a further embodiment the electrochemical cell further comprises a reference electrode.

In a further embodiment the electrochemical cell further comprises a potentiostat.

In a further embodiment the electrical characteristic is electrochemical impedance.

Thus in one embodiment the sensor device comprises an insect odorant receptor complex, comprising an OrX and an Orco, in electrical communication with working electrode of an electrochemical cell, wherein sensor device is configured to detect a change in the electrochemical impedance of the working electrode.

Working Electrode of EIS Sensor Device

In one embodiment the working electrode is composed of, or coated with, gold.

Presentation of the Insect Odorant Receptor Complex in the EIS Sensor Device

The insect odorant receptor complex may be present in a membrane mimic as described above.

In one embodiment the insect odorant receptor complex is present in a liposome.

In a further embodiment the insect odorant receptor complex is present in an artificial liposome.

In a further embodiment the insect odorant receptor complex is present in a lipid bilayer.

In a further embodiment the insect odorant receptor complex is present in an artificial lipid bilayer.

In a further embodiment the insect odorant receptor complex is present in a nanodisc.

Coupling of the Insect Odorant Receptor Complex to the Electrode in the EIS Sensor Device In one embodiment the insect odorant receptor complex is coupled to the working electrode.

In a further embodiment the insect odorant receptor complex is coupled to the working electrode via a linker molecule.

In a further embodiment the linker molecule is short enough to allow electrical communication between the insect odorant receptor complex and the electrode.

In one embodiment the linker molecule is short enough to prevent isolation of the electrode from the insect odorant receptor complex.

In a further embodiment the linker molecule is selected from 16-Mercaptohexadecanoic acid (16-MHDA), 6-Mecaptohexadecanoic acid (6-MHDA) and 6-Mercaptohexanoic acid (MHA).

In a preferred embodiment the linker molecule is 6-Mercaptohexanoic acid (MHA).

In a further embodiment the linker is part of a Self-Assembled Mono (SAM) layer.

Thus in one embodiment the insect odorant receptor complex is coupled to the electrode via an SAM layer composed of the linker molecules.

In a preferred embodiment the insect odorant receptor complex is coupled to the electrode via an SAM layer composed of 6-Mercaptohexanoic acid (MHA) linker molecules.

In a further embodiment, the insect odorant receptor complex is coupled to the working electrode by interaction between the ester on the EDC/NHS and the amines on the proteins in the insect odorant receptor complex. These amines are present on both the OrX and Orco.

In a further embodiment, the insect odorant receptor complex is coupled to the working electrode by interaction between the ester on the EDC/NHS and the amines on the lipids (POPC, POPE, POPS) in the membrane mimic.

Detection of Analyte in the EIS Sensor

In a further embodiment the sensor is capable of detecting binding of an analyte to the insect odorant receptor complex.

In a further embodiment the sensor is capable of detecting, in an environment, the presence of an analyte that binds to the insect odorant receptor complex.

Preferably detection is specific for the analyte.

In a further embodiment binding of the analyte to the insect OrX changes the electrochemical impedance of the working electrode.

In a preferred embodiment the electrochemical impedance of the working electrode decreases upon binding of the analyte to the insect OrX.

In a preferred embodiment as the amount of analyte detected by the sensor, or binding to the insect OrX, changes, the electrochemical impedance of the working electrode decreases.

Detector Component

In a further embodiment the sensor comprises a detector component. In a further embodiment the detector component detects, or measures the change in electrochemical impedance of the working electrode.

Semiconductor-Based Sensor Device

In one embodiment of the sensor device, the substrate is a semiconductor material. Any suitable semiconductor material may be used.

In one embodiment of the sensor device, the semiconductor material is or is composed of at least one of: graphene, an oxide, doped silicon, conducting polymer, and carbon nanotubes (CNT).

Carbon Nanotube-Field Effect Transistor (CNT-FET) Sensor Device

In one embodiment the substrate composed of carbon nanotubes (CNT). The carbon nanotubes (CNTs) may be single wall, double wall or multiwall, or a combination thereof. In a preferred embodiment the carbon nanotubes (CNTs) are single wall.

In a further embodiment the substrate forms the channel of a carbon nanotube-field effect transistor (CNT-FET) apparatus.

In one embodiment the CNT-FET apparatus comprises a source electrode and a drain electrode.

In a further embodiment the channel is found, or formed, between the source electrode and a drain electrode.

In a further embodiment the channel is in electric communication with the source electrode and a drain electrode.

Thus in one aspect the invention provides a sensor device comprising an insect odorant receptor complex in electrical communication with at least one carbon nanotube in the channel of a carbon nanotube-field effect transistor (CNT-FET) apparatus.

In a further embodiment the carbon nanotube-field effect transistor (CNT-FET) apparatus also comprised a gate electrode.

Presentation of the Insect Odorant Receptor Complex in the CNT-FET Sensor Device The insect odorant receptor complex may be present in a membrane mimic as described above.

In a preferred embodiment the insect odorant receptor complex is present in a nanodisc.

Coupling of the Insect Odorant Receptor Complex to the Carbon Nanotube (CNT)

In one embodiment the insect odorant receptor complex is coupled to the carbon nanotube in the channel.

In a further embodiment the coupling places the insect odorant receptor complex in electrical communication with the carbon nanotube.

Insect Odorant Receptor Complex Functionalisation

In one embodiment the insect odorant receptor complex is functionalised to facilitate coupling to the CNTs.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

CNT Functionalisation

In one embodiment CNT is functionalised to facilitate coupling to the insect odorant receptor complex.

In a further embodiment the CNTs are functionalised with nickel (Ni)-nitrilotriacetic acid (NTA)

Coupling

In a further embodiment the insect odorant receptor complex is coupled to the CNTs via his-tag affinity binding.

Thus in one embodiment, the his-tagged insect odorant complex binds to the Ni-NTA functionalised CNT.

In a further embodiment, the insect odorant receptor complex is coupled to the CNT by interaction between the ester on the PBASE and the amines on the proteins in the insect odorant receptor complex. These amines are present on both the OrX and Orco.

In a further embodiment, the insect odorant receptor complex is coupled to the CNT by interaction between the ester on the PBASE and the amines on the lipids (POPC, POPE, POPS) in the membrane mimic.

Detection of Analyte in the CNT-FET Sensor

In a further embodiment the sensor is capable of detecting binding of an analyte to the insect OrX.

In a further embodiment the sensor is capable of detecting, in an environment, the presence of an analyte that binds to the insect OrX.

Preferably detection of the analyte is specific.

In a further embodiment binding of the analyte to the insect OrX changes the source-gain current in the CNT-FET apparatus.

In a preferred embodiment the source-gain current decreases upon binding of the analyte to the insect OrX.

In a preferred embodiment as the amount of analyte detected by the sensor, or binding to the insect OrX increases, the more the source-gain current decreases.

Detector Component

In a further embodiment the sensor comprises a detector component. In a further embodiment the detector component detects, or measures the change in the source-drain current.

Graphene-Field Effect Transistor (GFET) Sensor Device

In one embodiment the substrate composed of a sheet of graphene (G). The graphene may be single layer, double layer or multilayer, or a combination thereof. In a preferred embodiment the graphene is single layer.

In a further embodiment the substrate forms the channel of a graphene-field effect transistor (GFET) apparatus.

In one embodiment the GFET apparatus comprises a source electrode and a drain electrode.

In a further embodiment the channel is found, or formed, between the source electrode and a drain electrode.

In a further embodiment the channel is in electrical communication with the source electrode and a drain electrode.

Thus in one aspect the invention provides a sensor device comprising an insect odorant receptor complex in electrical communication with graphene in the channel of a graphene-field effect transistor (GFET) apparatus.

In a further embodiment the graphene-field effect transistor (GFET) apparatus also comprises a gate electrode.

Presentation of the Insect Odorant Receptor Complex in the GFET Sensor Device

The insect odorant receptor complex may be present in a membrane mimic as described above.

In a preferred embodiment the insect odorant receptor complex is present in a liposome.

Coupling of the Insect Odorant Receptor Complex to Graphene

In one embodiment the insect odorant receptor complex is coupled to graphene in the channel.

In a further embodiment the coupling places the insect odorant receptor complex in electrical communication with the graphene.

Insect Odorant Receptor Complex Functionalisation

In one embodiment the insect odorant receptor complex is functionalised to facilitate coupling to the graphene.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

Graphene Functionalisation

In one embodiment graphene is functionalised to facilitate coupling to the insect odorant receptor complex.

In a further embodiment the graphene are functionalised with 1-Pyrenebutyric acid N-hydroxysuccinimide ester (PBASE).

Coupling

In a further embodiment the insect odorant receptor complex is coupled to the graphene via his-tag affinity binding.

Thus in one embodiment, the his-tagged insect odorant complex binds to the PBASE functionalised graphene.

In a further embodiment, the insect odorant receptor complex is coupled to the graphene by interaction between the ester on the PBASE and the amines on the proteins in the insect odorant receptor complex. These amines are present on both the OrX and Orco.

In a further embodiment, the insect odorant receptor complex is coupled to the graphene by interaction between the ester on the PBASE and the amines on the lipids (POPC, POPE, POPS) in the membrane mimic.

Detection of Analyte in the GFET Sensor

In a further embodiment the sensor is capable of detecting binding of an analyte to the insect OrX.

In a further embodiment the sensor is capable of detecting, in an environment, the presence of an analyte that binds to the insect OrX.

Preferably detection of the analyte is specific.

In a further embodiment binding of the analyte to the insect OrX changes the source-gain current in the GFET apparatus.

In a preferred embodiment the source-gain current decreases upon binding of the analyte to the insect OrX.

In a preferred embodiment as the amount of analyte detected by the sensor, or binding to the insect OrX increases, the more the source-gain current decreases.

Detector Component

In a further embodiment the sensor comprises a detector component. In a further embodiment the detector component detects, or measures the change in the source-drain current.

Quartz Crystal Microbalance (QCM) Sensor Device

In one embodiment of the sensor device, the substrate is a resonator component in quartz crystal microbalance.

In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

Electrical Characteristic

In one embodiment the electrical characteristic is the resonance frequency of oscillations induced by an alternating electric field applied to the resonator component.

Electrodes of the QCM Sensor Device

In one embodiment the resonator component has at an electrode attached to two of its opposing sides.

In one embodiment the electrodes are composed of, or coated with, gold.

Presentation of the Insect Odorant Receptor Complex in the QCM Sensor Device

The insect odorant receptor complex may be present in a membrane mimic as described above.

In one embodiment the insect odorant receptor complex is present in a liposome.

In a further embodiment the insect odorant receptor complex is present in an artificial liposome.

In a further embodiment the insect odorant receptor complex is present in a lipid bilayer.

In a further embodiment the insect odorant receptor complex is present in an artificial lipid bilayer.

In a preferred embodiment the insect odorant receptor complex is present in a liposome.

Coupling of the Insect Odorant Receptor Complex to the Resonator Component in the QCM Sensor Device In one embodiment the insect odorant receptor complex is coupled to the resonator component.

In a further embodiment the insect odorant receptor complex is coupled to the resonator component via a linker molecule.

In a further embodiment the linker molecule is short enough to allow electrical communication between the insect odorant receptor complex and the resonator component.

In one embodiment the linker molecule is short enough to prevent isolation of the resonator component from the insect odorant receptor complex.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker molecule is 6-mercaptohexanoic acid (MHA).

In a further embodiment the linker is part of a Self-Assembled Monolayer (SAM).

Thus in one embodiment the insect odorant receptor complex is coupled to the resonator component via an SAM layer composed of the linker molecules.

In a preferred embodiment the insect odorant receptor complex is coupled to the resonator component via an SAM layer composed of 6-mercaptohexanoic acid (MHA) linker molecules.

Detection of Analyte with the QCM Sensor

In a further embodiment the sensor is capable of detecting binding of an analyte to the insect OrX in the insect odorant receptor complex.

In a further embodiment the sensor is capable of detecting, in an environment, the presence of an analyte that binds to the insect OrX.

Preferably detection is specific for the analyte.

In a further embodiment binding of the analyte to the insect OrX changes the resonance frequency induced by an alternating electric field applied to the resonator component.

In one embodiment the resonance frequency increases upon binding of the analyte to the insect OrX.

In a further embodiment the resonance frequency decreases upon binding of the analyte to the insect OrX.

Detector Component

In a further embodiment the sensor comprises a detector component. In a further embodiment the detector component detects, or measures the change in the resonance frequency in the resonator component induced by an alternating electric field applied to the resonator component.

In one embodiment the detector component is a frequency analyser.

Bilayer Sensor Device

In one embodiment of the sensor device, the sensor comprises a membrane mimic which comprises amphipathic molecules, an OrX protein and an Orco protein;

a first substrate which comprises a first electrode disposed at a first side of the membrane; and a second substrate which comprises a second electrode disposed at a second side of the membrane.

Electrical Characteristic

In one embodiment the electrical characteristic is electrochemical potential. In another embodiment, the electrical characteristic is the flow of current.

Electrodes of the Bilayer Sensor Device

In a one embodiment the substrate is a working electrode. In one embodiment, the sensor further comprises a counter electrode.

In a further embodiment the sensor further comprises a reference electrode.

In a further embodiment the electrochemical cell further comprises a potentiostat.

In one embodiment, one or more of the electrodes are composed of, or coated with, silver. Preferably, at least part of the electrode is covered in a silver chloride layer.

Presentation of the Insect Odorant Receptor Complex in the Bilayer Sensor Device The insect odorant receptor complex is preferably disposed in a membrane mimic as described above.

Preferably the membrane mimic comprises amphipathic molecules such as lipid molecules. Preferably, the amphipathic molecules comprise phospholipid molecules.

In a further embodiment, the OrX and Orco are ionotrophic membrane proteins. The OrX and Orco proteins together form a complex. In some embodiments, the complex forms in the presence of the analyte.

Detection of Analyte with the Bilayer Sensor

In a further embodiment the insect odorant receptor complex forms an ion channel sensitive to the presence or otherwise of the analyte.

Preferably, detection is specific for the analyte.

In a further embodiment, binding of the analyte activates the insect odorant receptor complex, causing a flow of ions across the membrane.

Preferably, the first electrode is in electrical contact with the first side of the membrane and the second electrode is in electrical contact with the second side of the membrane.

In a further embodiment, the sensor comprises a control system which is configured to measure an electrical characteristic, for example a flow of current, between the first and second electrodes.

Surface Plasmon Resonance (SPR) Sensor Device

In one embodiment of the sensor device, the substrate is an inert metal surface on a glass prism. Preferably, the metal surface is a metallic layer of silver or gold. More preferably, the metal layer has a thickness of approximately 50 nm.

Electrical Characteristic

In one embodiment the electrical characteristic is surface plasmon resonance.

Presentation of the Insect Odorant Receptor Complex in the SPR Sensor Device

The insect odorant receptor complex may be present in a membrane mimic as described above.

In one embodiment the insect odorant receptor complex is present in a liposome, for example an artificial liposome, or a nanodisc.

In a further embodiment the insect odorant receptor complex is present in a lipid bilayer, for example an artificial lipid bilayer.

In a preferred embodiment the insect odorant receptor complex is present in a liposome.

Coupling of the Insect Odorant Receptor Complex to Metallic Layer in the SPR Sensor Device In one embodiment the insect odorant receptor complex is coupled to the metal surface.

In a further embodiment the insect odorant receptor complex is coupled directly to the metal surface via a N-terminal cysteine residue.

Detection of Analyte with the SPR Sensor

In a further embodiment the sensor is capable of detecting binding of an analyte to the insect OrX in the insect odorant receptor complex.

In a further embodiment the sensor is capable of detecting, in an environment, the presence of an analyte that binds to the insect OrX.

Preferably detection is specific for the analyte.

In a further embodiment the SPR sensor comprises:

(a) a metal surface to which the insect odorant receptor complex capable of binding the analyte is bound, (b) a light source excitation beam for direction at the metal surface, (c) at least one detector capable of detecting light from the light beam which is internally reflected from the metal surface.

In a further embodiment binding of the analyte to the insect OrX causes a change in the refractive index of the sensor. Preferably this change is detected by measuring the shift in the surface plasmon resonance angle or resonance wavelength.

Detector Component

In a further embodiment the sensor comprises a detector component.

In a further embodiment the detector component detects, or measures time-variation of the resonance wavelength of the excitation beam (at fixed resonant angle) or time-shifting of the resonance angle at a fixed wavelength.

Method Using the Sensor Device of the Invention to Detect Analyte Binding

In a further aspect the invention provides a method of detecting an analyte, the method comprising the steps:

a) binding of the analyte to the insect OrX in the sensor of the invention, b) detecting a change in an electrical characteristic of the substrate, wherein the change in the electrical characteristic of the substrate indicates detection of the analyte.

Method Using the Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor c) detecting a change in an electrical characteristic of the substrate, wherein the change in the electrical characteristic of the substrate indicates presence of the analyte in the environment.

Method Using the Eis Sensor Device of the Invention to Detect Analyte Binding

In a further aspect the invention provides a method of detecting an analyte, the method comprising the steps:

a) binding of the analyte to the insect OrX in the electrochemical cell of the invention, b) measuring a change in electrochemical impedance in the working electrode, wherein the change in electrochemical impedance indicates detection of the analyte.

Method Using Eis Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the electrochemical cell of the invention, c) measuring a change in the electrochemical impedance of the working electrode, wherein the change in electrochemical impedance indicates presence of the analyte in the environment.

Method Using the CNT-FET Sensor Device of the Invention to Detect Analyte Binding In a further aspect the invention provides a method of detecting an analyte, the method comprising the steps:

a) binding of the analyte to the insect OrX in the sensor of the invention, b) measuring a change in source-gain current in the CNT-FET apparatus, wherein the change in source-gain current indicates detection of the analyte.

Method Using the CNT-FET Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor c) measuring a change of source-gain current in the CNT-FET apparatus, wherein the change in source-gain current indicates presence of the analyte in the environment.

Method Using the Graphene-FET (GFET) Sensor Device of the Invention to Detect Analyte Binding In a further aspect the invention provides a method of detecting an analyte, the method comprising the steps:

a) binding of the analyte to the insect OrX in the sensor of the invention, b) measuring a change in source-gain current in the GFET apparatus, wherein the change in source-gain current indicates detection of the analyte.

Method Using the Graphene-FET (GFET) Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor c) measuring a change of source-gain current in the GFET apparatus, wherein the change in source-gain current indicates presence of the analyte in the environment.

Method Using the QCM Sensor Device of the Invention to Detect Analyte Binding

In a further aspect the invention provides a method of detecting an analyte, the method comprising the steps:

a) binding of the analyte to the insect OrX in the sensor of the invention, b) measuring a change in the resonance frequency in the resonator component induced by an alternating electric field applied to the resonator component in the QCM apparatus, wherein the change in the resonance frequency indicates detection of the analyte.

Method Using the QCM Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor c) measuring a change of the resonance frequency of the resonator component induced by an alternating electric field applied to the resonator component in the QCM apparatus, where in the change in the resonance frequency indicates presence of the analyte in the environment.

Method Using the SPR Sensor Device of the Invention to Detect Analyte Binding

In a further aspect the invention provides a method of detecting an analyte, the method comprising the steps:

a) binding of the analyte to the insect OrX in the sensor of the invention, b) measuring a shift in the surface plasmon resonance angle or resonance wavelength, wherein the change in the surface plasmon resonance angle or resonance wavelength indicates detection of the analyte.

Method Using the SPR Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor c) measuring a shift in the surface plasmon resonance angle or resonance wavelength, wherein the change in the surface plasmon resonance angle or resonance wavelength indicates presence of the analyte in the environment.

Method Using the Bilayer Sensor Device of the Invention to Detect Analyte Binding In a further aspect the invention provides a method of detecting an analyte, the method comprising the steps:

a) binding of the analyte to the insect OrX in the sensor of the invention, b) obtaining an electrical measurement across the first and second electrodes, wherein the change in the electrical measurement indicates detection of the analyte.

Method Using Bilayer Sensor Device of the Invention to Detect the Presence of Analyte in an Environment In a further aspect the invention provides a method of detecting the presence of an analyte in an environment, the method comprising the steps:

a) exposing the sensor of the invention to an environment containing the analyte, b) binding of the analyte to the insect OrX in the sensor of the invention, c) obtaining an electrical measurement across the first and second electrodes, wherein the change in the electrical measurement indicates presence of the analyte in the environment.

Method of Manufacturing the Sensor Device of the Invention

In a further aspect the invention provides a method of manufacturing a sensor device the method including the step of establishing electrical communication between an insect odorant receptor complex comprising an OrX and an Orco, and the substrate of the sensor device, wherein the sensor device is configured to detect a change in an electrical characteristic of the substrate.

In one embodiment the method includes the step of coupling of the insect odorant receptor complex to the substrate.

In one embodiment the insect odorant receptor complex is coupled to the substrate before the insect odorant receptor complex coupled substrate is assembled in the sensor device.

Preferably the components, coupling and functionality of the sensor is/are as described herein.

Method of Manufacturing the Eis Sensor Device of the Invention

In one embodiment the substrate is the working electrode of an electrochemical cell as described herein.

Thus in one embodiment method comprises the step of establishing electrical communication between an insect odorant receptor complex and the working electrode of an electrochemical cell, wherein electrochemical cell is configured to detect a change in the electrochemical impedance of the working electrode thus forming the sensor device.

In one embodiment the method includes the step of coupling of the insect odorant receptor complex to the working electrode.

In one embodiment the insect odorant receptor complex is coupled to the working electrode before the insect odorant receptor complex coupled working electrode is assembled in the sensor device.

Preferably the components, coupling and functionality of the sensor is/are as described herein.

Coupling of the insect odorant receptor complex to the electrode.

In a further embodiment the insect odorant receptor complex is coupled to the electrode via a linker.

In one embodiment the linker molecule is short enough to allow electrical communication between the insect odorant receptor complex and the electrode.

In a further embodiment the linker molecule is short enough to prevent isolation of the electrode from the insect odorant receptor complex.

In a further embodiment the linker molecule is selected from 16-Mercaptohexadecanoic acid (16-MHDA), 6-Mecaptohexadecanoic acid (6-MHDA) and 6-Mercaptohexanoic acid (MHA).

In a preferred embodiment the linker molecule is 6-Mercaptohexanoic acid (MHA).

In a further embodiment the linker is part of a Self-Assembled Mono (SAM) layer.

Thus in one embodiment the insect odorant receptor complex is coupled to the electrode via an SAM layer composed of the linker molecules.

In a preferred embodiment the insect odorant receptor complex is coupled to the electrode via an SAM layer composed of 6-Mercaptohexanoic acid (MHA) linker molecules.

In a further embodiment activation of the carboxylic groups of the linker, or MHA, is performed prior to coupling of the insect odorant receptor complex.

Preferably, activation of the carboxylic groups of the linker, or MHA, is performed using a solution of 1-ethyl-3-(3-dimethyl amino propyl) carbodiimide (EDC) and N-hydroxysuccinimide (NHS), prior to coupling the insect odorant receptor complex to the electrode.

Method of Manufacturing the CNT-FET Sensor Device of the Invention

In one embodiment the substrate is the channel of a CNT-FET apparatus as described herein.

Thus in one embodiment method comprises the step of establishing electrical communication between an insect odorant receptor complex and the channel of an of a CNT-FET apparatus, wherein the CNT-FET apparatus is configured to detect a change in the source-gain current of the CNT-FET apparatus thus forming the sensor device.

In one embodiment the method includes the step of coupling of the insect odorant receptor complex to the channel.

In one embodiment the insect odorant receptor complex is coupled to the channel before the insect odorant receptor complex coupled channel is assembled in the sensor device.

Preferably the components, coupling and functionality of the sensor is/are as described herein.

Coupling of the Insect Odorant Receptor Complex to the Carbon Nanotube (CNT)

In one embodiment the insect odorant receptor complex is coupled to the carbon nanotube in the channel.

Insect Odorant Receptor Complex Functionalisation

In one embodiment the insect odorant receptor complex is functionalised to facilitate coupling to the CNTs.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

CNT Functionalisation

In one embodiment CNT is functionalised to facilitate coupling to the insect odorant receptor complex In a further embodiment the CNTs are functionalised with nickel (Ni)-nitrilotriacetic acid (NTA)

Coupling

In a further embodiment the insect odorant receptor complex is coupled to the CNTs via his-tag affinity binding.

Thus in one embodiment the his-tagged insect odorant receptor complex binds to the Ni-NTA functionalised CNT.

In a further embodiment, the insect odorant receptor complex is coupled to the CNT by interaction between the ester on the PBASE and the amines on the proteins in the insect odorant receptor complex. These amines are present on both the OrX and Orco.

In a further embodiment, the insect odorant receptor complex is coupled to the CNT by interaction between the ester on the PBASE and the amines on the lipids (POPC, POPE, POPS) in the membrane mimic.

Method of Manufacturing the GFET Sensor Device of the Invention

In one embodiment the substrate is the channel of a GFET apparatus as described herein.

Thus in one embodiment method comprises the step of establishing electrical communication between an insect odorant receptor complex and the channel of an of a GFET apparatus, wherein the GFET apparatus is configured to detect a change in the source-gain current of the GFET apparatus thus forming the sensor device.

In one embodiment the method includes the step of coupling of the insect odorant receptor complex to the channel.

In one embodiment the insect odorant receptor complex is coupled to the channel before the insect odorant receptor complex coupled channel is assembled in the sensor device.

Preferably the components, coupling and functionality of the sensor is/are as described herein.

Coupling of the Insect Odorant Receptor Complex to the Graphene

In one embodiment the insect odorant receptor complex is coupled to the graphene in the channel.

Insect Odorant Receptor Complex Functionalisation

In one embodiment the insect odorant receptor complex is functionalised to facilitate coupling to the graphene.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

Graphene Functionalisation

In one embodiment graphene is functionalised to facilitate coupling to the insect odorant receptor complex In a further embodiment the graphene is functionalised with 1-Pyrenebutyric acid N-hydroxysuccinimide ester (PBASE).

Coupling

In a further embodiment the insect odorant receptor complex is coupled to the graphene via his-tag affinity binding.

Thus in one embodiment the his-tagged insect odorant receptor complex binds to the PBASE functionalised graphene.

In a further embodiment, the insect odorant receptor complex is coupled to the graphene by interaction between the ester on the PBASE and the amines on the proteins in the insect odorant receptor complex. These amines are present on both the OrX and Orco.

In a further embodiment, the insect odorant receptor complex is coupled to the graphene by interaction between the ester on the PBASE and the amines on the lipids (POPC, POPE, POPS) in the membrane mimic.

Method of Manufacturing the QCM Sensor Device of the Invention

In one embodiment the substrate is the quartz crystal resonator of a quartz crystal microbalance.

Thus in one embodiment method comprises the step of establishing electrical communication between an insect odorant receptor complex and the resonator component of a quartz crystal microbalance, wherein quartz crystal microbalance is configured to detect a change in the resonance frequency of the resonator component induced by an alternating electric field applied to the resonator component in the QCM apparatus, thus forming the sensor device.

In one embodiment the method includes the step of coupling of the insect odorant receptor complex to the resonator component.

In one embodiment the insect odorant receptor complex is coupled to the resonator component before the insect odorant receptor complex coupled working resonator component is assembled in the sensor device.

Preferably the resonator component is a quartz crystal resonator.

Preferably the components, coupling and functionality of the sensor is/are as described herein.

Coupling of the Insect Odorant Receptor Complex to the Resonator Component

In a further embodiment the insect odorant receptor complex is coupled to the resonator component via a linker.

In one embodiment the linker molecule is short enough to allow electrical communication between the insect odorant receptor complex and the resonator component.

In a further embodiment the linker molecule is short enough to prevent isolation of the resonator component from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker molecule is 6-mercaptohexanoic acid (MHA).

In a further embodiment the linker is part of a Self-Assembled Monolayer (SAM).

Thus in one embodiment the insect odorant receptor complex is coupled to the resonator component via an SAM layer composed of the linker molecules.

In a preferred embodiment the insect odorant receptor complex is coupled to the resonator component via an SAM layer composed of 6-mercaptohexanoic acid (MHA) linker molecules.

In a further embodiment activation of the carboxylic groups of the linker, or MHA, is performed prior to coupling of the insect odorant receptor complex.

Preferably, activation of the carboxylic groups of the linker, or MHA, is performed using a solution of 1-ethyl-3-(3-dimethyl amino propyl) carbodiimide (EDC) and N-hydroxysuccinimide (NHS), prior to coupling the insect odorant receptor complex to the resonator component.

DETAILED DESCRIPTION OF THE INVENTION

The applicant's invention successfully combines the smelling power of insect odorant receptors with a convenient sensor format.

In addition to the improved convenience, the sensor device of the invention provides surprisingly significant improvements in sensitivity of detection versus previous assay systems based on use of insects ORs.

Insect Odorant Receptor Complexes

Insect odorant receptors (ORs) are members of a novel family of seven-transmembrane proteins that form ligand-gated non-selective cation channels. The highly conserved insect odorant co-receptor (Orco), is thought to form the active channel in vivo, with odorant specificity conferred by a panel of ligand-binding subunits (OrX) as represented in FIG. 1.

Preferably detection is specific for the analyte.

In vivo, the N-terminus of insect an OrX protein is cytoplasmic, while the C-terminus is extracellular. This topology is the opposite that of mammalian G-protein coupled receptors (GPCRs). In addition, unlike mammalian GPCRs, insect ORs function as ligand-gated non-selective cation channels, and signal largely independently of G proteins[16-17].

Hopf et al 2015[18] further discusses the predicted structure of insect ORs and their unrelatedness to mammalian GPCRs.

Insect OrX

Insect OrX proteins, which may also be described as OrX polypeptides, are well known to those skilled in the art. Suitable OrX sequences for use in the invention include those from the *Drosophila melanogaster* OR gene family ([19]) which can detect a wide range of VOCs ([20-22]), the *Anopheles gambiae* OR gene family ([23]) which can detect a wide range of VOCs ([24-25]); as well as OR gene families from other insect species, for a recent list of known OR families see Table I of Montagne 2015 ([1]). In one embodiment the insect OrX protein comprises a sequence disclosed in such references[1, 19] and[23], or a variant or functional fragment thereof.

Insect Odorant Co-Receptor (Orco)

Insect odorant co-receptor (Orco) proteins (also known as Or83b[26]), which may also be described as Orco polypeptides, are well known to those skilled in the art. Suitable Orco sequences for use in the invention include those from the *Drosophila melanogaster* Orco gene family ([19]), the *Anopheles gambiae* Orco gene family ([23, 27]) as well as Orco gene families from other insect species, for a recent list of known Orco families see Table I of Montagne 2015 ([1]). In one embodiment the insect Orco protein comprises a sequence disclosed in such references[1, 19] and[23, 27], or a variant or functional fragment thereof.

Nature of the OrX Proteins

In one embodiment the OrX in the receptor complex is a recombinantly expressed protein.

In a preferred embodiment the OrX has been purified after recombinant expression.

In one embodiment the OrX is not purified directly from an insect olfactory cells.

In a further embodiment the OrX is not present in an insect olfactory cell in the sensor device.

Nature of the Orco Proteins

In one embodiment the Orco in the receptor complex is a recombinantly expressed protein.

In a preferred embodiment the Orco has been purified after recombinant expression.

In one embodiment the Orco is not purified directly from an insect olfactory cells.

In a further embodiment the Orco is not present in an insect olfactory cell in the sensor device.

Substrates for Use in the Sensor Device of the Invention

The substrate for use in the sensor device of the invention may be any substrate in which a change in an electrical characteristic can be measured. Preferably the change in the electrical characteristic is as a result of interaction between the OrX and the analyte.

The substrate may also provide the surface to which the insect odorant receptor complex can be coupled.

Suitable substrates include, or are composed of, at least one of: an electrode, a semiconductor material, carbon nanotubes (CNTs), graphene, an oxide, doped silicon, a conducting polymer, a resonator component, an inert metal surface on a prism.

In one embodiment the resonator component is, or is composed of, a piezoelectric material, at least one piezo-electric crystal, and a quartz crystal. In a preferred embodiment the resonator component is a quartz crystal resonator.

Electrical Characteristics to Measure in the Sensor Device of the Invention

In one embodiment the electrical characteristic is selected from at least one of: conductivity, resistance, complex resistance, impedance, electrochemical impedance, electrochemical potential, surface plasmon resonance, the flow of current, and the resonance frequency of oscillations induced by an alternating electric field.

EIS Device

In one embodiment the sensor device of the invention is configured to detect a change in electrochemical impedance in the working electrode of a chemical cell. Thus the sensor device in this embodiment is configured for Electrochemical Impedance Spectroscopy (EIS).

Electrochemical Impedance Spectroscopy (EIS)

Electrochemical Impedance Spectroscopy is well known to those skilled in the art, and has long been employed for studying electrochemical systems. For impedance measurements, a small sinusoidal AC voltage probe (typically 2-10 mV) is applied, and the current response is determined. The in-phase current response determines the real (resistive) component of the impedance, while the out-of-phase current response determines the imaginary (capacitive) component. The AC probe voltage should be small enough so that the system response is linear, allowing simple equivalent circuit analysis. Impedance methods are quite powerful, in that they are capable of characterizing physicochemical processes of widely differing time constants, sampling electron transfer at high frequency and mass transfer at low frequency.

Impedance results are commonly fitted to equivalent circuits of resistors and capacitors, such as the Randles circuit which is often used to interpret simple electrochemical systems. The Randles circuit [Rs+CPE/(Rct+W)] comprises a solution resistance (Rs) in series with a constant phase element (CPE) and in parallel with charge transfer resistance (Rct) and Warburg diffusion element (W).

If an analyte affects one or more of these equivalent circuit parameters and these parameters are not affected by interfering species, then impedance methods can be used for analyte detection.

The Warburg impedance, which can be used to measure effective diffusion coefficients, is seldom useful for analytical applications. The equivalent circuit elements that are most often useful for analyte detection are Rct and CPE. The measured capacitance usually arises from the series combination of several elements, such as analyte binding to a sensing layer on a gold (Au) electrode.

Electrochemical Impedance Spectroscopy (EIS) Devices

EIS device typically comprise an electrochemical cell with:

a working electrode (WE)
a counter electrode (CE)
a reference electrode (RE)
a potentiostat/galvanostat (PGSTAT)

Depending on the application, the connections of the instrument to the electrochemical cell can be (or must be) set up in different ways.

In potentiostatic mode, a potentiostat/galvanostat (PG-STAT) will accurately control the potential of the Counter Electrode (CE) against the Working Electrode (WE) so that the potential difference between the working electrode (WE) and the Reference Electrode (RE) is well defined, and correspond to the value specified by the user. In galvanostatic mode, the current flow between the WE and the CE is controlled. The potential difference between the RE and WE and the current flowing between the CE and WE are continuously monitored. By using a PGSTAT, the value specified by the user (i.e. applied potential or current) is accurately controlled, anytime during the measurement by using a negative feedback mechanism.

The counter electrode (CE), is an electrode which is used to close the current circuit in the electrochemical cell. It is usually made of an inert material (e.g. Pt, Au, graphite, glassy carbon) and usually it does not participate in the electrochemical reaction. Because the current is flowing between the WE and the CE, the total surface area of the CE (source/sink of electrons) must be higher than the area of the WE so that it will not be a limiting factor in the kinetics of the electrochemical process under investigation.

The reference electrode (RE) is an electrode which has a stable and well-known electrode potential and it is used as a point of reference in the electrochemical cell for the potential control and measurement. The high stability of the reference electrode potential is usually reached by employing a redox system with constant (buffered or saturated) concentrations of each participants of the redox reaction. Moreover, the current flow through the reference electrode is kept close to zero (ideally, zero) which is achieved by using the CE to close the current circuit in the cell together with a very high input impedance on the electrometer (>100 GOhm).

The working electrode (WE) is the electrode in an electrochemical system on which the reaction of interest is occurring. Common working electrodes can be made of inert materials such as Au, Ag, Pt, glassy carbon (GC) and Hg drop and film.

The EIS device may also include a component to measure changes in an electrical property of the working electrode. For example, this component may be a frequency analyser. The frequency analyser may be linked to the potentiostat/galvanostat.

CNT-FET Device

In one embodiment the sensor device of the invention is configured to detect a change in source-gain current of the CNT-FET apparatus.

Carbon Nanotube Field-Effect Transistor (CNT-FET)

A carbon nanotube field-effect transistor (CNT-FET) is a field-effect transistor that utilizes a single carbon nanotube or an array of carbon nanotubes as the channel material instead of bulk silicon in the traditional metal-oxide-semiconductor field-effect transistor (MOS-FET) structure.

CNT-FET Devices

CNT-FET devices typically comprise:

a) a source electrode (SE)
b) a drain electrode (DE)
c) a gate electrode (GE), and
d) at least one channel composed of carbon nanotubes (CNTs)

The gate electrode is used to control the current across the source and drain electrodes. When the gate electrode is on, current flow is able to be modulated across the source and drain electrodes through the channel.

The electrodes are typically composed of at least one metal. Preferred metals include, but are not limited to: platinum, gold, chrome, copper, aluminium, tickle, palladium and titanium.

In a Preferred Embodiment the Channel is Composed of Carbon Nanotubes

The CNT-FET device may also include a component to measure changes in the source-drain current.

GFET Device

In one embodiment the sensor device of the invention is configured to detect a change in source-gain current of the GFET apparatus.

Graphene-Field-Effect Transistor (GFET)

A carbon nanotube field-effect transistor (GFET) is a field-effect transistor that utilizes graphene as the channel material instead of bulk silicon in the traditional metal-oxide-semiconductor field-effect transistor (MOS-FET) structure.

GFET Devices

GFET devices typically comprise:

e) a source electrode (SE)
f) a drain electrode (DE)
g) a gate electrode (GE), and
h) at least one channel composed of graphene The gate electrode is used to control the current across the source and drain electrodes. When the gate electrode is on, current flow is able to be modulated across the source and drain electrodes through the channel.

The electrodes are typically composed of at least one metal. Preferred metals include, but are not limited to: platinum, gold, chrome, copper, aluminium, tickle, palladium and titanium.

In a Preferred Embodiment the Channel is Composed of Carbon Nanotubes

The GFET device may also include a component to measure changes in the source-drain current.

QCM Device

In one embodiment the sensor device of the invention is configured to detect a change in resonant oscillation frequency of the resonator component in a quartz crystal microbalance (QCM).

In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

Quartz Crystal Microbalance (QCM)

Quartz crystal microbalance (QCM) technology is well known to those skilled in the art, and measures a mass variation per unit area by measuring the change in frequency of a quartz crystal resonator. The resonance is disturbed by the addition or removal of a small mass due to oxide growth/decay or film deposition at the surface of the acoustic resonator. The QCM can be used under vacuum, in gas phase and in liquid environments. It is highly effective at determining the affinity of molecules (proteins, in particular) to surfaces functionalized with recognition sites. QCM has also been used to investigate interactions between biomolecules. Frequency measurements are easily made to high precision, hence, it is easy to measure mass densities down to a level of below 1 μg/cm². In addition to measuring the frequency, the dissipation factor (equivalent to the resonance bandwidth) is often measured to help analysis. The dissipation factor is the inverse quality factor of the resonance, $Q^{-1} = w/f_r$; it quantifies the damping in the system and is related to the sample's viscoelastic properties.

Quartz is one member of a family of crystals that experience the piezoelectric effect. The relationship between applied voltage and mechanical deformation is well known; this allows probing an acoustic resonance by electrical means. Applying alternating current to the quartz crystal will induce oscillations. With an alternating current between the electrodes of a properly cut crystal, a standing shear wave is generated. The Q factor, which is the ratio of frequency and bandwidth, can be as high as 106. Such a narrow resonance leads to highly stable oscillators and a high accuracy in the determination of the resonance frequency. The QCM exploits this ease and precision for sensing. Common equipment allows resolution down to 1 Hz on crystals with a fundamental resonant frequency in the 4-6 MHz range.

The frequency of oscillation of the quartz crystal is partially dependent on the thickness of the crystal. During normal operation, all the other influencing variables remain constant; thus a change in thickness correlates directly to a change in frequency. As mass is deposited on the surface of the crystal, the thickness increases; consequently the frequency of oscillation decreases from the initial value. With some simplifying assumptions, this frequency change can be quantified and correlated precisely to the mass change using the Sauerbrey equation.

Quartz Crystal Microbalance (QCM) Devices

A typical setup for the QCM contains water cooling tubes, the retaining unit, frequency sensing equipment through a microdot feed-through, an oscillation source, and a measurement and recording device.

The QCM consists of a resonator component (typically a thin piezoelectric plate) with electrodes evaporated onto both sides. Due to the piezo-effect, an AC voltage across the electrodes induces a shear deformation and vice versa. The electromechanical coupling provides a simple way to detect an acoustic resonance by electrical means. Otherwise, it is of minor importance.

Bilayer Devices

A typical setup for the bilayer device combines biological components such as lipid bilayers and proteins with electronics to provide an output signal in response to stimulus from an analyte or family of analytes of interest.

The bilayer device comprises an insect odorant receptor complex that forms an ion channel which is gated (activated/inactivated) by an analyte, mounted in an electrical circuit, wherein the binding of the analyte to the OrX causes a flow of current through the ion channel that is measured using the electrical circuit.

SPR Devices

A typical setup for the SPR device comprises:
(a) a sensor providing a metallic sensor surface capable of binding the analyte:

(b) a light source excitation beam for direction at the sensor surface:
(c) at least one detector capable of detecting light from the light beam which is internally reflected from the sensor surface.

The SPR device comprises an insect odorant receptor complex coupled to the metallic surface, wherein binding of the analyte to the insect OrX causes a change in the refractive index of the sensor. Preferably this change can be detected by measuring the shift in the surface plasmon resonance angle or resonance wavelength.

Sensor Device of the Invention

In the first aspect the invention provides a sensor device comprising an insect odorant receptor complex comprising an OrX and an Orco, in electrical communication with a substrate, wherein the sensor device is configured to detect a change in an electrical characteristic of the substrate.

Sensor Component

In a further aspect the invention provides a component for a sensor device, the component comprising an insect odorant receptor complex comprising an OrX and an Orco, in electrical communication with a substrate as herein defined. This component is useful for adding to a sensor device according to the invention.

In one aspect the invention provides a sensor device component comprising an insect odorant receptor complex, comprising an OrX and an Orco, in electrical communication with a substrate.

In one aspect the invention provides as sensor device comprising the sensor device component of the invention, wherein the sensor device is configured to detect a change in an electrical characteristic of the substrate.

In a further aspect the invention provides a method of manufacturing a sensor device component, the method including the step of establishing electrical communication between an insect odorant receptor complex comprising an OrX and an Orco, and a substrate.

In a further aspect the invention provides a method of assembling a sensor device, the method comprising adding sensor device component of the invention to the sensor device, wherein the assembled sensor device is configured to detect a change in an electrical characteristic of the substrate.

In certain embodiments of the sensor device component and sensor device, the insect odorant receptor complex, electrical communication, substrate, configuration, and detection, are as described herein.

Electrochemical Impedance Spectroscopy (EIS) Apparatus

In one embodiment the sensor device comprises an electrochemical cell.

In one embodiment the electrochemical cell comprises at least two electrodes.

In a further embodiment the electrochemical cell comprises at least:
a) a working electrode (WE), and
b) a counter electrode (CE)

In a preferred embodiment the electrochemical cell also comprises a reference electrode (RE).

In a further embodiment the electrochemical cell comprises a potentiostat/galvanostat (PGSTAT)

In a preferred embodiment the electrochemical cell comprises all of:
a) a working electrode (WE),
b) a counter electrode (CE),
c) a reference electrode (RE), and
d) potentiostat/galvanostat (PGSTAT).

Counter Electrode

In one embodiment the counter electrode is composed of, or coated with a material selected from platinum (Pt), gold (Au), graphite or glassy carbon (GC).

Preferably the counter electrode is composed of a platinum (Pt).

Preferably the counter electrode is a platinum (Pt) wire.

Reference Electrode

Preferably the reference electrode is a silver/silver chloride (Ag/AgCl) reference electrode Working Electrode In one embodiment the Electrochemical Impedance Spectroscopy (EIS) apparatus comprises at least one working electrode.

The electrode may be composed of, or coated with, any suitable material. The electrode may be composed of, or coated with, a material selected from gold (Au), silver Ag), platinum (Pt), carbon nanotubes (CNT) and glassy carbon (GC).

In a preferred embodiment the electrode is composed of, or coated with, gold.

Potentiostat/galvanostat (PGSTAT)

Preferably the potentiostat/galvanostat (PGSTAT) is used in potentiostatic mode.

Detector Component

In a further embodiment the sensor comprises a detector component. The detector component detects, or measures the change in the electrical characteristic of the substrate.

In one embodiment the detector component is a frequency analyser. In a further embodiment the frequency analyser is linked to the potentiostat/galvanostat (PGSTAT).

Preparation of Insect OrX Proteins

Methods for recombinantly expressing and purifying insect OrX and Orco proteins are known to those skilled in the art[28].

Presentation of the Preparation of Insect OrXs

In a further embodiment the insect odorant receptor complex is present in a form that is capable of undergoing a conformational change in response to interaction with the analyte.

In one embodiment the insect odorant receptor complex is present in a membrane mimic.

A membrane mimic as the name suggests mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In one embodiment the membrane mimic is a liposome.

In one embodiment the membrane mimic is an artificial liposome.

In a further embodiment the membrane mimic is a lipid bilayer.

In a further embodiment the membrane mimic is an artificial lipid bilayer.

Methods for reconstituting insect receptor proteins (OrX and Orco) in liposomes are known in the art[28].

Formation of a Lipid Bilayers Comprising the Insect Odorant Receptor Complex on the Working Electrode Without wishing to be bound by theory, the applicants postulate that in some embodiments when the insect odorant receptor complex in liposomes, are applied to the working electrode, the liposome changes structure to form a lipid bilayer on the electrode. The applicants postulate that the insect odorant receptor complex is embedded in the lipid bilayer in similar or same conformation as found in cell membranes in vivo, such that the ligand/analyte binding domain of the OrX receptor of the accessible to the ligand/analyte.

Without wishing to be bound by theory, the applicants postulate that in other embodiments the liposomes remain as liposomes when bound to the working electrode. This is exemplified in FIG. 2.

Coupling of the Insect Odorant Receptor Complex to the Substrate

In a further embodiment the insect odorant receptor complex is coupled to the substrate.

Numerous methods for coupling proteins to substrates are known to those skilled in the art. Such methods include use of covalent chemical coupling, photochemical cross-linking, surface coating/modification, gold surface chemistry, protein affinity tags, biotin-streptavidin linkages, antibody immobilization, and engineered surface-binding peptide sequences.

The OrX and Orco proteins for use in the present devices may also include an amine group, a histidine tag, or some other functionalization used to couple the insect odorant receptor complex to the substrate. In the case of a protein having an amine group, the user may use the amine group to displace a leaving group coupled to the substrate so as to bind the protein to the substrate. The coupling need not necessarily be accomplished by a nucleophile-leaving group reaction, as coupling may occur by covalent bond (e.g., an amide bond), an ionic bond, by hydrogen bonding, or by metallic coordination. As one example of coordination, the OrX or Orco protein may be coupled to the substrate by coordination between a histidine tag and nickel. An OrX or Orco protein may also be coupled to the substrate by way of a cysteine residue. In some embodiments, the OrX or Orco protein to be attached naturally includes a cysteine residue. This could be naturally occurring or such a residue could be intentionally incorporated into a natural or recombinant protein. Further information may be found in WO2012050646.

In some embodiments, a surface of the substrate comprises a functional group linking the substrate to the transmembrane protein. In one non-limiting example, the surface of the material may be functionalized wit carboxylated diazonium salts, which spontaneously form covalent bonds to substrates such as carbon nanotubes. Amine and amide functionalities are considered suitable, as are phenolic/aromatic functionalities.

Linker for EIS

In a further embodiment the insect odorant receptor complex is coupled to the electrode via a linker.

In one embodiment the linker molecule is short enough to allow electrical communication between the insect odorant receptor complex and the electrode.

In a further embodiment the linker molecule is short enough to prevent isolation of the electrode from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker is 6-Mercaptohexanoic acid (MHA).

In a further embodiment linker is part of a Self-Assembled Mono (SAM) layer.

Thus in one embodiment the SAM layer is composed 6-mercaptohexanoic acid (MHA).

In a further embodiment activation of the carboxylic groups of the MHA is performed prior to coupling of the insect odorant receptor complex.

Preferably, activation of the carboxylic groups of the MHA is performed using a solution of 1-ethyl-3-(3-dimethyl amino propyl) carbodiimide (EDC) and N-hydroxysuccinimide (NHS), prior to coupling the insect odorant receptor complex to the electrode.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OrX changes the electrochemical impedance in the working electrode.

Carbon Nanotube Field-Effect Transistor (CNT-FET) Apparatus

Preferably the carbon nanotube field-effect transistor (CNT-FET) apparatus comprises at least two terminals. In a further embodiment the CNT-FET apparatus comprises at least a source electrode and a drain electrode.

In one embodiment the CNT-FET apparatus comprises:
a) a source electrode
b) a drain electrode
c) a gate electrode
d) at least one channel composed of carbon nanotubes (CNTs)

Preferably the gate electrode is a silver/silver chloride (Ag/AgCl) wire.

Detector Component

In a further embodiment the sensor comprises a detector component. The detector component detects, or measures the change in source-drain current.

Changes in electrical characteristics can be measured using conventional electronic instrumentation that is operated manually or under computer control. For example, a computerized laboratory set up might include a National Instrument PCI-6722 DAQ board to apply the bias voltage and various values of gate voltage. A Keithley 6485 Picoammeter could then be used to measure current, providing a full I-Vg curve. In the case where one wished to measure many devices located on a single substrate, a switching matrix (Keithley 7001) or other multiplexer could be used.

An Agilent 4156C parameter analyser can also be used for all electrical measurements. The parameter analyser has excellent sensitivity and can accurately measure currents on the femto-amp scale.

Presentation of the Insect Odorant Receptor Complex

In a further embodiment the insect odorant receptor complex is present in a form that is capable of undergoing a conformational change in response to interaction with the analyte.

In one embodiment the insect odorant receptor complex is present in a membrane mimic.

A membrane mimic as the name suggests mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In a preferred embodiment the membrane mimic is a nanodisc.

Coupling of the Insect Odorant Receptor Complex to the Channel in the CNT-FET Device of the Invention In one embodiment the insect odorant receptor complex is coupled to the carbon nanotube in the channel.

Insect Odorant Receptor Complex Functionalisation

In one embodiment the insect odorant receptor complex is functionalised to facilitate coupling to the CNTs.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

CNT Functionalisation

In one embodiment CNT is functionalised to facilitate coupling of the insect odorant receptor complex.

In a further embodiment the CNTs are functionalised with nickel (Ni)-nitrilotriacetic acid (NTA)

Coupling

In a further embodiment the insect odorant receptor complex is coupled to the CNTs via his-tag affinity binding.

Thus in one embodiment, the his-tagged insect odorant receptor complex binds to the Ni-NTA functionalised CNT.

In a further embodiment, the insect odorant receptor complex is coupled to the CNT by interaction between the ester on the PBASE and the amines on the proteins in the insect odorant receptor complex. These amines are present on both the OrX and Orco.

In a further embodiment, the insect odorant receptor complex is coupled to the CNT by interaction between the ester on the PBASE and the amines on the lipids (POPC, POPE, POPS) in the membrane mimic.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OR changes the electrical source-gain current in the channel of the CNT-FET apparatus of the invention.

Graphene Field-Effect Transistor (GFET) Apparatus

Preferably the graphene field-effect transistor (GFET) apparatus comprises at least two terminals. In a further embodiment the GFET apparatus comprises at least a source electrode and a drain electrode.

In one embodiment the GFET apparatus comprises:
e) a source electrode
f) a drain electrode
g) a gate electrode
h) at least one channel composed of graphene Preferably the gate electrode is a silver/silver chloride (Ag/AgCl) wire.

Detector Component

In a further embodiment the sensor comprises a detector component. The detector component detects, or measures the change in source-drain current.

Changes in electrical characteristics can be measured using conventional electronic instrumentation that is operated manually or under computer control. For example, a computerized laboratory set up might include a National Instrument PCI-6722 DAQ board to apply the bias voltage and various values of gate voltage. A Keithley 6485 Picoammeter could then be used to measure current, providing a full I-Vg curve. In the case where one wished to measure many devices located on a single substrate, a switching matrix (Keithley 7001) or other multiplexer could be used.

An Agilent 4156C parameter analyser can also be used for all electrical measurements. The parameter analyser has excellent sensitivity and can accurately measure currents on the femto-amp scale.

Presentation of the Insect Odorant Receptor Complex

In a further embodiment the insect odorant receptor complex is present in a form that is capable of undergoing a conformational change in response to interaction with the analyte.

In one embodiment the insect odorant receptor complex is present in a membrane mimic.

A membrane mimic as the name suggests mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In a preferred embodiment the membrane mimic is a liposome.

Coupling of the Insect Odorant Receptor Complex to the Channel in the GFET Device of the Invention In one embodiment the insect odorant receptor complex is coupled to the graphene in the channel.

Insect Odorant Receptor Complex Functionalisation

In one embodiment the insect odorant receptor complex is functionalised to facilitate coupling to the graphene.

In one embodiment the insect odorant receptor complex is functionalised with a his-tag.

Therefore, in one embodiment the insect odorant receptor complex comprises a his-tag.

In one embodiment the OrX protein comprises a his-tag.

Preferably the his-tag is at the N-terminus of the OrX protein.

In a further embodiment the Orco protein comprises a his-tag.

Preferably the his-tag is at the N-terminus of the Orco protein.

In a further embodiment the both the OrX and Orco protein comprise a his-tag as above.

Graphene Functionalisation

In one embodiment graphene is functionalised to facilitate coupling of the insect odorant receptor complex.

In a further embodiment the graphene is functionalised with 1-Pyrenebutyric acid N-hydroxysuccinimide ester (PBASE).

Coupling

In a further embodiment the insect odorant receptor complex is coupled to the graphene via his-tag affinity binding.

Thus in one embodiment, the insect odorant receptor complex is coupled to the graphene by interaction between the ester on the PBASE and the amines on the proteins in the insect odorant receptor complex. These amines are present on both the OrX and Orco.

In a further embodiment, the insect odorant receptor complex is coupled to the graphene by interaction between the ester on the PBASE and the amines on the lipids (POPC, POPE, POPS) in the membrane mimic.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OR changes the electrical source-gain current in the channel of the GFET apparatus of the invention.

Quartz Crystal Microbalance (QCM) Apparatus

Preferably the quartz crystal microbalance (QCM) apparatus comprises:

a) a resonator component b) an oscillation source component c) a frequency sensing component Resonator Component In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

In one embodiment the resonator component has an electrode attached to two of it opposing sides.

In one embodiment the electrodes are composed of, or coated with, gold.

In a preferred embodiment the resonator component is in electrical communication with at least one insect odorant receptor complex.

Oscillation Source Component

In one embodiment the oscillation source component is configured to apply an alternating electric field to the resonator component.

In one embodiment alternating electric field is applied via the electrodes attached to opposing sides of the resonator component.

Frequency Sensing Component

In one embodiment the frequency sensing component is configured to measure the oscillation frequency of the resonator component. In one embodiment the frequency sensing component is configured to measure changes in the oscillation frequency of the resonator component.

Presentation of the Insect Odorant Receptor Complex

In a further embodiment the insect odorant receptor complex is present in a form that is capable of undergoing a conformational change in response to interaction with the analyte.

In one embodiment the insect odorant receptor complex is present in a membrane mimic.

A membrane mimic, as the name suggests, mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In a preferred embodiment the membrane mimic is a liposome.

In a further embodiment the membrane mimic is a lipid bilayer.

In a further embodiment the membrane mimic is an artificial lipid bilayer.

Methods for reconstituting insect receptors in liposomes are known in the art[28].

Formation of a Lipid Bilayers Comprising the Insect Odorant Receptor Complex on the Resonator Component Without wishing to be bound by theory, the applicants postulate that in some embodiments when the insect odorant receptor complexes in liposomes, are applied to the working electrode, the liposome changes structure to form a lipid bilayer on the resonator component. The applicants postulate that the insect odorant receptor complex are embedded in the lipid bilayer in similar or same conformation as found in cell membranes in vivo, such that the ligand/analyte binding domain of the receptor of the accessible to the ligand/analyte.

Without wishing to be bound by theory, the applicants postulate that in other embodiments the liposomes remains as liposomes when bound to the working electrode. This is exemplified in FIG. 2.

Linker for QCM

In a further embodiment the insect odorant receptor complex is coupled to the resonator component via a linker.

In one embodiment the linker molecule is short enough to allow electrical communication between the insect odorant receptor complex and the resonator component.

In a further embodiment the linker molecule is short enough to prevent isolation of the resonator component from the insect odorant receptor complex.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker is 6-mercaptohexanoic acid (MHA).

In a further embodiment linker is part of a Self-Assembled Monolayer (SAM).

Thus in one embodiment the SAM layer is composed 6-mercaptohexanoic acid (MHA).

In a further embodiment activation of the carboxylic groups of the MHA is performed prior to coupling of the insect odorant receptor complex.

Preferably, activation of the carboxylic groups of the MHA is performed using a solution of 1-ethyl-3-(3-dimethyl amino propyl) carbodiimide (EDC) and N-hydroxysuccinimide (NHS), prior to coupling the insect OrX to the electrode.

Detection of Analyte

In a further embodiment the sensor is capable of detecting binding of an analyte to the insect OrX in the insect odorant receptor complex.

In a further embodiment the sensor is capable of detecting in an environment the presence of an analyte that binds to the insect OrX.

Preferably detection of the analyte is specific.

In a further embodiment binding of the analyte to the insect OrX changes the resonance frequency of the resonator component induced by an alternating electric field applied to the resonator component.

Bilayer Device

In one embodiment of the sensor device, the sensor comprises a membrane mimic which comprises amphipathic molecules, an OrX protein and an Orco protein;

a first substrate which comprises a first electrode disposed at a first side of the membrane; and a second substrate which comprises a second electrode disposed at a second side of the membrane.

Electrical Characteristic

In one embodiment the electrical characteristic is electro-chemical potential. In another embodiment, the electrical characteristic is the flow of current.

Electrodes of the Bilayer Sensor Device

In a one embodiment the substrate is a working electrode. In one embodiment, the sensor further comprises a counter electrode.

In a further embodiment the sensor further comprises a reference electrode.

In a further embodiment the electrochemical cell further comprises a potentiostat.

In one embodiment, one or more of the electrodes are composed of, or coated with, silver.

Presentation of the Insect Odorant Receptor Complex in the Bilayer of the Sensor Device The insect odorant receptor complex is preferably disposed in a membrane mimic as described above.

In a further embodiment, a first side of the artificial membrane contacts a first volume comprising a first medium.

In a further embodiment, a second side of the artificial membrane contacts a second volume comprising a second medium. The second medium may be the same as or different to the first medium.

Preferably, the first medium and/or the second medium is a fluid medium, preferably a liquid medium.

The first medium and/or the second medium may be a hydrophilic medium, preferably an aqueous medium.

Alternatively, the first medium and/or the second medium may be a hydrophobic medium. In this alternative configuration, hydrophobic groups of the amphipathic molecules of the membrane bilayer are in contact with the media.

In a further embodiment, the first medium and/or the second medium comprise ions in solution, preferably ions in aqueous solution; preferably metal ions; preferably a first or second group metal ion. Protons ($H^+$), and $K^+$, $Na^+$, $Ca^{2+}$ ions are preferred. The ions in the first medium and the second medium may be the same or different, if present in both.

In a further embodiment, the first volume and/or the second volume comprise a polymer network, which may or may not be in direct contact with the bilayer. Preferably, the polymer network comprises or consists of a hydrogel.

In a further embodiment, the first volume comprises a droplet of the first medium which is at least 100 nm in diameter, preferably at least 200 nm in diameter, and/or the second volume comprises a droplet of the second medium which is at least 100 nm in diameter, preferably at least 200 nm in diameter.

In a further embodiment, the first volume and/or the second volume comprises a layer of amphipathic molecules surrounding the first medium or the second medium respectively. The first medium and/or the second medium need not be wholly surrounded.

In a further embodiment, the layer of amphipathic molecules may cover all or part of first and/or second volume. The layer of amphipathic molecules is typically a monolayer.

In preferred embodiments, the artificial bilayer may therefore be a droplet interface bilayer formed where the layer of amphipathic molecules surrounding the first and second volumes respectively are in contact. In other embodiments it may be a planar bilayer.

Preferably the membrane comprises amphipathic molecules such as lipid molecules. Preferably, the amphipathic molecules comprise phospholipid molecules. Preferred lipid molecules include DPhPC (1,2-diphytanoyl-sn-glycero-3-phosphocholine), POPS (1-palmitoyl-2-oleoyl-sn-glycero-3-phospho-L-serine), POPC (1-palmitoyl-2-oleoyl-glycero-3-phosphocholine), POPE (1-palmitoyl-2-oleoyl-snglycero-3-phosphoethanolamine), Cholesterol, Polyethylene glycol (PEG) lipids, POPG (1-palmitoyl-2-oleoyl-sn-glycero-3-phospho-(1'-rac-glycerol)), and salts thereof.

In a further embodiment, the membrane and, where present, the first volume and, where present, the second volume, are disposed in a hydrophobic medium, preferably wherein the hydrophobic medium comprises an oil.

In a further embodiment, the OrX and Orco are ionotrophic membrane proteins. The OrX and Orco proteins together form a complex. In some embodiments, the complex forms in the presence of the analyte.

Detection of Analyte with the Bilayer Sensor

In a further embodiment the insect odorant receptor complex forms an ion channel sensitive to the presence or otherwise of the analyte.

Preferably detection is specific for the analyte.

In a further embodiment, binding of the analyte activates the insect odorant receptor complex, causing a flow of ions across the membrane.

Preferably, the first electrode is in electrical contact with the first side of the membrane and the second electrode is in electrical contact with the second side of the membrane.

In a further embodiment, the sensor comprises a control system which is configured to measure an electrical characteristic, for example a flow of current, between the first and second electrodes.

In a further embodiment, the sensor further comprises an output system, wherein the indication system is configured to indicate that an analyte has been detected. Detection of an analyte may be indicated by any system known in the art, such as an alarm, an electrical signal, a graphical user interface or so forth. The indication system may also indicate the presence or absence of an analyte, the concentration of analyte, etc.

Sensing Method

In a further embodiment there is provided a method for detecting an analyte using a sensor as disclosed herein, wherein the sensor comprises:

a) a membrane which comprises amphipathic molecules, an Orx protein and an Orco protein;

b) a first substrate comprising a first electrode disposed at the first side of the membrane; and c) a second substrate comprising a second electrode disposed at the second side of the membrane;

wherein the method comprises:

a) contacting the analyte with the membrane; and b) obtaining an electrical measurement across the first and second electrodes.

Contact of the analyte with the insect odorant receptor complex, causing a flow of ions through an ion channel formed by the insect odorant receptor complex. Without being bound by theory, it is believed that the permeability of this channel to ions alters when an analyte interacts with OrX. The flow of ions between the first and second electrodes through the ion channel allows current to flow between the electrodes.

Preferably, the method comprises detecting a current flowing between the first and second electrodes. The level of current indicates the state of the ion channel and may indicate the binding or the kind of analyte bound. Preferably, a change in current indicates the binding of an analyte.

A change in current can be measured as a change over time. Such measurement may involve a series of discrete measurements, or continuous measurement. Taking a plurality of measurements or continuous measurements enables the detection of a more complex signal, which can be unraveled to indicate, for example, whether multiple analytes are present.

In further embodiments the method comprising optional further steps including i) determining whether an analyte is present, ii) determining which analyte is present, and/or iii) determining concentration of analyte.

In a further embodiment, the method applying a potential between the first and second electrodes. In some embodiments, the potential may be zero.

In a further embodiment, the method comprises detecting the flow of ions across the membrane through a complex formed by the Orco and OrX proteins.

In a further embodiment, the method comprises contacting the analyte with the membrane comprises forming a complex comprising the Orco protein, the Orx protein and the analyte.

In a further embodiment, the method comprises detecting an interaction between the analyte and the Orco and Orx proteins.

In a further embodiment, a first side of the membrane contacts a first volume comprising a first medium and the method comprises introducing the analyte into the first volume.

In a further embodiment, the sensor is a sensor as defined herein and wherein the method comprises obtaining a composite electrical measurement across each of the first electrodes and the second electrode, preferably detecting a composite current flowing between the second electrode and each of the first electrodes.

Surface Plasmon Resonance (SPR) Sensor Device

The use of Surface Plasmon Resonance (SPR) for the detection of small soluble analytes is well known (see e.g. "Advances in Biosensors—Vol 5. 2003" Ed. Bansi D. Malhotra & Anthony P. F. Turner, Pub. Jai Press Ltd, London).

A surface plasmon (SP) refers to coherent electron oscillation that propagates along an interface between a dielectric (e.g. silica glass) and a metal (e.g. silver or gold) together with an electromagnetic wave, e.g., light. Under certain conditions (defined by of wavelength, polarization and/or incidence angle), free electrons at the surface of the metal absorb incident light photons and convert them into surface plasmon waves. A resonance condition, referred to as surface plasmon resonance (SPR), can be established when the frequency of light photons matches the natural frequency of surface electrons oscillating against the restoring force of positive nuclei of the metal.

The surface plasma resonance condition can be used to detect the binding of an analyte to an insect odorant receptor complex coupled to the metallic surface, by measuring the angle of reflection minimum (or absorption maximum) of light. For example, binding of the analyte to the insect odorant receptor complex may cause perturbations at the metal surface, which can in turn induce a modification of the SPR condition. Such a modification can be measured as a change in reflectivity of the substrate, and forms the basis for some SPR-based measurement techniques that are adapted for measuring the presence of a wide variety of target molecules. In one embodiment of the sensor device, the substrate is an inert metal surface on a glass prism. Preferably, the metal surface is a metallic layer of silver or gold. More preferably, the metal layer has a thickness of approximately 50 nm.

Electrical Characteristic

In one embodiment the electrical characteristic is surface plasmon resonance.

Presentation of the Insect Odorant Receptor Complex in the SPR Sensor Device

The insect odorant receptor complex may be present in a membrane mimic as described above.

In one embodiment the insect odorant receptor complex is present in a liposome, for example an artificial liposome, or a nanodisc.

In a further embodiment the insect odorant receptor complex is present in a lipid bilayer, for example an artificial lipid bilayer.

In a preferred embodiment the insect odorant receptor complex is present in a liposome.

Coupling of the Insect Odorant Receptor Complex to Metallic Layer in the SPR Sensor Device In one embodiment the insect odorant receptor complex is coupled to the metal surface.

In a further embodiment the insect odorant receptor complex is coupled directly to the metal surface via a N-terminal cysteine residue.

Detection of Analyte with the SPR Sensor

In a further embodiment the sensor is capable of detecting binding of an analyte to the insect OrX in the insect odorant receptor complex.

In a further embodiment the sensor is capable of detecting, in an environment, the presence of an analyte that binds to the insect OrX.

Preferably detection is specific for the analyte.

In a further embodiment the SPR sensor comprises:

(a) a metal surface to which the insect odorant receptor complex capable of binding the analyte is bound, (b) a light source excitation beam for direction at the metal surface, (c) at least one detector capable of detecting light from the light beam which is internally reflected from the metal surface.

In a further embodiment, the SPR sensor optionally includes a beam modifying means whereby the excitation beam is influenced in a controlled manner whereby the level of light emitted from the sensor surface is substantially enhanced.

The beam modifying means may be operable so as to displace the excitation beam over an angular range, relative to the metal surface. The excitation displacement means may comprise a beam-reflecting mirror and means for vibrating the mirror. The excitation beam may comprise a linear-beam, a fan-shaped beam or a wedge-shaped beam.

Alternatively, the beam modifying means may be operable so as to adjust the wavelength of the excitation beam.

In a further embodiment binding of the analyte to the insect OrX causes a change in the refractive index of the sensor. Preferably this change is detected by measuring the shift in the surface plasmon resonance angle or resonance wavelength.

Detector Component

In a further embodiment the sensor comprises a detector component.

In a further embodiment the detector component detects, or measures time-variation of the resonance wavelength of the excitation beam (at fixed resonant angle) or time-shifting of the resonance angle at a fixed wavelength.

Sensitivity of Detection

As discussed above, the sensor of the invention works surprising well. The applicants have shown that the sensor device of the invention is considerably more sensitive than any of known assay involving use of insect odorant receptors.

In one embodiment the sensor can detect the presence of the analyte at a concentration of less than $1 \times 10^{-3}$M, preferably less than $1 \times 10^{-3}$M, more preferably less than $1 \times 10^{-4}$M, more preferably less than $1 \times 10^{-5}$M, more preferably less than $1 \times 10^{-6}$M, more preferably less than $1 \times 10^{-7}$M, more preferably less than $1 \times 10^{-8}$M, more preferably less than $1 \times 10^{-9}$M, more preferably less than $1 \times 10^{-10}$M, more preferably less than $1 \times 10^{11}$M, more preferably less than $1 \times 10^{-12}$M, more preferably less than $1 \times 10^{-13}$M, more preferably less than $1 \times 10^{-14}$M, more preferably less than $1 \times 10^{-15}$M, more preferably less than $1 \times 10^{-16}$M, more preferably less than $1 \times 10^{-17}$M, more preferably less than $1 \times 10^{-18}$M.

Dynamic Range

In one embodiment the sensor has a dynamic range for detection of analyte of at least 2, preferably at least 3, more preferably at least 4, more preferably at least 5, more preferably at least 6, more preferably at least 7, more preferably at least 8, more preferably at least 9, more preferably at least 10 orders of magnitude of analyte concentration.

Other Advantages of the Sensor of the Invention

The sensor or the invention provides numerous potential advantages over previously known insect OR based systems/assays in terms of convenience, portability, stability, rapid detection, sensitivity, and ease of measurement.

Analyte Medium

The analyte may be in a gaseous or liquid medium.

Optional Capture Component

The sensor device may additionally comprise a component to capture the analyte and present the analyte to the receptor. This component may be useful for capturing volatile analytes in some embodiments for presentation to the OrX. This may involve use of microchannels to handle the target VOC either in a liquid or gaseous phase ([29]). Microfluidic systems have been designed to deliver target molecules to sensor surfaces in the liquid ([30-31]) and the gaseous phase ([31-33]).

Multiplexing

The invention contemplates multiplex approaches using multiple different OrX proteins in the insect odorant receptor complexes. In this way, the user may construct a multiplexed device that is sensitive to multiple analytes. Such multiplexed devices may include tens, hundreds, or even thousands of sensors as herein described. A multiplex device may also include two or more sensors that are coupled to the same insect odorant receptor complex so as to introduce a "double-check" into the device.

The invention also contemplates use of chips with multiple sensor substrates each comprising a different or the same receptor in the insect odorant receptor complex. The sensor device component of the invention may be such a chip.

Method Using Sensor Device of the Invention

The invention provides methods of use of the sensor device of the invention to detect an analyte, and/or the presence of analyte in an environment, as described above.

Controls and Calibration

The user may compare the electrical characteristic of the device to a corresponding electrical characteristic measured when the device is exposed to a control, a known analyte, or both. The user may also generate an estimate of the presence of one or more analytes in the sample. This may be accomplished by comparing the electrical characteristic observed in a sample to a calibration curve of that electrical characteristic that corresponds to data points gathered from a control or standard having a known amount of an analyte of interest. In this way, the user may estimate the concentration of an analyte present in a sample to which the device has been contacted.

The user may construct a library of one or more electrical characteristics of the device that correspond to the device's exposure to one or more known analytes. For example, a user may construct a library of results that represents the electrical characteristic observed when a device is exposed to various concentrations of analytes.

Method of Manufacturing the Sensor Device of the Invention

Sensor Device

In a further aspect the invention provides a method of manufacturing a sensor device the method including the step of establishing electrical communication between an insect odorant receptor complex and the substrate of the sensor device, wherein the sensor device is configured to detect a change in an electrical characteristic of the substrate.

In one embodiment the method includes the step of coupling of the insect odorant receptor complex to the substrate.

In one embodiment the insect odorant receptor complex is coupled to the substrate before the insect odorant receptor complex coupled substrate is assembled in the sensor device.

Preferably the components, coupling and functionality of the sensor is/are as described herein.

Sensor Component

In a further aspect the invention provides a method for producing a component for a sensor device, the component comprising an insect odorant receptor complex in electrical communication with a substrate as herein defined. The method comprises establishing electrical communication between the insect odorant receptor complex and the substrate, as described herein. This component is useful for adding to a sensor device according to the invention.

In a further embodiment the invention provides a method for producing a sensor device, the method comprising adding the component to other components, as herein described, to produce a sensor device according to the invention.

Method of Manufacturing the Eis Sensor Device of the Invention

In one embodiment the substrate is the working electrode of an electrochemical cell as described herein.

Thus in one embodiment method comprises the step of establishing electrical communication between an insect odorant receptor complex and the working electrode of an electrochemical cell, wherein electrochemical cell is configured to detect a change in the electrochemical impedance of the working electrode thus forming the sensor device.

By way of example a suitable method for manufacture of the EIS device of the invention is described in Example section. This example is not intended to limit the scope of the invention.

Method of Manufacturing the CNT-FET Sensor Device of the Invention

In one embodiment the substrate is the channel of a CNT-FET apparatus as described herein.

Thus in one embodiment method comprises the step of establishing electrical communication between an insect odorant receptor complex and the channel of a CNT-FET apparatus, wherein the channel of a CNT-FET apparatus is configured to detect a change in the source-gain current of the CNT-FET apparatus thus forming the sensor device.

By way of example a suitable method for manufacture of the CNT-FET device of the invention is described in Example section. This example is not intended to limit the scope of the invention.

Method of Manufacturing the Graphene FET (GFET) Sensor Device of the Invention

In one embodiment the substrate is the channel of a GFET apparatus as described herein.

Thus in one embodiment method comprises the step of establishing electrical communication between an insect odorant receptor complex and the channel of a GFET apparatus, wherein the channel of a GFET apparatus is configured to detect a change in the source-gain current of the GFET apparatus thus forming the sensor device.

By way of example a suitable method for manufacture of the GFET device of the invention is described in Example section. This example is not intended to limit the scope of the invention.

Method of Manufacturing the QCM Sensor Device of the Invention

In one embodiment the substrate is the resonator component of a quartz crystal microbalance (QCM) as described herein.

Thus in one embodiment method comprises the step of establishing electrical communication between an insect odorant receptor complex and the resonator component of a quartz crystal microbalance (QCM), wherein QCM is configured to detect a change in the resonance frequency of oscillations induced by an alternating electric field applied to the resonator component, thus forming the sensor device.

By way of example a suitable method for manufacture of the QCM device of the invention is described in Example section. This example is not intended to limit the scope of the invention.

Method of Manufacturing the Bilayer Sensor Device of the Invention

In one embodiment the substrate is the working electrode of an electrochemical cell as described herein.

Thus in one embodiment method comprises the step of establishing electrical communication between an insect odorant receptor complex and the working electrode of an electrochemical cell, wherein the electrochemical cell is configured to detect a change in an electrical characteristic between the working electrode and a second electrode, thus forming the sensor device.

By way of example a suitable method for manufacture of the bilayer device of the invention is described in Example section. This example is not intended to limit the scope of the invention.

Method of Manufacturing the SPR Sensor Device of the Invention

In one embodiment the substrate is an inert metal surface on a prism as described herein.

Thus in one embodiment the method comprises the step of coupling an insect odorant receptor complex to the metal surface, wherein the device is configured to detect a change in the refractive index of the substrate, thus forming the sensor device.

By way of example a suitable method for manufacture of the SPR device of the invention is described in Example section. This example is not intended to limit the scope of the invention.

General Definitions and Methods

OrX and Orco Proteins/Polypeptides and Fragments

The term "polypeptide", as used herein, encompasses amino acid chains of any length but preferably at least 5 amino acids, including full-length proteins, in which amino acid residues are linked by covalent peptide bonds. Polypeptides for use in the present invention are preferably produced partially or wholly using recombinant or synthetic techniques.

A "fragment" of a polypeptide is a subsequence of the polypeptide that preferably performs a function of and/or provides three dimensional structure of the polypeptide.

A "functional fragment" of an OrX polypeptide as used herein is a subsequence of an OrX that can perform the function of binding an analyte, and which upon binding can result in a conformational change in the insect odorant receptor complex it forms part of, wherein the conformational change results in a change in an electrical property of a substrate to which the functional fragment is bound. In one embodiment the conformational change is opening of an ion channel in the insect odorant receptor complex.

A "functional fragment" of an Orco polypeptide as used herein is a subsequence of an Orco that can perform the function of insect odorant co-receptor, and undergoing a conformational change in upon analyte binding to an OrX in the insect odorant receptor complex, wherein the conformational change results in a change in an electrical property of a substrate to which the functional fragment is bound. In one embodiment the conformational change is opening of an ion channel in the insect odorant receptor complex.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

Variants

A variant of an OrX or Orco polypeptide refers to polypeptide sequences different from the specifically identified sequences, wherein one or more amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the identified polypeptides possess biological activities that are the same or similar to those of the inventive polypeptides or polypeptides.

Preferably an OrX polypeptide variant can perform the function of binding an analyte, and which upon binding can result in a conformational change in the insect odorant receptor complex it forms part of, wherein the conformational change results in a change in an electrical property of a substrate to which the functional fragment is bound. In one embodiment the conformational change is opening of an ion channel in the insect odorant receptor complex.

Preferably a OrX polypeptide variant can perform the function of insect odorant co-receptor, and undergoing a conformational change in upon analyte binding to an OrX in the insect odorant receptor complex, wherein the conformational change results in a change in an electrical property of a substrate to which the functional fragment is bound. In one embodiment the conformational change is opening of an ion channel in the insect odorant receptor complex.

Variant polypeptide sequences preferably exhibit at least 70%, more preferably at least 80%, more preferably at least 90%, more preferably at least 95%, more preferably at least 96%, more preferably at least 97%, more preferably at least 98%, and most preferably at least 99% identity to a sequences of the present invention. Identity is preferably calculated over the entire length of an identified polypeptide.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp:// ftp.ncbi.nih.gov/blast/.

Polypeptide sequence identity may also be calculated over the entire length of the overlap between a candidate and subject polynucleotide sequences using global sequence alignment programs. EMBOSS-needle (available at http:/ www.ebi.ac.uk/emboss/align/) and GAP (Huang, X. (1994) On Global Sequence Alignment. Computer Applications in the Biosciences 10, 227-235) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem.

Sci. 23, 403-405) Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Methods for Producing Polypeptides

The polypeptides used in the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco California, or automated synthesis, for example using an Applied Biosystems 431A Peptide Synthesizer (Foster City, California). Mutated forms of the polypeptides may also be produced during such syntheses.

Preferably, the polypeptides and variant polypeptides, are expressed recombinantly in suitable host cells and separated from the cells as discussed below. Polynucleotides, for expressing the polypeptides, can be conveniently synthesised by methods well known to those skilled in the art. The polynucleotide sequences may be naturally occurring, or may be adapted from naturally occurring sequences, for example through use of preferred codon usage for the cell in which the sequence is recombinantly expressed.

Methods for Producing Constructs and Vectors

The genetic constructs for use in invention comprise one or more polynucleotide sequences encoding OrX or Orco polypeptides for use in the invention, and may be useful for transforming, for example, bacterial, fungal, insect, mammalian or plant organisms.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors Host cells comprising polynucleotides are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides for use in the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE FIGURES

The present invention will be better understood with reference to the accompanying non-limiting drawings in which.

Figure 1:
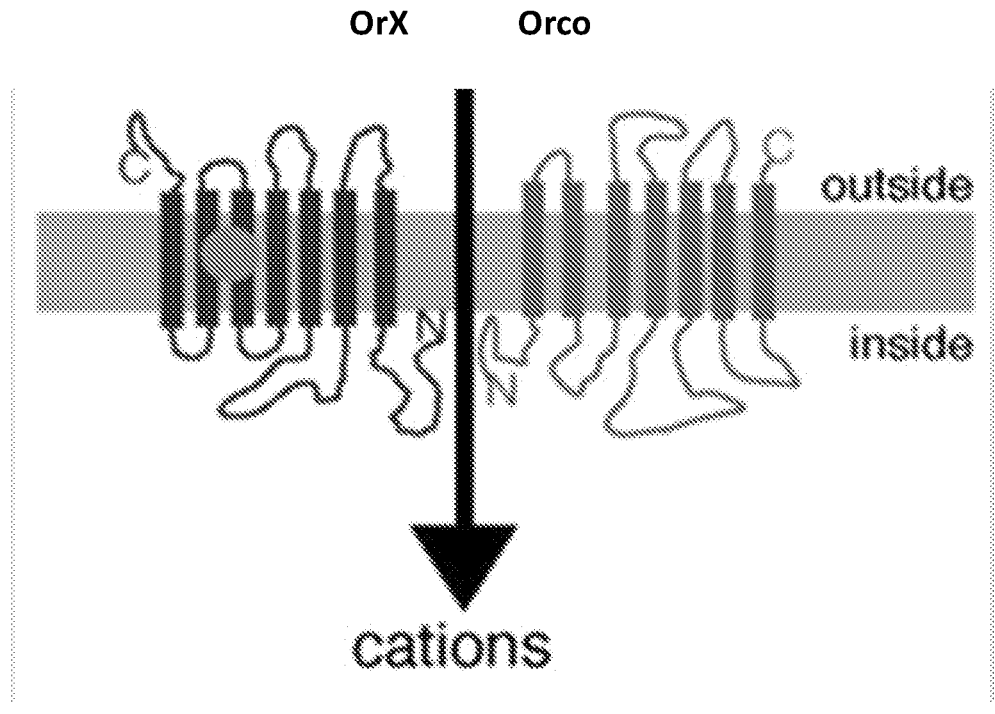
FIG. 1. Schematic representation of the insect OR membrane complex, comprised of an odorant binding OrX subunit and an Orco subunit to produce a ligand-gated nonselective cation channel. The orange circle represents the bound odorant.

EXAMPLE 1—EXEMPLIFICATION OF THE
SENSOR OF THE INVENTION WITH
ELECTRICAL Impedance Spectroscopy (EIS)

Previous unpublished data produced by the present inventors (resulting in the invention described in PCT/IB2017/058181) has shown that surprisingly an OrX can be used alone in an electronic sensor device, that is capable of detecting specific binding of analyte with significant improvement over insect OR-based sensor systems of the prior art.

The data of the present application shows that inclusion of Orco in addition to OrX surprisingly provides further significant improvements over both insect OR-based sensor systems of the prior art, and the OrX (alone)-based electronic sensor devices previously produced by the applicants forming the subject invention of PCT/IB2017/058181.

Summary

The applicants demonstrate the convenient, sensitive sensor device using insect OrX sequences. Two OrX receptors (Or10a, Or22a)[19] were each embedded on their own or with Orco in liposomes[28] and functionalized on gold electrodes for EIS measurements under further optimized experimental conditions. Each of the OrX functionalized gold electrodes has shown a clear electronic response to its target ligands (Or10a to methyl salicylate, Or22a to methyl hexanoate)[20] starting at fM concentrations. The presence of Orco in the liposomes has an additive, or amplifying, effect on the OrX response, increasing the maximum response level and increasing the sensitivity of the OrX for its target ligand. The specificity of the binding is verified by testing each OrX liposomes and OrX/Orco liposomes functionalized electrode response to non-responding ligands. To further ensure the specificity the response of empty liposomes functionalized gold electrodes to the target ligands were also tested.

1.0 Experimental Methods 1.1 Materials 6-mercaptohexanoic acid (MHA), N-hydroxysuccinimide (NHS), 1-ethyl-3-(3-dimethylaminopropyl)-carbodiimide) (EDC), phosphate buffer saline (PBS) tablets, methyl salicylate, and methyl hexanoate were obtained from Sigma-Aldrich. 1.6 mm diameter gold (Au) disk electrode, coiled platinum (Pt) wire electrode and leakless silver/silver chloride (Ag/AgCl) electrode were purchased from BASi for electrochemical measurements.

1.2 Preparation of Purified OrX and Orco Subunits

The purification procedure is a variation on the one detailed in Carraher et al. 2013[28]. To his-tag affinity purify protein from baculovirus-infected Sf9 cells, 500 mL at $2\times10^6$ mL$^{-1}$ were infected with baculovirus at an MOI of 0.1, and incubated at 27° C. for 72 h. The cell pellet was collected by centrifugation at 3800 g for 10 min at room temperature and then resuspended in 40 mL of resuspension buffer A (20 mM Tris/HCl pH 7.5, 100 mM NaCl, 1× protease inhibitor cocktail (Roche Diagnostics GmbH, Germany)), with 25 U/mL Benzonase, then lysed by two passes on an Emulsiflex C5 emulsifier (Avestin, Germany) at 10,000-15,000 psi. The sample was then centrifuged at 1000 g for 5 min to remove whole cells and nuclei. The supernatant was removed and spun at 100,000 g for 1 h at 4° C. The membrane pellet was resuspended in 40 mL of buffer A with 1% w/v detergent (Fos-Choline 14 (FC14)) and rotated for 1 h at room temperature at 10 rpm. The sample was then centrifuged at 100,000 g for 1 h at 18° C. The supernatant was removed and loaded onto a 1 mL NiNTA column (GE Healthcare). The column was washed in ten column volumes of buffer B (20 mM Tris/HCl pH 7.5, 3.6 mM FC-14) with 300 mM NaCl and 20 mM imidazole, and a further ten column volumes of buffer B with 100 mM NaCl and 50 mM imidazole. Protein was eluted with four column volumes buffer B with 100 mM NaCl and 500 mM imidazole. Purity was assessed on Coomassie stained SDS-PAGE gels and Western blotting.

Purification was completed with a final size exclusion chromatography (SEC) step. The elution fractions from the NiNTA purification were pooled and centrifuged at 20,000 g for 5 min to remove aggregates and contaminants. Then 5 mL of sample was injected onto a Superdex 200 16/60 column (GE Healthcare) attached to an Akta-Pure chromatography system (GE Healthcare). The sample was run at 1 mL/min in buffer B with 100 mM NaCl, and 2 mL fractions were collected and concentrated using a 100 kDa MWCO Vivaspin2 filter unit (Sartorius, Goettingen Germany) and stored at –80° C.

1.3 Preparation of Liposome Associated OR Subunits

Liposomes were prepared using a phospholipid solution produced by evaporating solutions containing: phosphatidylethanolamine (PE), phosphatidylserine (PS), phosphatidylcholine (PC), and cholesterol (CH) at a molar ratio of 5:3:3:1 in a small glass tube under a stream of $N_2$ gas, then desiccating under vacuum for 1 h.

These lipids were resuspended in 1 mL of rehydration buffer (10 mM HEPES pH 7.5, 300 mM NaCl) by vortexing for 5 min followed by sonicating on a Microson ultrasonic cell disrupter (Medisonic, USA) five times at 20% power for 10-20 s, placing the sample on ice between each sonication step for 1 min. To promote the formation of liposomes, 10 freeze/thaw steps were performed by transferring the tube from liquid nitrogen to a 40° C. water bath.

Liposomes were then sized by passing the lipid solution 11 times through a 100-nm polycarbonate membrane using an Avestin LiposoFAST extruder unit (Avestin, Germany). Glycerol was added at 10% of the final volume and aliquots at 10 mg/mL were snap frozen in liquid nitrogen and stored at –80° C.

Purified OrX and Orco subunits[19] were reconstituted into the synthetic liposomes in a similar manner to the protocol of Geertsma et al. (2008)[3].

Prior to their use, liposomes were defrosted on ice and then destabilized by incubating with 0.2% CHAPS for 15 min at room temperature. Then 200 μg of purified odorant receptor[28] was added to 1 mg of liposomes and rotated at 10 rpm for 1 h at room temperature. Excess detergent was removed by four additions of 25 mg of Bio-Beads SM-2 (Bio-Rad, USA) and incubation at 4° C. for 30 min, 2 h, overnight and a further 2 h respectively. The Bio-Beads were removed after each incubation period. The OrX or OrX/Orco integrated liposomes were pelleted by centrifugation at 100,000 g for 1 h, and were resuspended in 500 μL of rehydration buffer. Integration of OrXs and Orco into liposomes was assessed by density gradient ultracentrifugation (DGU) using Accudenz (Accurate Chemical & Scientific Corporation, USA). The integrated liposomes were brought to 40% Accudenz by the addition of an equal volume of 80% Accudenz solution, placed at the bottom of an ultra-centrifugation tube, and overlaid with 30% Accudenz solution, and DGU buffer (25 mM HEPES pH 7.5, 100 mM NaCl, 10% glycerol). The sample was then centrifuged at 100,000 g for 4 h at 4° C. Liposomes will float to the top of the gradient after Accudenz DGU due to their low density.

1.4 Electrode Preparation

Gold disk electrodes (1.6 mm diameter) were polished on alumina polishing pad with polishing alumina slurry for one minute for each electrode. The polished electrodes were rinsed with deionised water (Milli-Q, 18.2 MΩ cm) followed by ultrasonication in ethanol (LR grade) and deionised water until the residual alumina slurry was completely removed from the electrodes. Chronoamperometry at –1.4 V was applied onto all of the ultrasonicated electrodes to desorb the SAMs of the thiol present on the surface of the electrodes for 30 seconds using 0.1 M sodium hydroxide (NaOH) electrolyte solution in a three terminal electrochemical cell, Ag/AgCl (3 M NaCl, 0.209 V vs. SHE) reference electrode, coiled platinum wire as a counter electrode and gold disk as a working electrode, using a PalmSens3 potentiostat. Then, the electrodes were again rinsed with deionised water and ultrasonicated in ethanol and deionised water consecutively. Finally, cyclic voltammetry was performed for 10 cycles between –0.2 and 1.6 V, at a scan rate of 50 mV/s in 0.5 M sulphuric acid ($H_2SO_4$) solution to remove any other impurities (a three electrode cell, Ag/AgCl (in 3 M NaCl, 0.209 V vs. SHE) reference electrode, coiled platinum wire as a counter electrode and gold disk as a working electrode).

1.5 Self-Assembled Mono Layer (SAM) Preparation and Activation 2 mM MHA was prepared by dissolving 1.36 μl of MHA in 5 ml ethanol (AR grade). The cleaned electrodes were immersed into MHA solution and incubated overnight. The next day, all the electrodes were washed with ethanol and deionised water thoroughly in order to remove the unreacted acid. A 2:1 mol:mol ratio of EDC:NHS (100 mM EDC, 50 mM NHS) was prepared in 2 ml PBS (pH=6.5) solution. Then, the electrodes were covered in 100 μl of this solution at 28° C. for an hour to activate the carboxylic (COOH) groups of the MHA.

1.6 OrX and OrX/Orco Associated Liposomes Immobilisation on Electrodes

PBS solution was prepared by immersing one tablet of PBS in 200 ml of milli-Q water (according to manufacturers instructions) and filtered using 0.2-μm syringe filter. The pH of the prepared buffer solution was measured with a pH meter. OrX liposomes or OrX/Orco liposomes were diluted 100 fold in PBS buffer solution (pH=7.4) and the COOH-activated electrodes were incubated in that buffer solution at room temperature for one hour. Then, the electrodes were washed extensively with PBS buffer solution to wash out any unbound liposomes.

1.7 Target Odorant Solution Preparation and Incubation

PBS (pH=7.4) was used as an electrolyte to conduct electrochemical measurements. PBS buffer was degassed for about 30 minutes prior to electrochemical measurements. Odorant solutions of concentration ranging from 1 aM to 1 μM were prepared by sequential dilution in PBS solution containing 1% DMSO. OR immobilized electrodes were incubated in relevant odorant solution for ~30 minutes each and washed gently with PBS before EIS measurements.

1.8 Electrochemical Impedance Spectroscopy (EIS) Measurements

EIS measurements were done in a 3 electrode cell containing Ag/AgCl (3 M NaCl, 0.209 V vs. SHE) reference electrode, coiled platinum wire as a counter electrode and the gold disk as a working electrode at a fixed voltage of −0.7 using PalmSens potentiostat. Degassed PBS was used as an electrolyte.

2.0 Results

Figure 2:
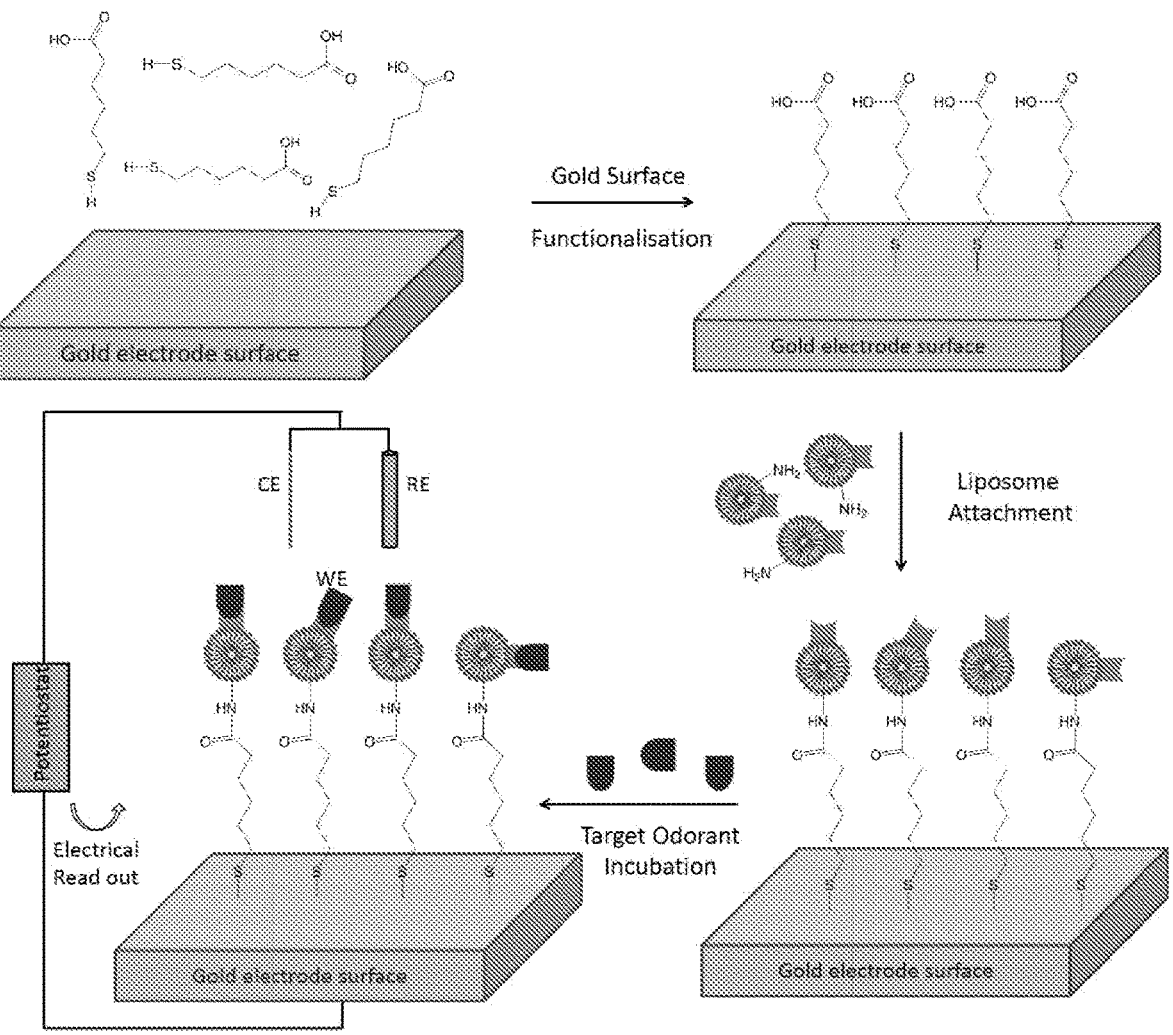
FIG. 2. Schematic representation of the EIS sensor preparation starting with electrode cleaning, followed by SAM formation and completed with the covalent attachment of liposomes onto the SAM layer. Electrochemical read-out is obtained from EIS measurements carried out in three terminal electrochemical set-ups. Circles with blue shape represent liposome-integrated insect OrXs or OrX/Orco complexes, and red shapes represent VOC ligands.

Insect olfactory receptors are comprised of OrX subunits in a complex with Orco subunits in cell membranes to produce an ion channel (FIG. 1)[17]. In this study the authors investigate the effect of Orco on the ligand binding activity of OrXs embedded in liposomes. The experimental procedure consisting of the deposition of self-assembled monolayers (SAMs) of 6-mercaptohexanoic acid (MHA), activation of —COOH end groups with N-hydroxysuccinimide/ 1-ethyl-3-(3-dimethylaminopropyl)-carbodiimide) (NHS/ EDC) coupling, covalent attachment of ORs/liposomes and binding of the target odorant molecules as monitored by EIS, is presented in FIG. 2. The cleaned gold surface was incubated overnight with MHA to build SAMs with carboxylic acid end groups, as shown in the scheme. The —COOH end groups of the SAMs were further activated by exposing the gold surface to EDC/NHS solution to form N-hydroxysuccinimidyl ester, which can then link to the biomolecules. Finally, the electrode was incubated with OrX/ liposome solutions, allowing the vesicles to covalently attach to the gold surface.

Figure 3:
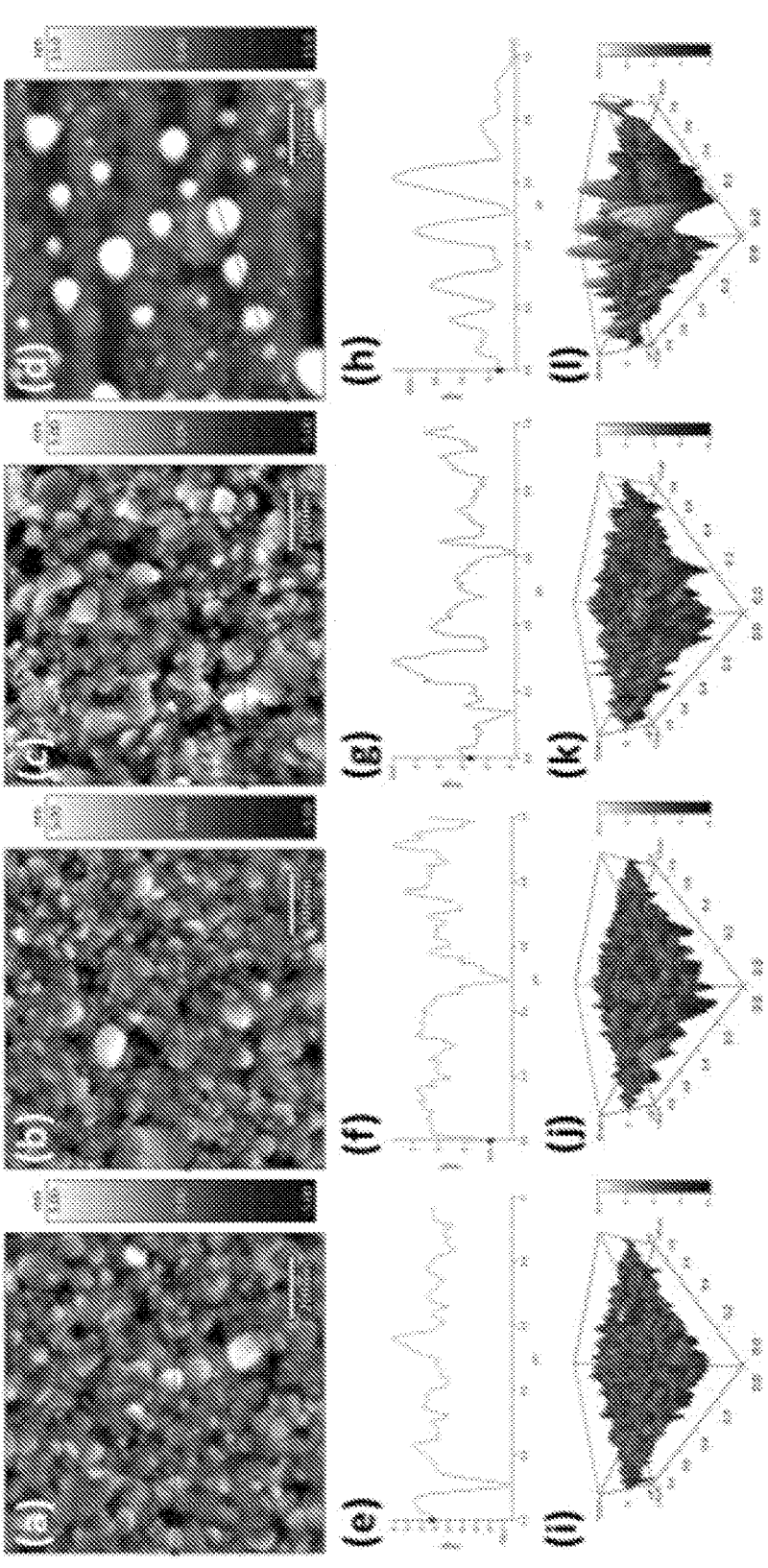
FIG. 3 shows AFM height images (a-d), roughness profile indicated by the marked line on height images (e-h), and 3D images (i-l) of bare, SAM modified, NHS-EDC coupled, and Or22a/liposomes immobilized gold surfaces, respectively.

The authors used atomic force microscopy (AFM) to verify that the liposomes can be immobilised on to gold surfaces. FIG. 3 shows that a change can be seen in surface morphology and roughness profile from bare gold surface to the OR associated liposomes immobilized surface. The bare gold surface (FIG. 3 (*a*)) shows densely packed flat gold nanocrystals of various sizes with surface roughness value of around 2 nm. After SAM modification (FIG. 3 (*b*)) and NHS/EDC activation of SAM modified gold surface (FIG. 3

(*c*)), negligible changes in surface morphology were observed. When OrX liposomes were introduced to the EDC/NHS activated SAM modified gold surface (FIG. 3 (*d*)), the change in surface morphology was noticeable showing circular shaped liposomes immobilised on the surface. Variable sized round shaped liposomes were seen all over the surface in their native form i.e. no rupture or bilayer formation was observed which also indicates ORs are well retained in the membranes of liposomes. The large increase in surface roughness values (>30 nm) also demonstrates that ORs containing liposomes were successfully attached to the NHS/EDC activated SAM modified gold surface.

Figure 4:
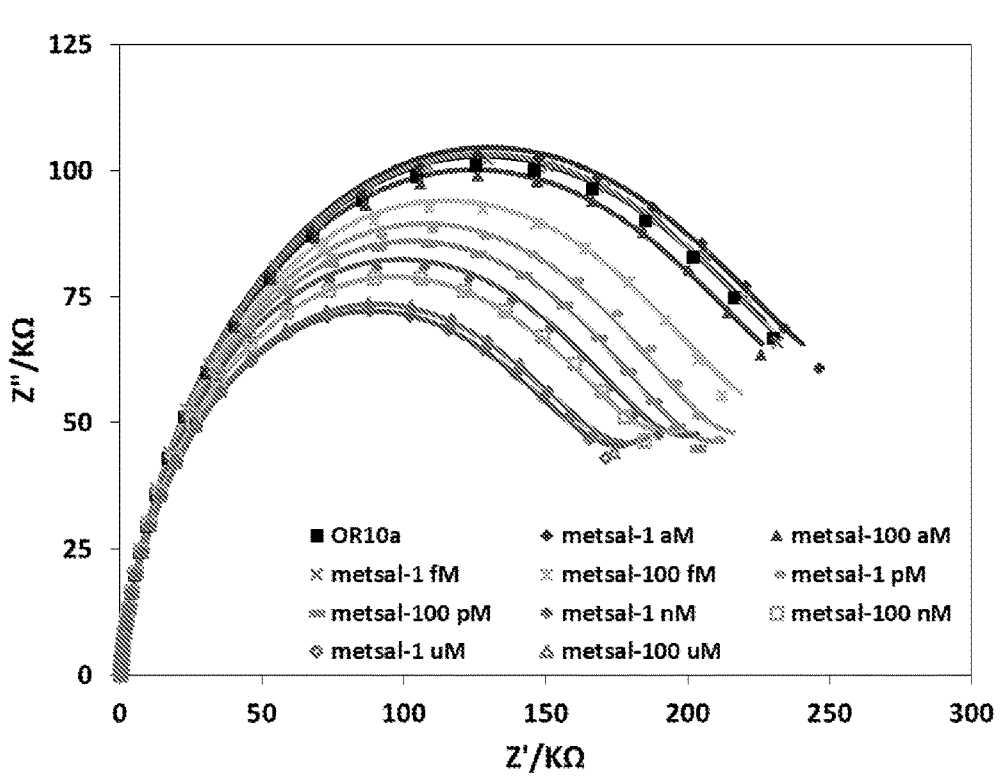
FIG. 4. (A) Impedance evolution of an Or10a liposomes functionalised electrode versus the target ligand methyl salicylate (metsal) with a concentration range from 1 aM to 100 μM. Experimental data are presented as symbols and the equivalent circuit fitting curves as solid lines. (B) Dose response curve for gold electrodes functionalized with Or10a liposomes in response to the target ligand methyl salicylate, and control ligand methyl hexanoate. The target and control ligand binding measurements were also performed with gold electrodes functionalised with empty liposomes. Error bars were generated using standard deviation using four repeats.
Figure 4:
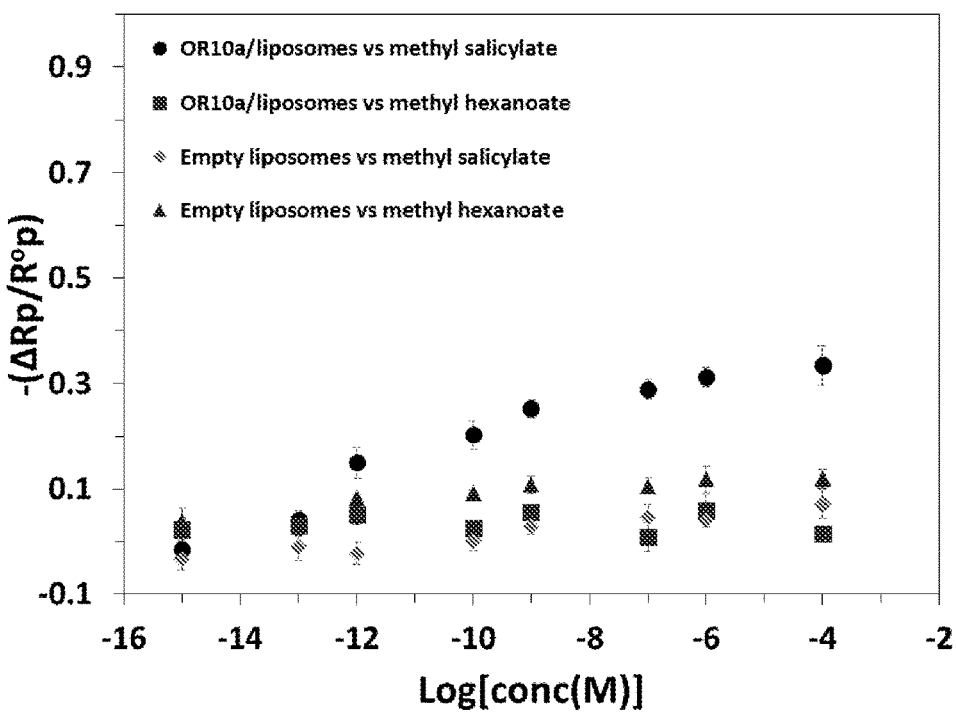

EIS measurements were performed on gold electrodes functionalised with OrX liposomes (either Or10a or Or22a), OrX/Orco liposomes, or empty liposomes prior to and after target ligand or control ligand incubation with increasing concentrations (1 aM to 100 μM). Dose response curves were obtained by defining sensor response as $-(\Delta R_p/R^o_p)$ versus log[C(Ligand)]. FIG. 4*a* presents the EIS response in terms of Nyquist plot for the Or10a liposome functionalized sensors when exposed to a solution containing one of the known target ligands of Or10a, methyl salicylate, at various concentrations. The Nyquist plot showed decrease in EIS response after the addition of increasing concentration of methyl salicylate. The dose response curve (FIG. 4*b*) was obtained by plotting the change in polarization resistance $-(\Delta R_p/R^o_p)$ versus log[conc(Ligand)], as the sensor response. Here, $R_p$ is the polarization resistance after Or10a liposome—target interaction and $R^o_p$ is the polarization resistance before Or10a liposome—target interaction. The Or10a liposomes sensor responded to methyl salicylate with the limit of detection (LOD) of 0.1 μM and with negligible response to the control ligand methyl hexanoate control. The sensor functionalized with the empty liposomes showed negligible responses towards the positive and negative ligand suggesting OR is the key element to detect the odorants.

Figure 5:
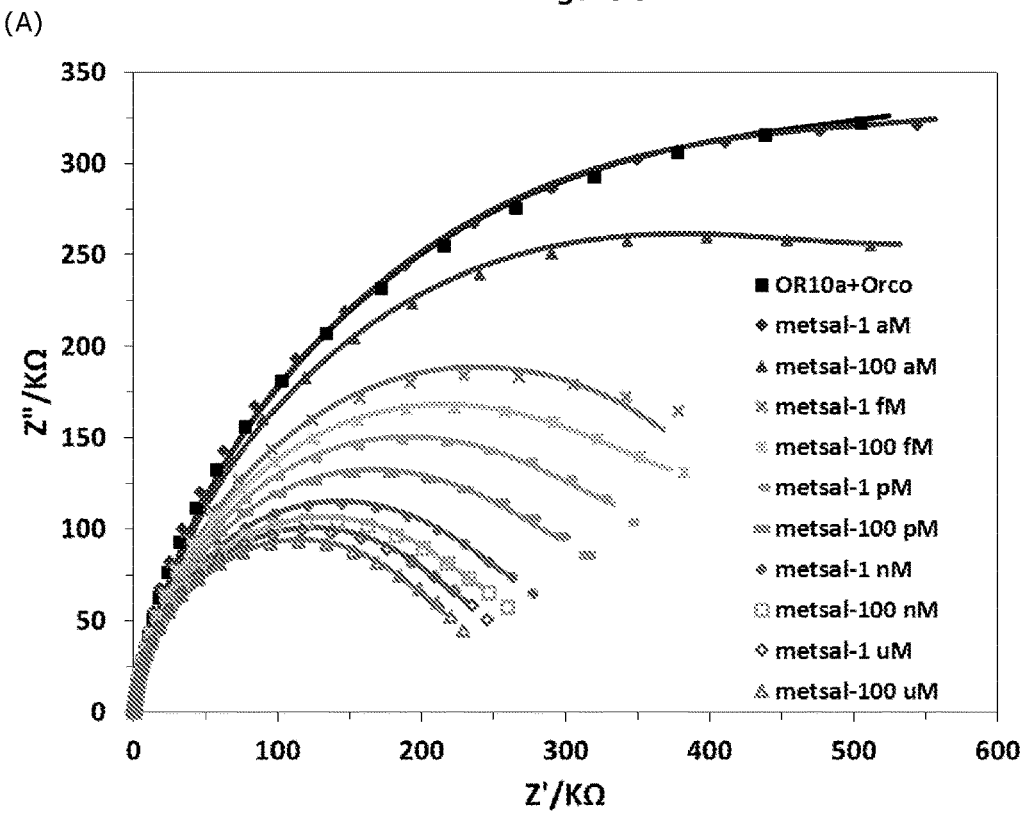
FIG. 5. (A) Impedance evolution of an Or10a/Orco liposomes functionalised electrode versus the target ligand methyl salicylate (metsal) with a concentration range from 1 aM to 10 μM. Experimental data are presented as symbols and the equivalent circuit fitting curves as solid lines. (B) Dose response curve for gold electrodes functionalized with Or10a/Orco liposomes in response to the target ligand Methyl salicylate. The target ligand binding measurements were also performed with gold electrodes functionalised with empty liposomes and Orco liposomes demonstrating a null response. Error bars were generated using standard deviation using four repeats.
Figure 5:
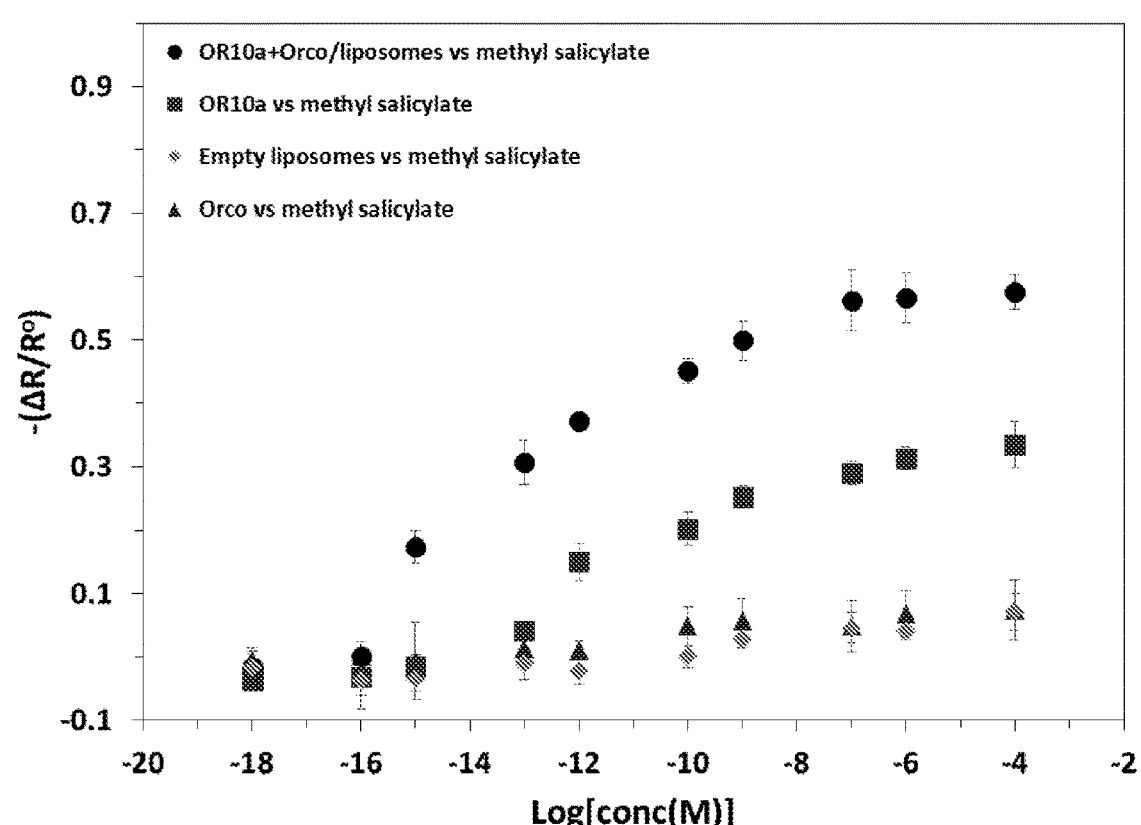

FIG. 5*a* presents the EIS response for the Or10a/Orco liposome functionalized sensors when exposed to its target ligand, methyl salicylate, at various concentrations. FIG. 5*b* compares the methyl salicylate dose response curve for Or10a/Orco liposomes with those obtained for Or10 liposomes, Orco liposomes and empty liposomes. The Or10a/ Orco liposomes show a greater maximal response than Or10a liposomes, and also exhibit a greater sensitivity too, as reflected by the shift to the left of the dose response curve and a lower limit of detection of 1 fM. The Orco liposomes and empty liposomes both show a negligible response to methyl salicylate.

Figure 6:
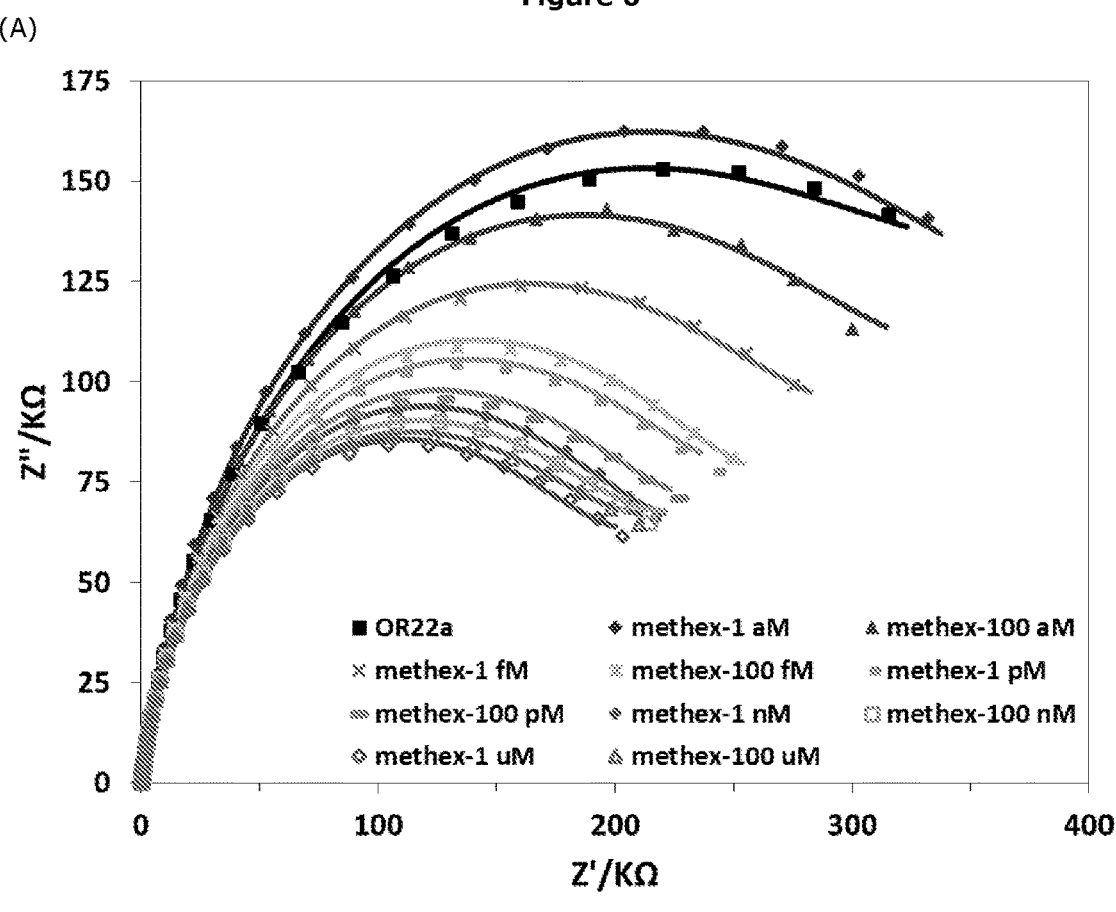
FIG. 6. (A) Impedance evolution of an Or22a liposomes functionalised electrode versus the target ligand methyl hexanoate (methex) with a concentration range from 1 aM to 10 μM. Experimental data are presented as symbols and the equivalent circuit fitting curves as solid lines. (B) Dose response curve for gold electrodes functionalized with Or22a liposomes in response to the target ligand methyl hexanoate, and control ligand methyl salicylate. The target and control ligand binding measurements were also performed with gold electrodes functionalised with empty liposomes. Error bars were generated using standard deviation using four repeats.
Figure 6:
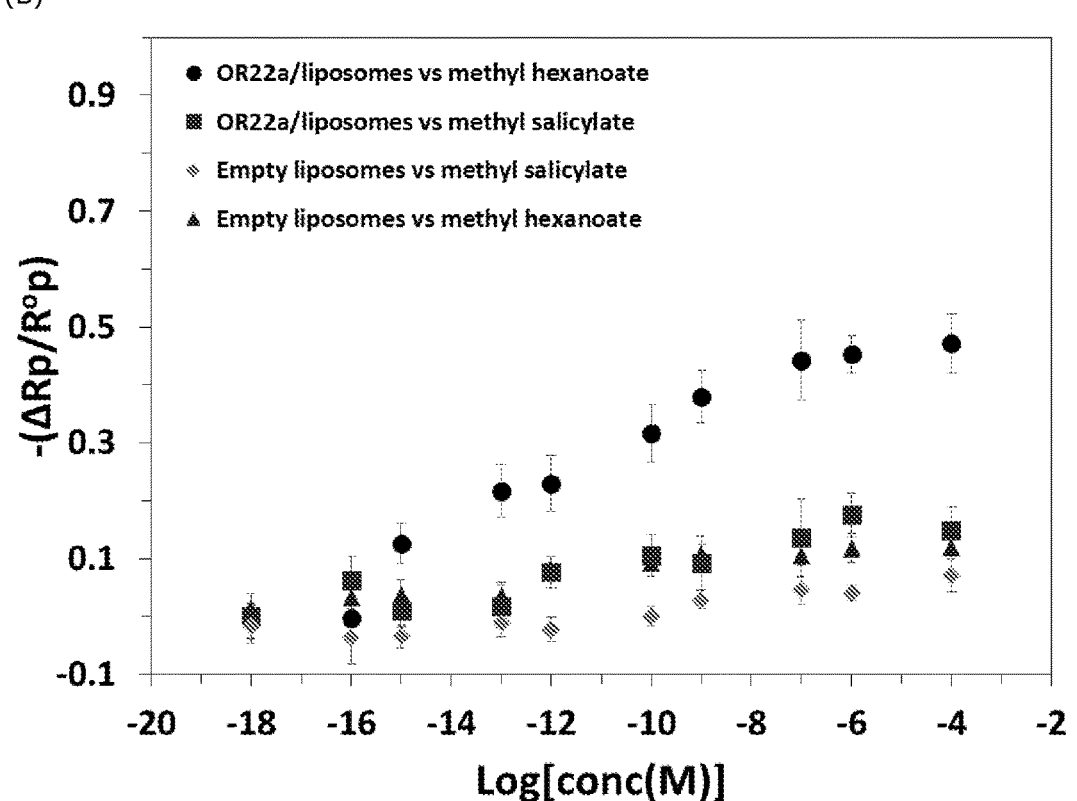

The authors investigate the effect of Orco on another example receptor, Or22a. FIG. 6*a* presents the EIS response for the Or22a liposome functionalized sensors when exposed to one of its target ligands, methyl hexanoate, at various concentrations. Again, the Nyquist plot showed decrease in EIS response after the addition of increasing concentration of methyl hexanoate. The dose response curve (FIG. 6*b*) shows that the Or22a liposomes sensor responded to methyl hexanoate with the limit of detection (LOD) of 1 fM and with negligible response to the control ligand methyl salicylate. The sensor functionalized with the empty liposomes showed negligible responses towards the positive and negative ligand suggesting the OR is the key element to detect the odorants.

Figure 7:
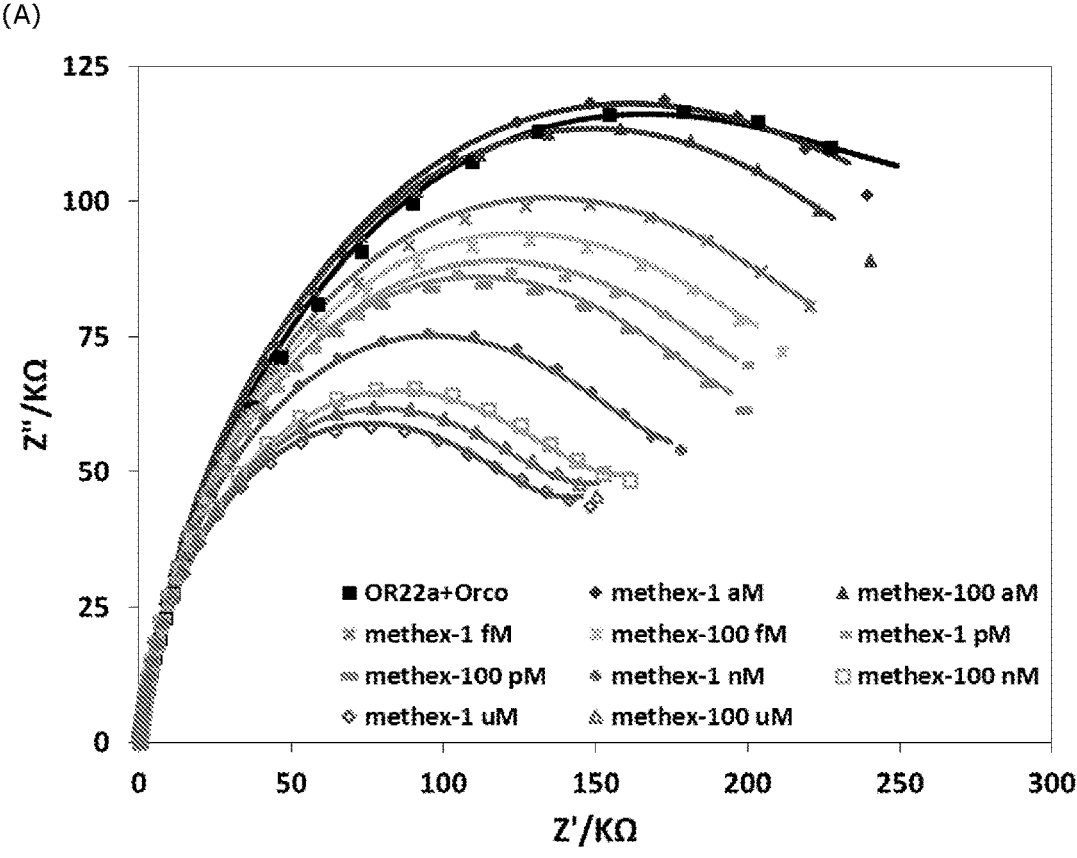
FIG. 7. (A) Impedance evolution of an Or22a/Orco liposomes functionalised electrode versus the target ligand methyl hexanoate (methex) with a concentration range from 1 aM to 100 μM. Experimental data are presented as symbols and the equivalent circuit fitting curves as solid lines. (B) Dose response curve for gold electrodes functionalized with Or22a/Orco liposomes in response to the target ligand methyl hexanoate. The target ligand binding measurements were also performed with gold electrodes functionalised with empty liposomes and Orco liposomes demonstrating a null response. Error bars were generated using standard deviation using four repeats.
Figure 7:
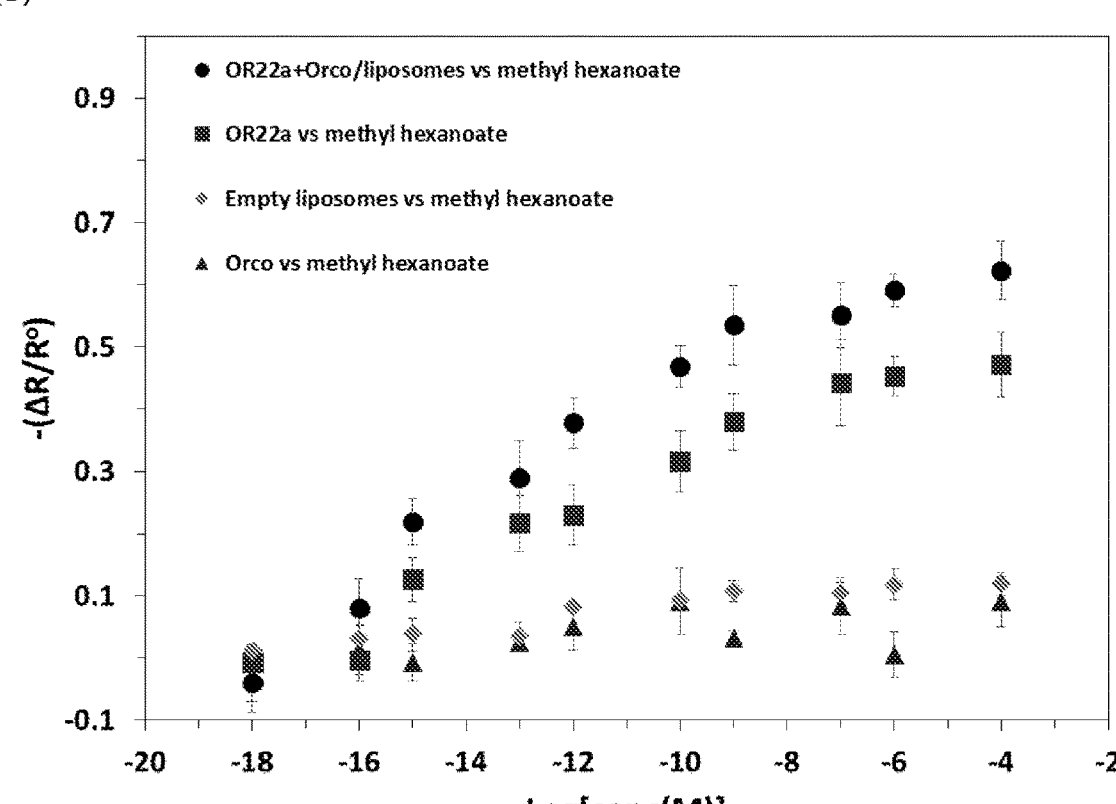

FIG. 7*a* presents the EIS response for the Or22a/Orco liposome functionalized sensors when exposed to its target ligand, methyl hexanoate, at various concentrations. FIG. 7*b* compares the methyl hexanoate dose response curve for Or22a/Orco liposomes with those obtained for Or22a liposomes, Orco liposomes and empty liposomes. As expected, the Or22a/Orco liposomes show a greater maximal response than Or22a liposomes, and also exhibit a greater sensitivity too, as reflected again by the shift to the left of the dose response curve and a lower limit of detection of 0.1 fM. The Orco liposomes and empty liposomes both show a negligible response to methyl hexanoate.

3.0 Discussion

The applicants tested different Self-Assembled Mono layers (SAM layers) initially before identifying 6-mercaptohexanoic acid (MHA) as a linker of optimal length to bind the liposomes on to the gold electrode surface. Previously, 16-mercaptohexadecanoic (16-MHDA) acid was used to functionalize the gold surface and bind the liposomes onto the gold electrode. Results from that experiment did not show high sensitivity suggesting the liposomes were too far away from the electrode surface to give a detectable signal. To overcome that obstacle the applicants used the shorter 6-mercaptohexanoic acid instead. The applicants postulated that this linker being shorter would provide faster electron transfer between gold and liposomes, thus, any event occurring on the surface can be monitored in a more sensitive fashion. In the case of the two papers which immobilised mammalian odorant receptors in crude cell membranes, they used either 16-mercaptohexadecanoic acid (16-MHDA)[35] or 6-mecaptohexadecanoic acid (6-MHDA)[36] for SAM formation.

Comparative data shows that the insect OrX/Orco-EIS biosensor formats as disclosed here are more sensitive than both OrX-EIS biosensors, and other sensor formats that have been used with insect odorant receptors. Table 1 summarises the published data on odorant receptor based devices. The present device provides between 100-100,000-fold greater sensitivity than cell-based sensors.

TABLE 1

Comparison of insect odorant receptor sensor device data.

| Sensor/assay approach | Receptor-analyte | Sensitivity limit | $EC_{50}$ | Ref |
|---|---|---|---|---|
| Stable Sf21 cell line on microfluidics chip-fluorescence | BmOR1/Orco-Bombykol pheromone | $1 \times 10^{-6}$ M | $4.39 \times 10^{-6}$ M | 15 |
| | BmOR3/Orco-Bombykal pheromone | $0.3 \times 10^{-6}$ M | $2.03 \times 10^{-6}$ M | |
| Xenopus oocytes on a microfluidics device-two electrode voltage clamping (TEVC) | BmOR1/Orco-Bombykol pheromone | $10^{-8} - 10^{-6}$ M* | $0.25 \times 10^{-6}$ M | 14 |
| | BmOR3/Orco-Bombykal pheromone | $10^{-8} - 10^{-6}$ M* | $0.38 \times 10^{-6}$ M | |
| | PxOR1/Orco-Z11-16:Ald | $10^{-8} - 10^{-6}$ M* | $2.52 \times 10^{-6}$ M | |
| | DOr85b/Orco to 2-heptanone | $10^{-8} - 10^{-6}$ M* | $45.6 \times 10^{-6}$ M | |
| Insect OrX-EIS device | DmOr10a-methyl salicylate | $\sim 10^{-10}$ M* | $\sim 10^{-10}$ M | Present study |
| | DmOr10a/Orco-methyl salicylate | $\sim 10^{-15}$ M* | $\sim 10^{-12}$ M | |
| | DmOr22a-methyl hexanoate | $\sim 10^{-15}$ M* | $\sim 10^{-12}$ M | |
| | DmOr22a/Orco-methyl hexanoate | $\sim 10^{-16}$ M* | $\sim 10^{-13}$ M | |

49

50

Table 2 summarises data obtained from cell assays. The present insect OrX-EIS sensor and OrX/Orco-EIS data is more sensitive than OrX/Orco expressed in HEK293 cells and *Xenopus* oocytes. Note in these systems some pheromone receptors (PRs) exhibit much lower sensitivity than normal odorant receptors, this is to be expected as these receptors are finely tuned to their pheromone target molecules.

\* indicates value has been estimated from a visual assessment of dose response data plotted on a graph in the cited reference.

TABLE 2

Overview of insect ORX/Orco cell assay data.

| Sensor/assay approach | Receptor-Analyte | Sensitivity limit | Ec50 | Ref |
|---|---|---|---|---|
| Insect Sf9 transient cell assay | EpOR1/Orco-geraniol | $10^{-14}$ M* | $1.8 \times 10^{-12}$ M | 37 |
| Insect Sf9 transient cell assay | EpOR3/Orco-Citral | $10^{-15}$ M* | $1.1 \times 10^{-13}$ M | 37 |
| Insect Sf9 transient cell assay | DmOr22a/Orco-ethyl butyrate | $10^{-12}$ M* | $1.58 \times 10^{-11}$ M | 38 |
| Insect Sf9 transient cell assay | BmOr19/Orco-linalool | $10^{-10}$ M* | $4.69 \times 10^{-9}$ M | 5 |
| Insect Sf9 transient cell assay | BmOr45/Orco-benzoic acid | $10^{-11}$ M* | $1.44 \times 10^{-10}$ M | 5 |
| Insect Sf9 transient cell assay | BmOr47/Orco-benzoic acid | $10^{-14}$ M* | $1.42 \times 10^{-11}$ M | 5 |
| Insect Sf9 transient cell assay | Am151/Orco-Floral mixture | $10^{-10}$ M* | $1.54 \times 10^{-9}$ M | 39 |
| Insect Sf9 transient cell assay | Am152/Orco-Floral mixture | $10^{-10}$ M* | $6.55 \times 10^{-9}$ M | 39 |
| HEK293 stable cell assay | EpOR3/Orco-geranyl acetate | | $1.0 \times 10^{-6}$ M | 6 |
| HEK293 stable cell assay | ApolOR1/Orco-(+ApolPBP2, (E,Z)-6,11-hexadecadienal: pheromone) | $10^{-15}$ M* | $10^{-13}$ M? | 40 |
| HEK293 stable cell assay | HR13/Orco-PBP2 (+pheromone) | $10^{-13}$ M | 200 fM | 41 |
| HEK293 stable cell assay | HR13/Orco-DMSO (+pheromone) | $10^{-10}$ M | 1.2 nM | 41 |
| HEK293 stable cell assay | BmOR-1/Orco-PBP (+pheromone) | $10^{-12}$ M | | 42 |
| HEK293 stable cell assay | DmOr22a/Orco-methyl hexanoate | Log = −7.5* | Log = −6.38 | 43 |
| HEK293 stable cell assay | AgOr65/Orco-eugenol | Log = −7* | Log = −6.54 | 43 |
| HEK293 stable cell assay | DmOr22a/Orco-methyl hexanoate) | Log = −7* | $1.17 \times 10^{-6}$ M | 44 |
| HEK293 stable cell assay | AgOr48/Orco-g-dodecalactone) | Log = −8* | Log = −7.01 | 45 |
| *Xenopus* oocytes | ECB (Z) OR3/Orco-E11 pheromone | $10^{-9}$ M | $12.5 \times 10^{-9}$ M | 2 |
| *Xenopus* oocytes | ACB OR3/Orco-E12 pheromone | $1 \times 10^{-9}$ M | $7 \times 10^{-9}$ M | 2 |
| *Xenopus* oocytes | SexiOR13/Orco-Z9, E12-14:OAc pheromone. | | $3.158 \times 10^{-6}$ M | 46 |
| *Xenopus* oocytes | SexiOR16/Orco-Z9-14:OH pheromone. | | $9.690 \times 10^{-7}$ M | 46 |
| *Xenopus* oocytes | OscaOR1/Orco-E11-14:OH pheromone. | $10^{-7}$ M* | $10^{-6}$ M | 47 |
| *Xenopus* oocytes | MsiOR1/Orco-Z11-16:Ac pheromone | $10^{-7}$ M* | $10^{-6}$ M | 48 |
| *Xenopus* oocytes | DIOR1/Orco-Ell-16:Ald pheromone | $10^{-7}$ M* | $10^{-6}$ M | 48 |
| *Xenopus* oocytes | BmOr1/Orco-bombykol pheromone | | $34 \times 10^{-6}$ M | 49 |
| *Xenopus* oocytes | BmOr1/Orco-bombykol pheromone | | $5.9 \times 10^{-6}$ M | 50 |
| *Xenopus* oocytes | HVOR6/Orco-Z9-14:ald pheromone | | $9.79 \times 10^{-7}$ M | 51 |
| *Xenopus* oocytes | HVOR13/Orco-Z11-16:ald pheromone | | $9.79 \times 10^{-7}$ M | 51 |
| *Xenopus* oocytes | OnOr1/Orco-E12-14:OAc pheromone | | $2.6 \times 10^{-7}$ M | 52 |
| *Xenopus* oocytes | AgOR1/Orco-4-methylphenol | | $4.12 \times 10^{-7}$ M | 25 |
| *Xenopus* oocytes | AgOR2/Orco-indole | | $1.67 \times 10^{-8}$ M | 25 |
| *Xenopus* oocytes | AgOR8/Orco-1-octen-3-ol | | $1.86 \times 10^{-7}$ M | 25 |
| *Xenopus* oocytes | AgOr10/Orco-indole | | $1.37 \times 10^{-7}$ M | 25 |
| *Xenopus* oocytes | AgOr65/Orco-eugenol | | $3.44 \times 10^{-8}$ M | 25 |

*indicates value has been estimated from a visual assessment of dose response data plotted on a graph.

4.0 Conclusion

This study has demonstrated the improved recognition ability of OrXs in the presence of Orco in olfactory biosensors based on electronic device platforms. OrXs embedded with the Orco subunit in liposomes which are functionalized on the gold electrodes show an increased sensitivity (below fM) and maximal response when compared with OrX liposomes. Compared with results from empty liposomes functionalized electrodes, no clear impedance response to target ligands are observed. The specific binding of each OrX has also been verified by testing the response to control ligands from the OrX liposome functionalized electrodes.

EXAMPLE 2—FURTHER EXEMPLIFICATION OF THE SENSOR OF THE INVENTION WITH ELECTRICAL IMPEDANCE SPECTROSCOPY (EIS)

Summary

The applicants further demonstrate the convenient, sensitive sensor device using an additional insect OrX sequence. Or35a[19] was embedded on its own or with Orco in liposomes[28] and functionalized to gold electrodes for EIS measurements in a similar manner to Example 1. As previously seen for the receptors Or10a and Or22a in Example 1, the presence of Orco in the liposomes has an additive, or amplifying, effect on the Or35a response, increasing the sensitivity of the OrX for its target ligand.

1. Experimental Methods 1.1 Materials 6-mercaptohexanoic acid (MHA), N-hydroxysuccinimide (NHS), 1-ethyl-3-(3-dimethylaminopropyl)-carbodiimide) (EDC), phosphate buffer saline (PBS) tablets, methyl salicylate, and methyl hexanoate were obtained from Sigma-Aldrich. 1.6 mm diameter gold (Au) disk electrode, coiled platinum (Pt) wire electrode and leakless silver/silver chloride (Ag/AgCl) electrode were purchased from BASi for electrochemical measurements.

1.2 Preparation of Purified Or35a and Orco Subunits

Or35a and Orco subunits were prepared as described in Example 1 section 1.2.

1.3 Preparation of OR Associated Liposomes

Or35a liposomes were prepared as described in Example 1 section 1.3 with the following alterations:

Prior to use, 1 mg liposomes (500 μl at 2 mg/ml) were defrosted on ice and then destabilized by incubating with 0.2% CHAPS for 15 min at room temperature. Then 50 μg of purified Or35a/Orco was added and rotated at 10 rpm for 1 h at room temperature. Excess detergent was removed by addition of 500 mg of Bio-Beads SM-2 (Bio-Rad, USA) and overnight incubation at 4° C. The tube was pierced at both ends and Or35a/Orco integrated liposomes were separated from the Bio-Beads by centrifugation at 5000 g for 1 min. All Or35a/Orco integrated liposomes samples were analysed by Western blot before being aliquoted and stored at −80° C. Integration of Or35a/Orco into liposomes was assessed by density gradient ultracentrifugation (DGU) using Accudenz (Accurate Chemical & Scientific Corporation, USA). The Or35a/Orco integrated liposomes were brought to 40% Accudenz by the addition of an equal volume of 80% Accudenz solution, placed at the bottom of an ultra-centrifugation tube, and overlaid with 30% Accudenz solution, and DGU buffer (25 mM HEPES pH 7.5, 100 mM NaCl, 10% glycerol). The sample was then centrifuged at 100,000 g for 4 h at 4° C. Liposomes floated to the top of the gradient after Accudenz DGU due to their low density.

2. Results

The applicants investigated the effect of Orco on the ligand binding activity of Or35a embedded in liposomes by performing EIS measurements as described in Experiment 1 section 2.0.

Figure 8:
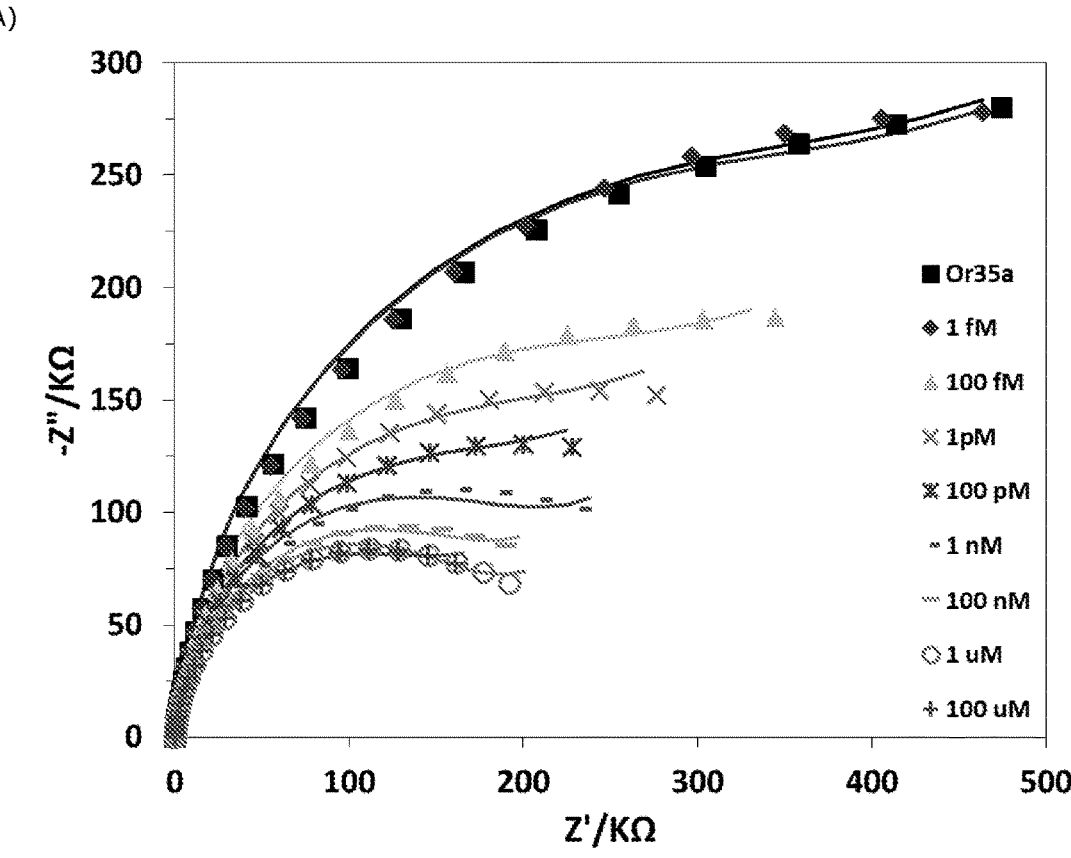
FIG. 8. (A) Impedance evolution of (A) an Or35a in liposomes functionalised electrode versus the target ligand E2-hexenal with a concentration range from 1 aM to 100 μM. Experimental data are presented as symbols and the equivalent circuit fitting curves as solid lines. (B) Dose response curve for gold electrodes functionalized with Or35a liposomes in response to the target ligand E2-hexenal, and control ligand methyl salicylate. The target and control ligand binding measurements were also performed with gold electrodes functionalised with empty liposomes. Error bars were generated using standard deviation using four repeats.
Figure 8:
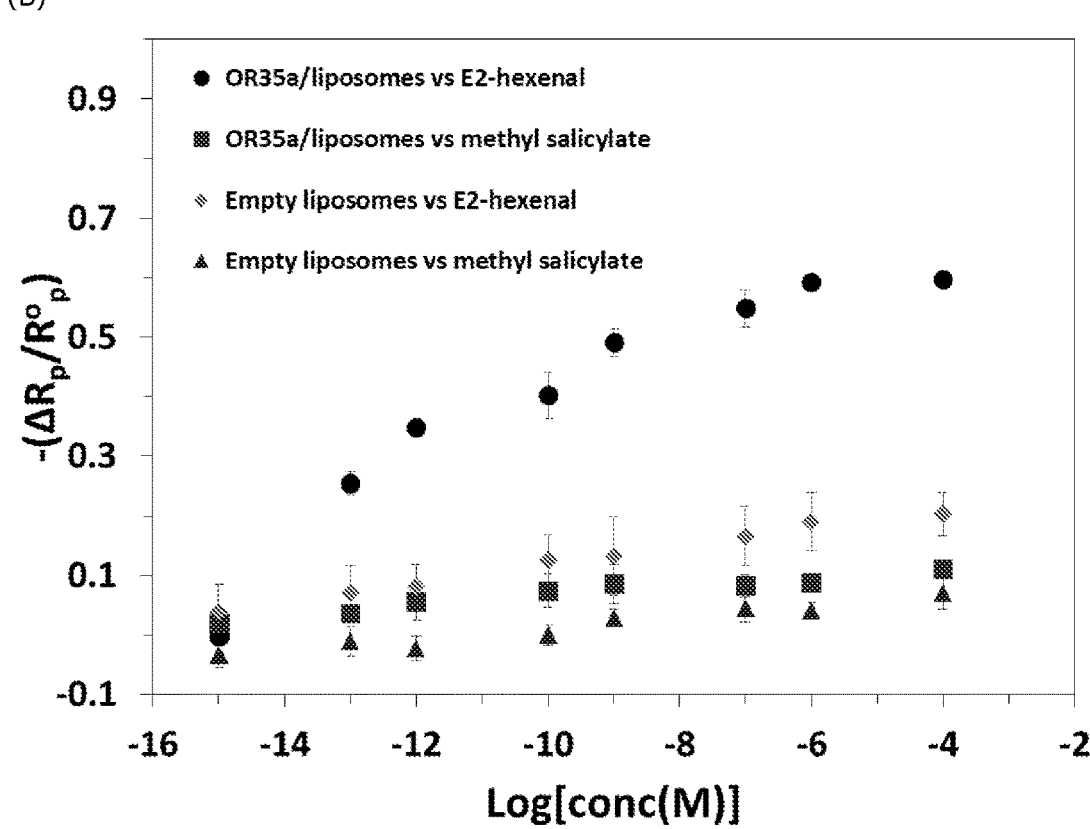

FIG. 8a presents the EIS response for the OR35a liposome functionalized sensors when exposed to one of its target ligands, E2-hexenal, at various concentrations. Again, the Nyquist plot showed decrease in EIS response after the addition of increasing concentration of E2 hexenal. The dose response curve (FIG. 8) shows that the Or35a liposomes sensor responded to E2 hexenal with the limit of detection (LOD) of 10 fM and with negligible response to the control ligand methyl salicylate. The sensor functionalized with the empty liposomes showed negligible responses towards the positive and control ligand suggesting the OR is the key element to detect the odorants.

Figure 9:
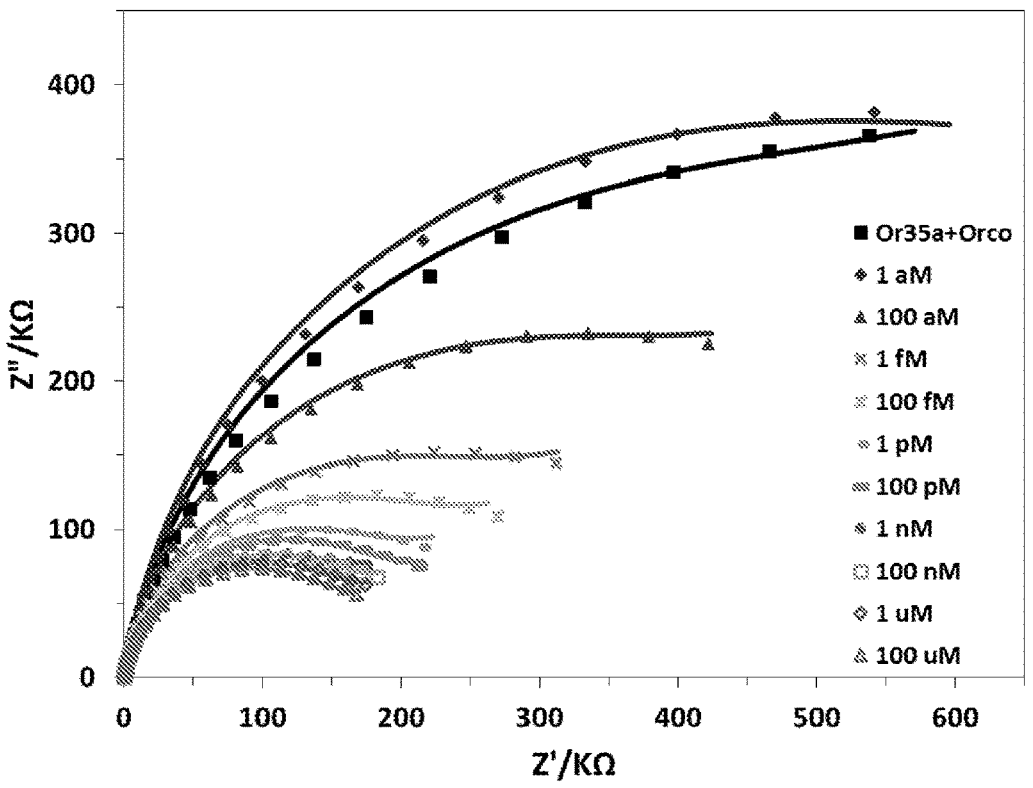
FIG. 9. (A) Impedance evolution of (A) an Or35a/Orco in liposomes functionalised electrode versus the target ligand E2-hexenal with a concentration range from 1 aM to 100 μM. Experimental data are presented as symbols and the equivalent circuit fitting curves as solid lines. B) Dose response curve for gold electrodes functionalized with Or35a/Orco liposomes in response to the target ligand E2-hexenal. The target ligand binding measurements were also performed with gold electrodes functionalised with empty liposomes and Orco liposomes demonstrating a null response. Error bars were generated using standard deviation using four repeats.
Figure 9:
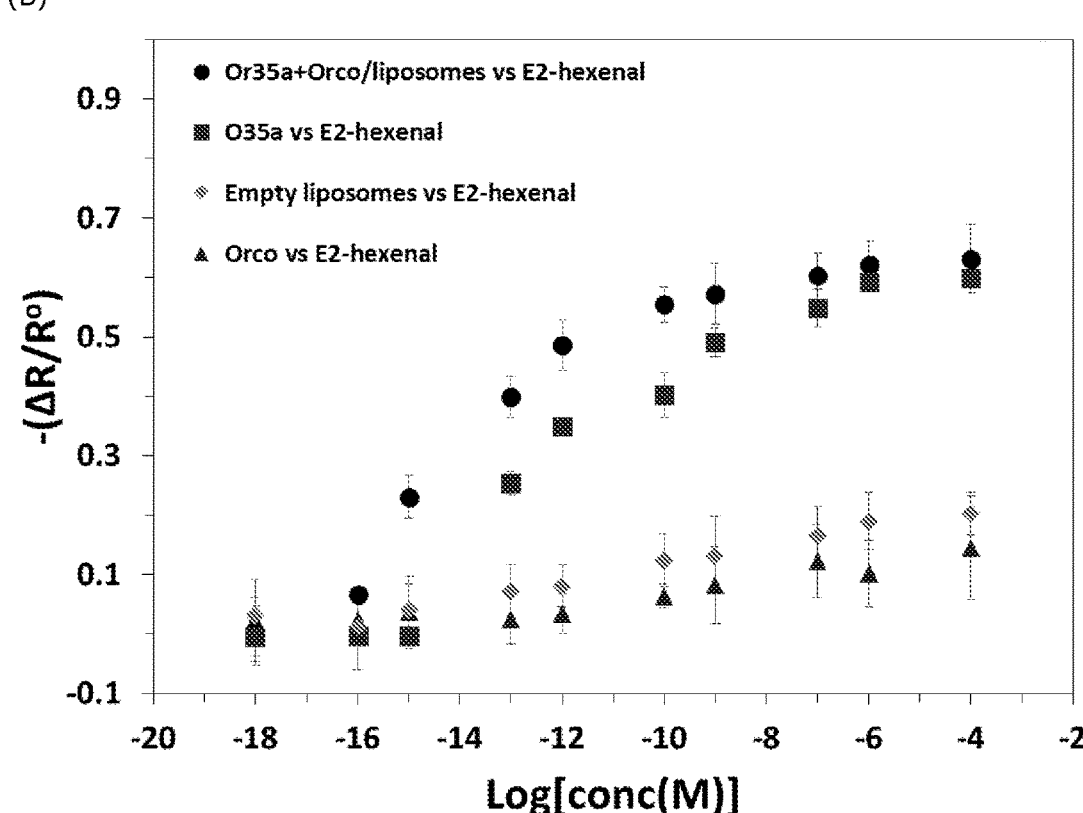

FIG. 9a presents the EIS response for the OR35a/Orco liposome functionalized sensors when exposed to its target ligand, E2-hexenal, at various concentrations. FIG. 9b compares the E2-hexenal dose response curve for Or35a/Orco liposomes with those obtained for Or35a liposomes, Orco liposomes and empty liposomes. As expected, the Or35a/Orco liposomes show a greater maximal response than Or22a liposomes, and also exhibit a greater sensitivity too, as reflected again by the shift to the left of the dose response curve and a lower limit of detection of 0.1 fM. The Orco liposomes and empty liposomes both show a negligible response to methyl hexanoate.

Figure 10:
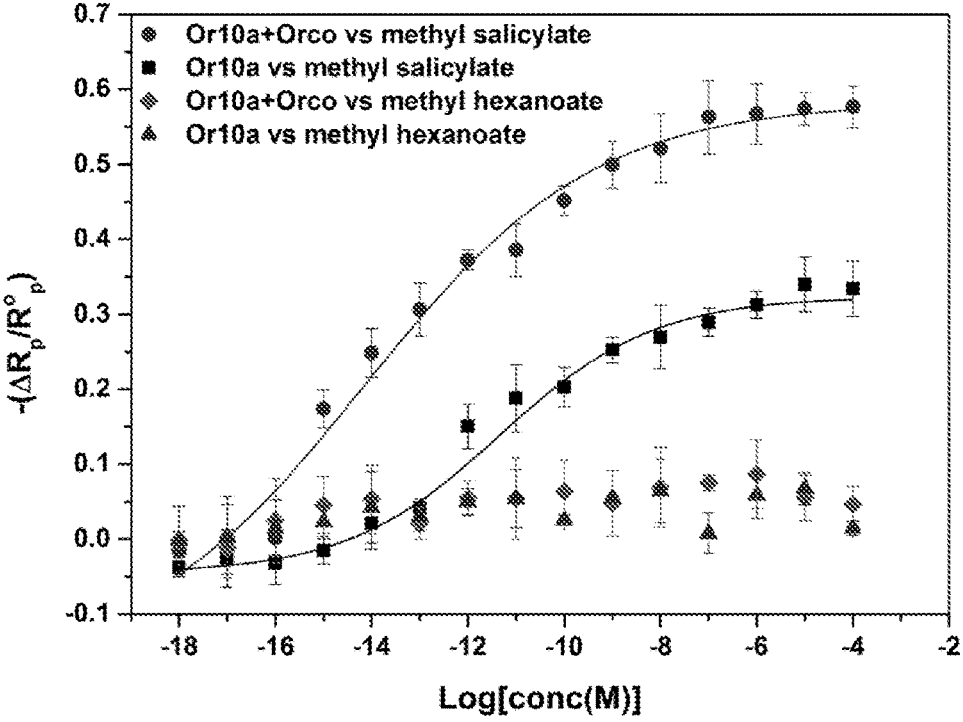
FIG. 10. Summary of EIS dose response curves for (a) Or10a+/−Orco, (b) Or22a+/−Orco, and (c) Or35a+/−Orco liposomes in response to target and control ligands. All three dose response curves show that the presence of Orco causes each OrX receptor to bind its target compound with greater sensitivity, thus shifting the dose response curve to the left. Error bars were generated using standard deviation using four repeats.
Figure 10:
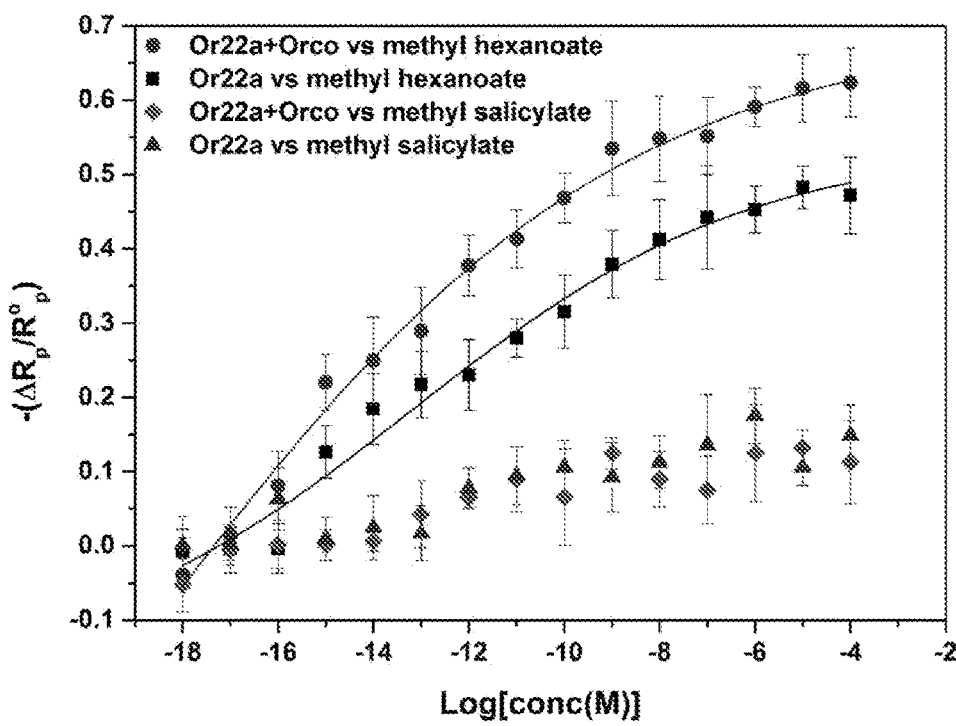
Figure 10:
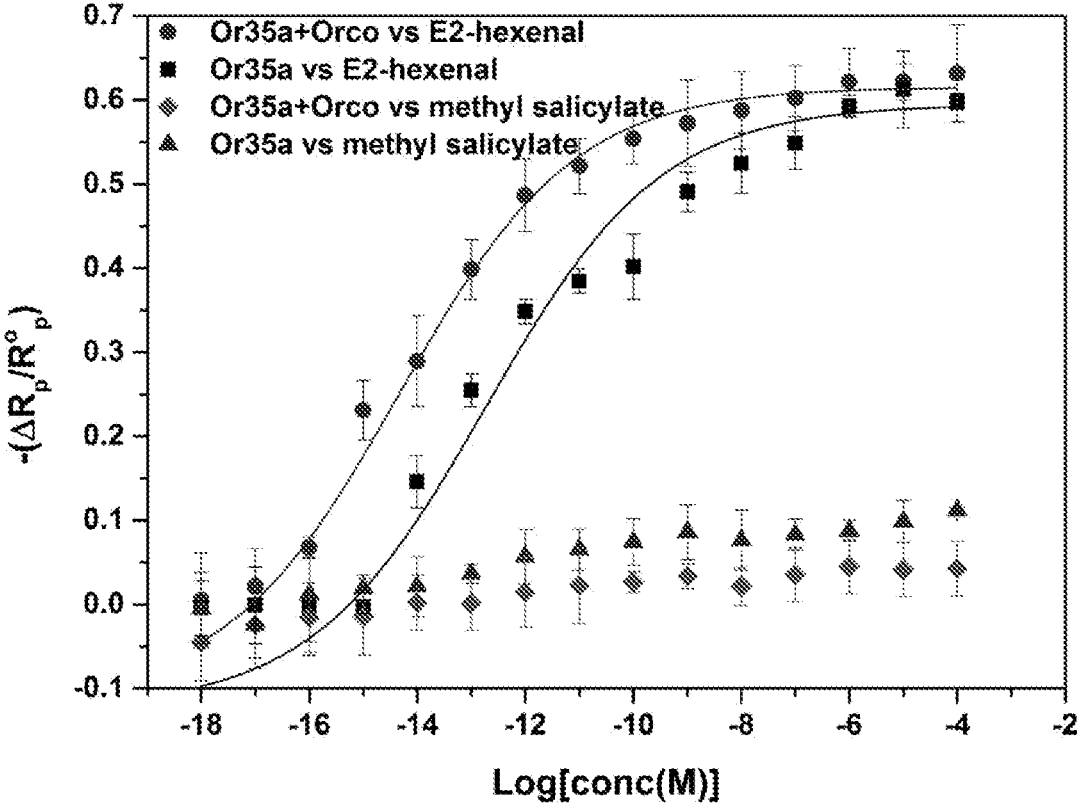

FIG. 10 summarises clearly the shift in the dose response curves to the left for the OrX and OrX/Orco based EIS biosensors tested in Example 1 and 2. The dose response equation, $EC_{50}$ and detection range for the OrX and OrX/Orco based EIS biosensors are summarised in Table 3. For the receptors tested in Example 1 and Example 2, the resulting sensors showed an improvement in sensor response in the presence of Orco in the form of lower LODs and $EC_{50}$ values.

TABLE 3

Dose response equation, $EC_{50}$ and detection ranges of OrX and OrX/Orco based EIS biosensors.

| Receptor | Analyte | Dose Response Equation | $EC_{50}$ | Detection Range |
|---|---|---|---|---|
| Or10a | Methyl salicylate | $y = 0.31/(1 + \exp(-0.80 \times (x + 10.89)))$ | $2.2\ (\pm 0.9) \times 10^{-12}$ M | $10^{-13}$ to $10^{-7}$ M |
| Or10a/Orco | Methyl salicylate | $y = -0.17 + (0.75)/(1 + 10^{((-14.13 - x) \times 0.18)})$ | $7.39 \times 10^{-14}$ M | $10^{-15}$-$10^{-7}$ M |
| Or22a | Methyl hexanoate | $y = 0.46/(1 + \exp(-0.53 \times (x + 12.08)))$ | $1.1\ (\pm 2.1) \times 10^{-12}$ M | $10^{-15}$ to $10^{-5}$ M |
| Or22a/Orco | Methyl hexanoate | $y = -0.95 + (1.65)/(1 + 10^{((-18.83 - x) \times 0.08)})$ | $1.46 \times 10^{-14}$ M | $10^{-16}$-$10^{-5}$ M |
| Or35a | E2-hexenal | $y = 0.61 * \exp(-\exp(-0.41 * (x + 12.94)))$ | $2.8\ (\pm 2.3) \times 10^{-13}$ M | $10^{-14}$ to $10^{-6}$ M |
| Or35a/Orco | E2-hexenal | $y = -0.11 + (0.72)/(1 + 10^{((-14.32 - x) \times 0.26)})$ | $4.74 \times 10^{-15}$ M | $10^{-16}$-$10^{-6}$ M |

3. Conclusion

This study has demonstrated the improved recognition ability of Or35a in the presence of Orco in olfactory biosensors based on electronic device platforms. Or35a embedded with the Orco subunit in liposomes which are functionalized on the gold electrodes show an increased sensitivity (below fM) when compared with Or35a liposomes. Compared with results from empty liposomes functionalized electrodes, no clear impedance response to target ligands are observed. The specific binding of Or35a has also been verified by testing the response to a control ligand from the Or35a liposome functionalized electrodes.

EXAMPLE 3—EXEMPLIFICATION OF THE SENSOR OF THE INVENTION WITH QUARTZ CRYSTAL MICROBALANCE (QCM) PIEZOELECTRIC TRANSDUCER

Summary

The applicants have produced a convenient piezoelectric sensor device using the *Drosophila melanogaster* Or10a[19] sequence embedded in liposomes in the absence and presence of the Orco sequence. Quartz Crystal microbalance with Dissipation monitoring (QCM-D) is a mass sensitive piezoelectric transducer, whose oscillation frequency changes with the mass loading on the crystal. The interaction between Or10a and the target ligand methyl salicylate was detected by monitoring the oscillation frequency changes of QCM-D sensor with Or10a liposomes and Or10a/Orco liposomes coupled to it. Or10a/Orco liposomes were found to have a greater response to methyl salicylate than Or10a liposomes. This result suggests the presence of the Orco subunit in the liposomes is having an additive effect on the response of an OrX amplifying its response to ligand binding. The specificity of the binding was verified by testing the response of Or10a liposomes and Or10a/Orco liposomes coupled to the QCM-D sensor to the control ligand methyl hexanoate, where there was negligible response.

1. Experimental Methods 1.1 Materials 6-mercaptohexanoic acid (MHA), N-hydroxysuccinimide (NHS), 1-ethyl-3-(3-dimethylaminopropyl)-carbodiimide) (EDC), phosphate buffer saline (PBS) tablets, and methyl salicylate were obtained from Sigma-Aldrich. Gold (100 nm) sensor crystals (QSX301) were obtained from ATA Scientific Instruments.

1.2 Preparation of OR Associated Liposomes 1.2.1 Preparation of Purified OR Subunits OR subunits were prepared as described in Example 1 section 1.2

1.2.2 Preparation of OR Associated Liposomes

Or22a liposomes were prepared as described in Example 1 section 1.3

1.3 Quartz Crystal Microbalance (QCM) Preparation and Data Collection

Gold (100 nm) sensor crystals were sonicated in ethanol and milli-Q water for 15 minutes each respectively. A 5:1:1 volume ratio of milli-Q water, ammonia (25%), and hydrogen peroxide (30%) was heated to 75° C. for 5 minutes and the sonicated crystals were placed in the heated solution for 5 minutes. Then the crystals were removed from the solution and rinsed with milli-Q water before drying with nitrogen gas. The clean gold crystals were thiol-functionalized by exposing them to 2 mM ethanolic solution of MHA overnight followed by washing with ethanol solution in order to remove excess or loosely bound molecules. NHS/EDC was prepared using 2:1 mol:mol ratio of EDC:NHS (100 mM EDC, 50 mM NHS) in 2 ml PBS (pH=6.5) solution. Each OrX/liposome stock solution was diluted 100 fold for QCM-D measurements in PBS buffer solution (pH=7.4). The SAM functionalized crystals were then placed into the Q-sense analyser instrument (Biolin Scientific) chamber and flowed with the NHS/EDC, Or10a/liposomes or Or10a/Orco liposomes, and various concentrations of methyl hexanoate (1.6 µM, 8 µM, 20 µM, 40 µM, 100 µM, 200 µM, 500 µM and 1000 µM) in PBS buffer solution containing 1% DMSO to measure the changes in frequency ($\Delta f$) and dissipation ($\Delta D$) values.

2. Results

Figure 11:
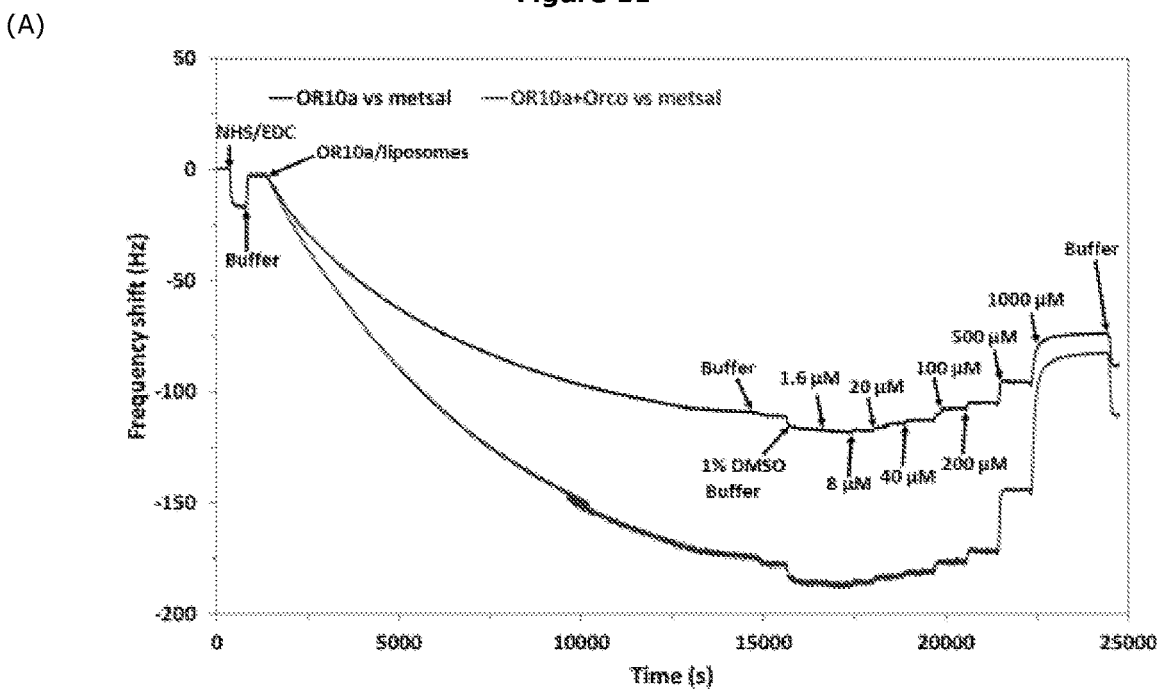
FIG. 11. (A) The change in frequency on the Quartz crystal microbalance with Dissipation (QCM-D) with SAM and NHS/EDC modification, Or10a liposome (top) or Or10a/Orco liposome (bottom) immobilisation followed by binding of the target ligand methyl salicylate (metsal). (B) Shows a close up view of the change in frequency with increasing concentrations of methyl salicylate (buffer with 1% DMSO, 1.6, 8, 20, 40 100, 200, 500 and 1000 μM) for the Or10a liposome (top) or Or10a/Orco liposome (bottom) immobilised QCM-D sensor. (C) Dose response curves showing detection of target ligand methyl salicylate, and control ligand methyl hexanoate (methex) when exposed to either Or10a liposomes or Or10a/Orco liposomes immobilized gold crystals. Error bars; standard deviation (SD) were generated using two repeats.
Figure 11:
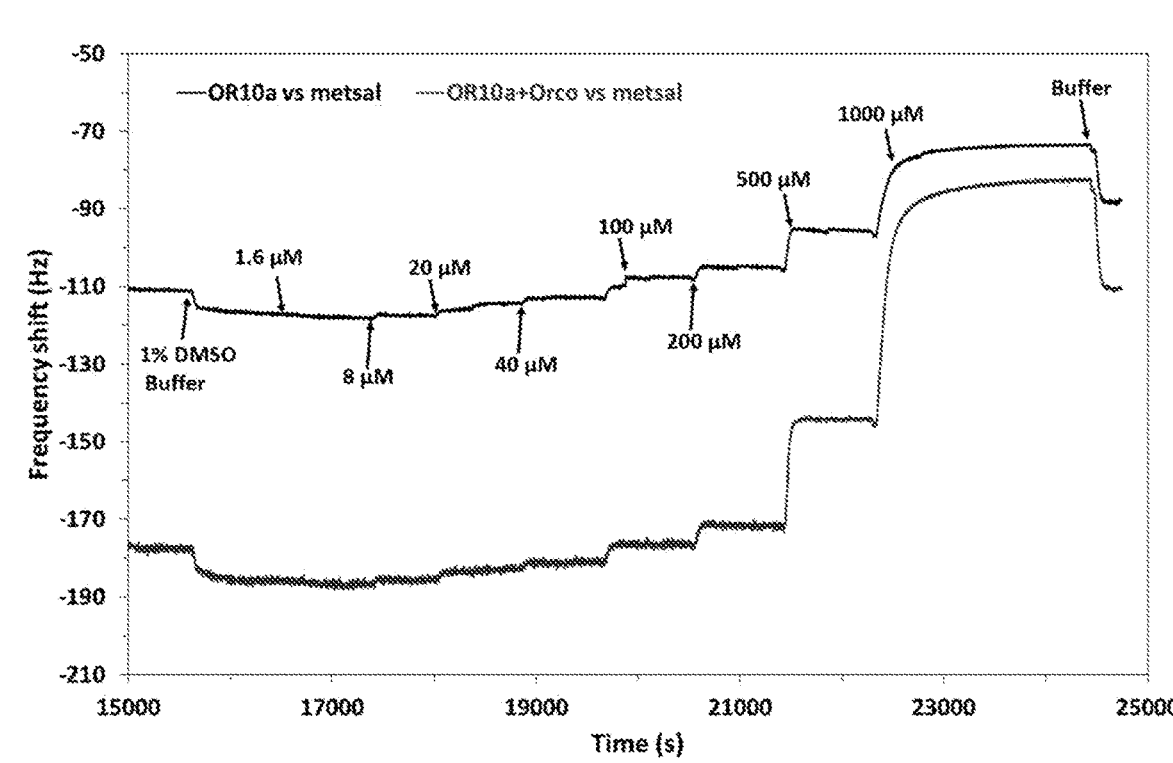

FIG. 11 (*a*) shows the change in frequency upon the SAM and NHS/EDC modification, followed by Or10a liposome or Or10a/Orco liposome immobilisation on the quartz crystal and then binding of the target ligand methyl salicylate. When a binding event occurs on the crystal this results in an increase in the mass reducing the frequency of oscillations[3]. Thus the mass of the sensor increases with SAM, NHS/EDC, and Or10a liposome or Or10a/Orco immobilisation. However, in the case of methyl salicylate binding an increase in the frequency is observed for both types of liposomes (FIG. 11 (*b*)). Without wishing to be bound by theory, the inventors suggest this loss of mass on the sensor is due to the binding of methyl salicylate to the Or10a receptor causing a release of water and ions from inside the Or10a liposomes i.e. the Or10a is forming a functional ion channel. Likewise, the binding of methyl salicylate to the Or10a receptor causing a release of water and ions from inside the Or10a/Orco liposomes i.e. Or10a/Orco is forming a functional ion channel. However, the Or10a/Orco liposomes exhibit a much larger change in frequency, indicating the Orco subunit is amplifying the response from the Or10 a subunit. Comparison of dose response curves for both types of liposomes shows the Or10a/Orco liposomes respond more strongly at higher methyl salicylate concentrations (FIG. 11*c*). In both cases, this increase in frequency occurs with increasing concentrations of methyl hexanoate between 1.6 to 1000 µM indicating that methyl salicylate is binding specifically to the Or10a receptor, as this increase in frequency is not observed with the control ligand methyl hexanoate (FIG. 11*c*). Detection of ligand binding at the M level equivalent to parts-per-trillion (ppt) concentration is on par with what has been seen with *C. elegans* ODR-10[54].

3. Conclusion

This study has demonstrated the recognition ability of OrXs in olfactory biosensors based on electronic device platforms. OrXs in liposomes which are functionalized on quartz crystal microbalance (QCM) piezoelectric sensors can specifically detect their target ligand. An OrX in combination with Orco shows a stronger response to their target ligand, indicating Orco has an additive or amplifying effect on the response of an OrX to its ligand. The response is OrX specific as no clear piezoelectric response was observed to the control ligand. OrX/Orco liposomes functionalized QCMs show great promise to specifically and sensitively detect their target ligands.

EXAMPLE 4—EXEMPLIFICATION OF THE SENSOR WITH GRAPHENE FIELD EFFECT TRANSISTORS (GFETS)

SUMMARY

The applicants have produced a convenient GFET sensor device using the *Drosophila melanogaster* Or10a and Or22a sequences[19] embedded in liposomes in the absence and presence of the Orco sequence. The experimental results showed the in vitro sensing of insect ORs with GFET platforms. Each of the OrX functionalized GFETs has shown a clear electronic response to its target ligands (Or10a to methyl salicylate, Or22a to methyl hexanoate)[20] starting at pM concentrations. The presence of Orco in the liposomes has an additive, or amplifying, effect on the OrX response, increasing the sensitivity of the OrX for its target ligand down to fM concentrations. The specificity of the binding is verified by testing each OrX liposomes and OrX/Orco liposomes functionalized GFET response to non-responding ligands. To further ensure the specificity the response of empty liposomes functionalized GFETs to the target ligands were also tested.

1. Experimental Methods 1.1 Materials

The nitrogen (≤99.99%) and oxygen (99.7%) for the experiments were purchased from BOC limited New Zealand. Deionised (DI) water (18.2 MΩ) used was obtained from a Sartorius (Arium® 611 VF) DI water plant. For GFET fabrication a wafer containing mechanically transferred CVD Graphene on 300 nm $SiO_2$/p-type Si substrate was purchased from Advanced Chemical Supplier, CA, USA; the positive photoresist AZ1518 was purchased from Microchem, Germany; and 1-Pyrenebutyric acid N-hydroxysuccinimide ester (PBASE) (95%, Sigma Aldrich) was used as the molecular linker to tether the OrX and OrX/Orco liposomes to the surface of the graphene present on the GFET device.

1.2 Preparation of OR Associated Liposomes 1.2.1 Preparation of Purified OR Subunits OR subunits were prepared as described in Example 1 section 1.2

1. 1.2.2 Preparation of OR Associated Liposomes

OR liposomes were prepared as described in Example 1 section 1.3

1.3 Preparation of GFET Sensors

Figure 12:
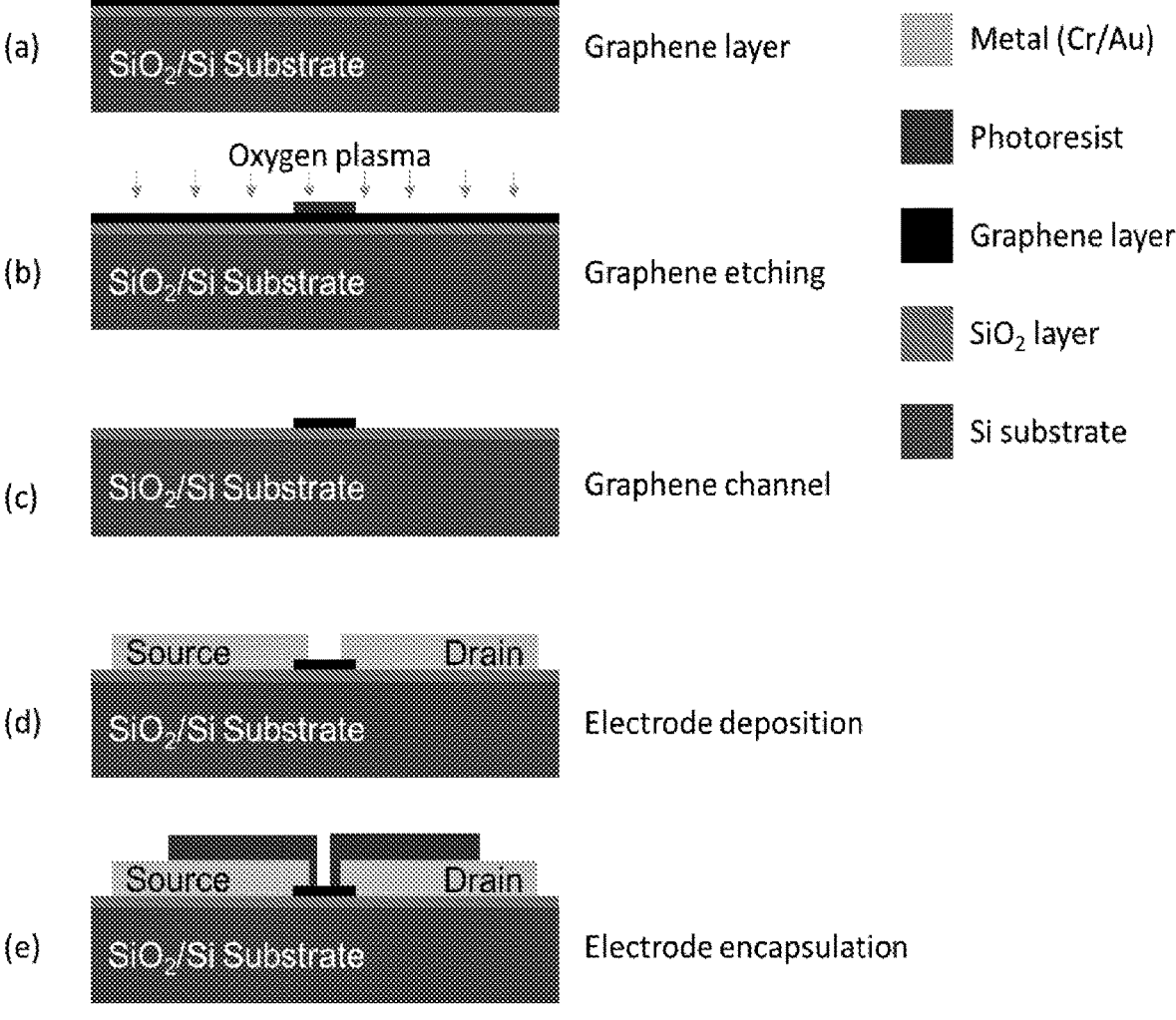
FIG. 12: Key steps involved in GFET fabrication on Si/SiO$_2$ substrate, (a) Graphene coated Si/SiO$_2$ substrate (b) etching the unwanted graphene layer (c) Graphene channel on Si/SiO$_2$ substrate, (d) electrode deposition, and (e) electrode encapsulation.

The GFETs used in this study were fabricated from a predeposited graphene film on 300 nm $SiO_2$ coated Si substrate from ACS Suppliers, USA. The FETs consist of a channel with dimensions of 100 μm width and 40 μm length. The key steps involved in fabricating the GFET on a Si/$SiO_2$ substrate is schematically illustrated in FIG. 12. The source and drain electrodes were defined by photolithography and formed by successive deposition of Cr and Au. Both the drain and source electrodes were then encapsulated using AZ1518 photoresist and a channel with dimensions of 100 μm width and 10 μm length was left open to the environment for gating and functionalisation.

To fabricate GFETs, a wafer containing mechanically transferred CVD Graphene on 300 nm $SiO_2$/p-type Si substrate was purchased from Advanced Chemical Supplier, CA, USA. The wafer was first cleaved into squares chips with a dimension of 12 mm×12 mm. The chips were rinsed in acetone and IPA to remove the contaminants on the graphene surface. Then the alignment marker deposition was carried out by thermal evaporation using an Angstrom engineering—Nex Dep 200 evaporator. The devices were mounted on a rotating stage and the chromium and gold metal sources were loaded. Chrome plated tungsten rods (Kurt J. Lesker Company) were used as the chromium source. Pieces of gold wire (99.99%, Kurt J. Lesker Company) were loaded into a tungsten boat (Kurt J. Lesker Company) and loaded into the evaporation chamber. The chamber was evacuated to 2×10⁶ mTorr and 5 nm of chrome and 50 nm of gold was evaporated successively. The chamber was cooled down and vented with nitrogen. The lift-off was carried out by soaking the devices in acetone for 10 min and then washing in IPA before being dried with nitrogen. The channel area was defined using AZ1518 photoresist and the graphene film on the rest of the chip was etched using 200 W oxygen plasma at 600 mTorr for 1 min using a reactive ion etcher (Oxford instruments, Plasmalab 80 Plus). The top contacts were then deposited by successive thermal evaporation of 5 nm Cr and 50 nm Au after defining them by photolithography. The electrodes were encapsulated by AZ 1518 photoresist. The encapsulated graphene FETs were cleaned under 50 W oxygen plasma for one min at 200 mTorr pressure and 20 SCCM oxygen flow to remove the residual photoresist on the graphene channel. Then the devices were hard-baked at 200° C. for 10 min on a hotplate and washed in acetone and IPA before functionalisation.

1.4 Functionalisation of OrX and OrX/Orco Liposomes on GFETs

Figure 13:
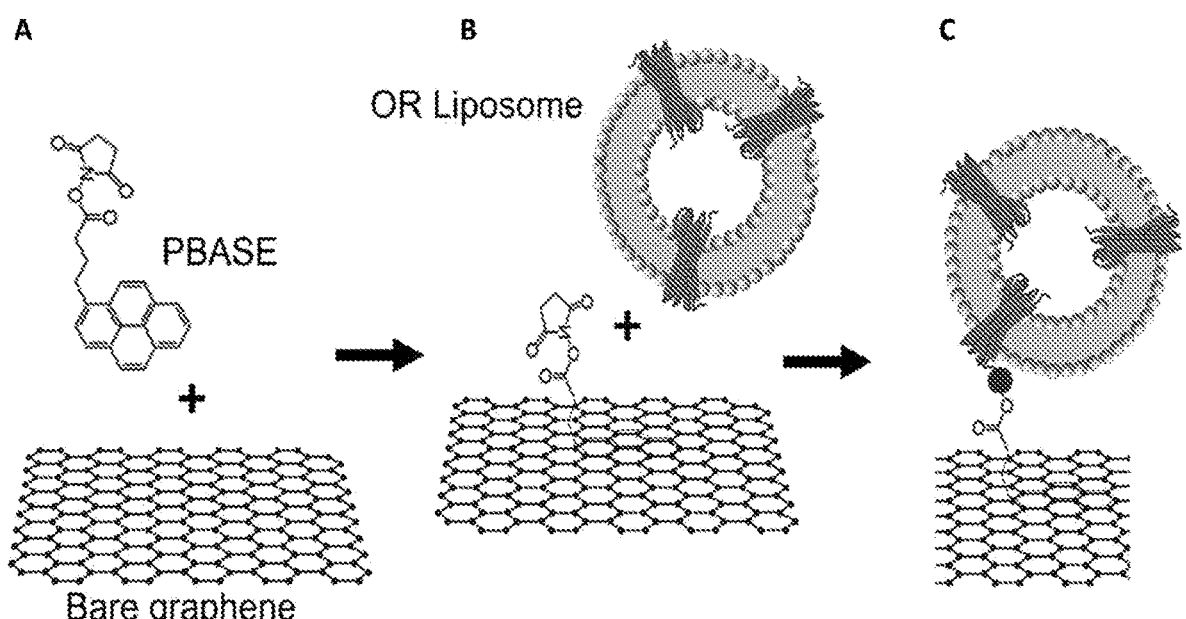
FIG. 13: Schematic of liposome immobilization on graphene (a) functionalization of PBASE on graphene using T-T interaction (b) incubation of PBASE functionalised CNT with liposomes (c) tethering of liposomes with PBASE using nucleophilic substitution reaction.

The OR liposomes were functionalised onto the graphene surface via a non-covalent route using PBASE as the molecular linker as shown in FIG. 13. The OR liposomes were diluted at 1:10 ratio with 1×PBS (pH7.4). The cleaned GFETs were immersed in 1 mM PBASE solution in methanol for 1 hour. The devices were washed three times in methanol and subsequently washed three times in 1×PBS to remove the excess PBASE and residual methanol in the channel respectively. The OR liposomes were diluted 1:10 with 1×PBS (pH 7.4) and 100 μL of the OR dilution was placed in the graphene channel and incubated at room temperature for one hour in a closed petri dish. After OR liposome functionalization, the devices were washed in 1×PBS for 10 s before measurements.

Figure 14:
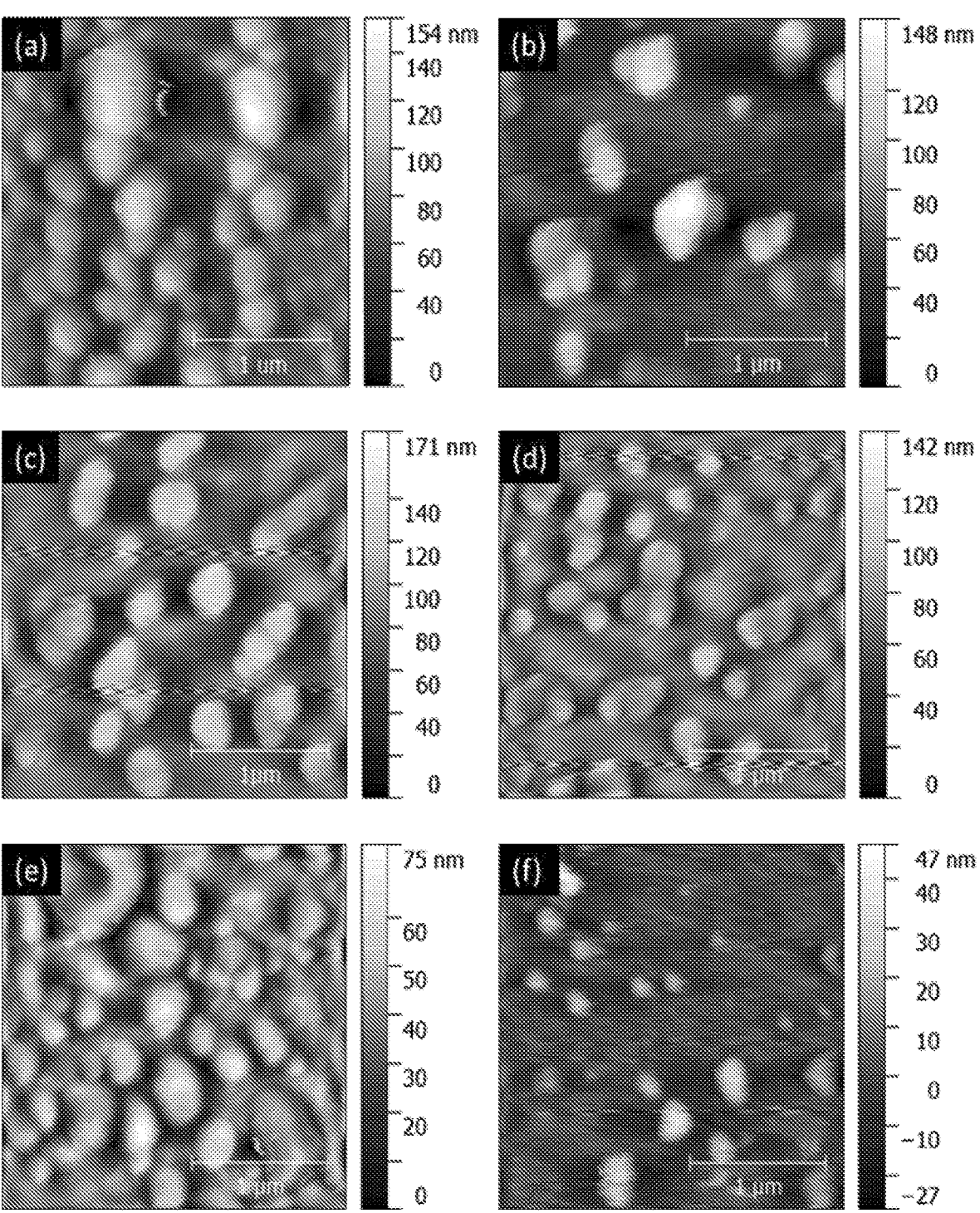
FIG. 14: AFM images of (a) Or10a liposomes, (b) Or10a/Orco liposomes, (c) Or22a liposomes, (d) Or22a/Orco liposomes, (e) empty liposomes and, (f) Orco liposomes, immobilised on a graphene channel.

The attachment of OR liposomes to the graphene surface was verified by AFM using a tabletop AFM (Nanosurf, NaioAFM). Imaging was carried out using tapping mode with dynamic applied force. AFM images after OR liposome functionalisation were carried out in air. The functionalised graphene FETs were washed in DI water and the excess water was drained. The functionalised devices were dried under a Nitrogen stream before imaging. Gwydion (V. 2.47) and SPIP software packages were used to analyse the AFM images. FIG. 14 shows Or10a, Or10a/Orco, Or22a, Or22a/Orco, empty liposomes and Orco liposomes immobilised on the graphene surface. The average size of the liposomes used in this study was estimated as 128±43 nm. The AFM images confirmed that the spherical structure of the liposomes was preserved after functionalisation.

1.4 Electrical Characterisation of OR Liposome GFETs

Figure 15:
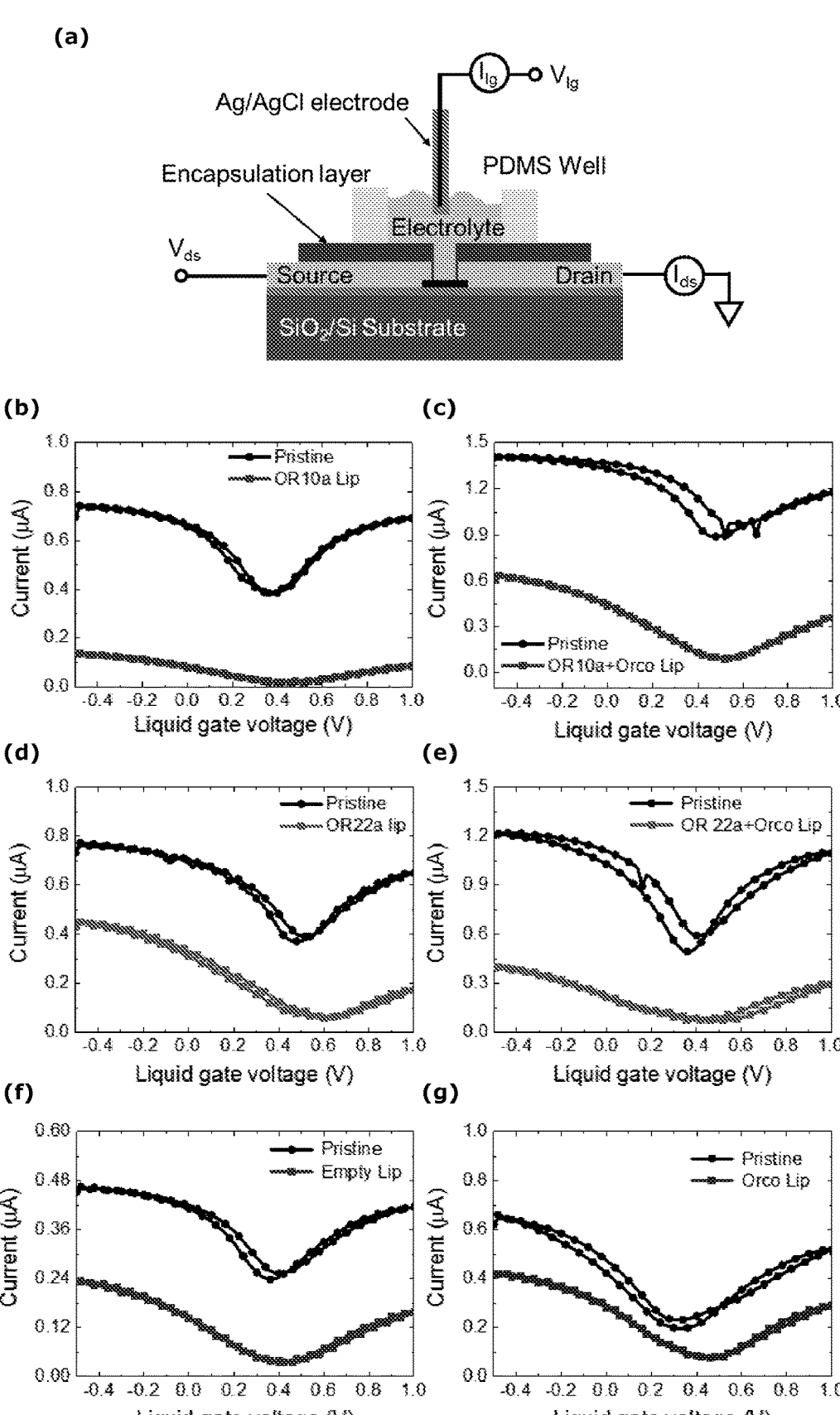
FIG. 15: GFET Device schematic and transfer characteristics. (a) Device schematic and circuit connections of a FET fabricated on a SiO$_2$/Si substrate with encapsulated source and drain electrodes for liquid gate measurements. (V$_{ds}$ was chosen at 100 mV for CNT network FETs and 1 mV for GFETs). Transfer characteristic curves of the actual GFETs before (circle) and after (square) functionalisation of (b) Or10a, (c) Or10a/Orco, (d) Or22a, (e) Or22a/Orco, (f) Empty and (g) Orco liposomes (V$_{ds}$ was kept at 1 mV for all the measurements).

Electrical sensor measurements of OR liposome functionalised GFETs were carried out using top liquid gate morphology as shown in the schematic in FIG. 15 (a). A PDMS well was used to constrain the electrolyte to the channel region. Devices were electrically characterized using an Agilent 4156C parameter analyser and a Rucker and Kolls probe station with micromanipulators. Ag/AgCl standard electrode was used as the gate electrode for liquid gate measurements. The transfer characteristics of the different graphene FETs (FIG. 15 (b) to (g)) were measured at $V_{ds}$=1 mV while the liquid gate voltage $V_{lg}$ was swept from −0.5 V to 1 V with an interval of 20 mV.

1.5 OR Liposome GFET Sensor Measurements

The OR liposome immobilised GFET device with a PDMS well mounted on it was placed onto the probe station and the source and drain connections were made by micromanipulators. 100 μl of PBS containing 1% dimethyl sulfoxide (DMSO) was added to the well and the Ag/AgCl standard electrode was placed into the buffer. The stock solution of ligands at 100 mM concentrations were prepared by dissolving them in DMSO as they are not stable in aqueous buffer. The stock solution was stored at 4° C. The ligand solution for sensing was prepared by diluting the stock solution in 1×PBS buffer containing 1% DMSO to set concentrations from 10 fM to 100 µM. The ligand solution was added to the PDMS well at three-minute intervals to make final concentrations from 1 fM to 10 µM. The real-time sensor measurement was carried out by continuously measuring the Ids at an interval of 1 s. The gate voltage $V_{lg}$ was maintained at 0 V throughout the measurement via the Ag/AgCl reference electrode.

2. Results

The sensing performance of OR liposome functionalised GFET sensors was tested. OR liposomes with and without the co-receptor Orco were used for sensing tests. Four sets of sensors were fabricated by immobilising Or10a, Or10a/Orco, Or22a and Or22a/Orco liposomes and tested.

Or10a and Or10a/Orco liposome sensors were tested against their positive ligand, methyl salicylate. Or22a and Or22a/Orco liposome sensors were tested against their positive ligand, methyl hexanoate. These sensors were also tested using E2-hexenal as a ligand control. The response of empty liposome and Orco liposome functionalised GFET sensors were tested against both methyl salicylate and methyl hexanoate as controls. Each experiment was carried out in triplicate to reduce the experimental and measurement errors.

Figure 16:
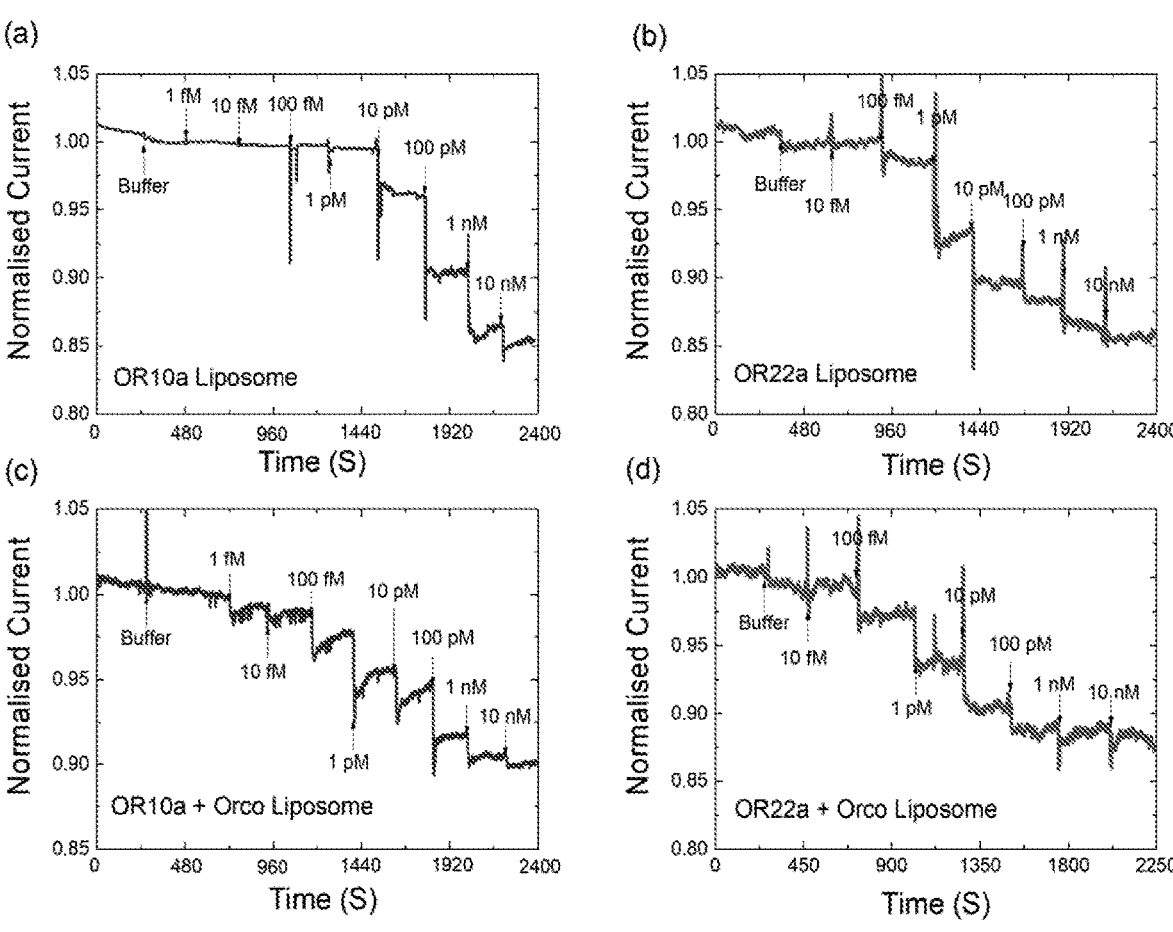
FIG. 16. Normalised real time sensing response of (a) Or10a and (b) Or22a, (c) Or10a+Orco and (d) Or22a+Orco liposome immobilised GFET sensors with the addition of increasing concentrations of target ligands (Or10a—methyl salicylate (MeSal), Or22a—methyl hexanoate (MeHex)).
Figure 17:
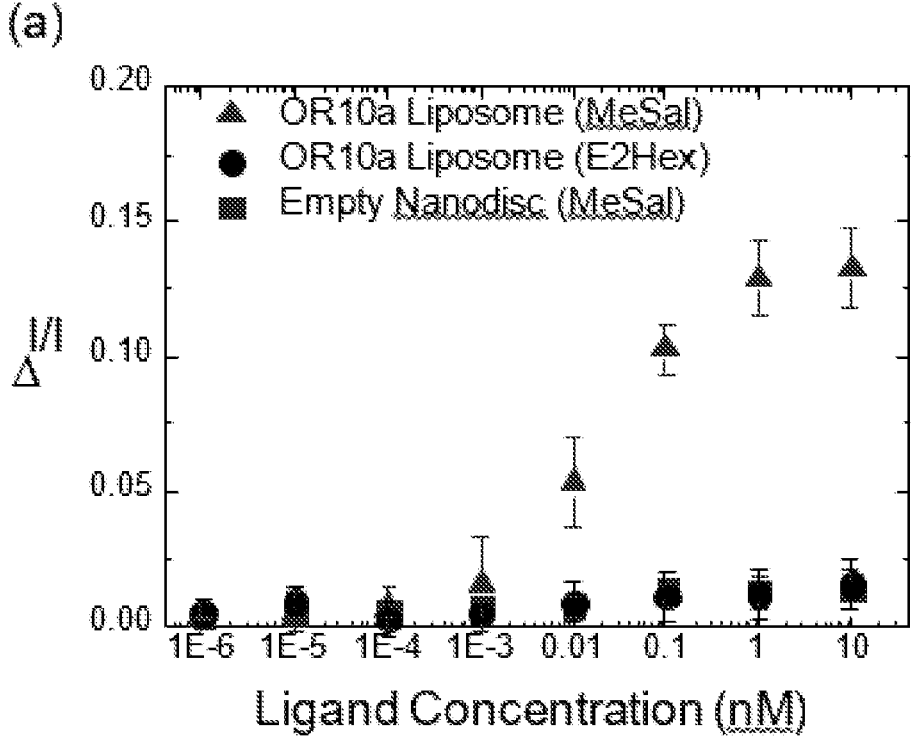
FIG. 17. Normalized dose response curves for target ligands (Or10a—methyl salicylate (MeSal), Or22a—methyl hexanoate (MeHex)) and control ligands (Or10a and Or22a —E2-hexenal (E2Hex)) with (a) Or10a, (b) Or10a+Orco, (c) Or22a, and (d) Or22a+Orco liposomes. The lack of response from empty liposomes (a, c) and Orco only liposomes (b, d) to the target ligands are also shown. For both Or22a (e) AND Or10a (f) there can be seen a shift to the left for their respective dose-response curves when Orco is present in the liposomes.
Figure 17:
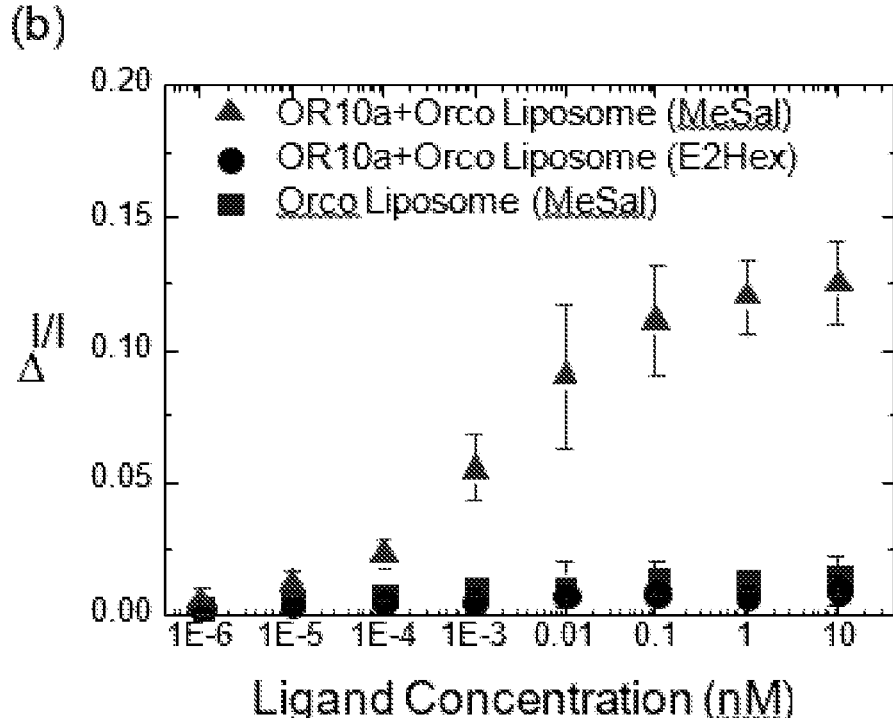
Figure 17:
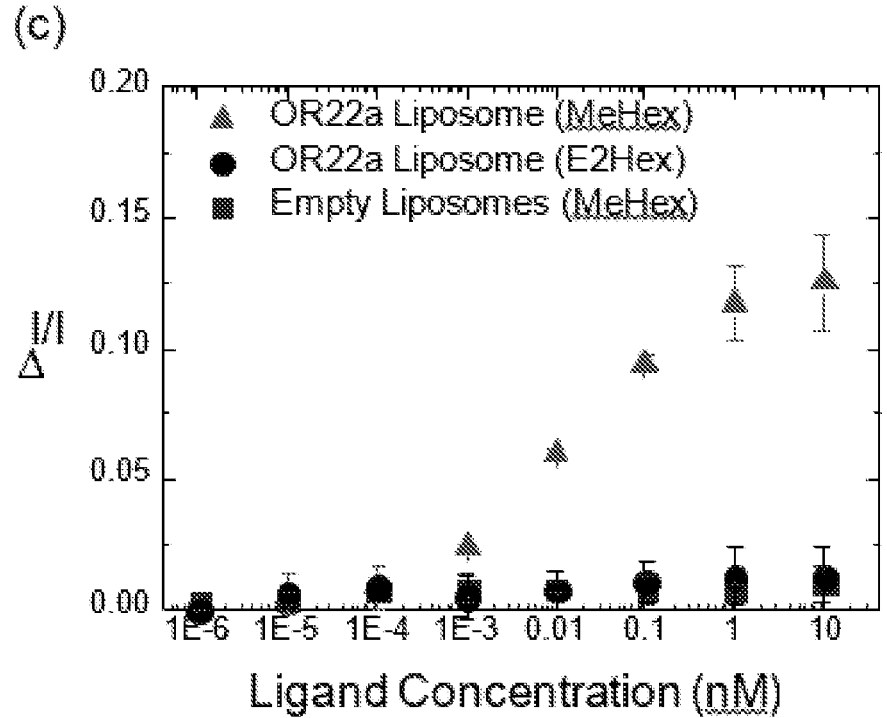
Figure 17:
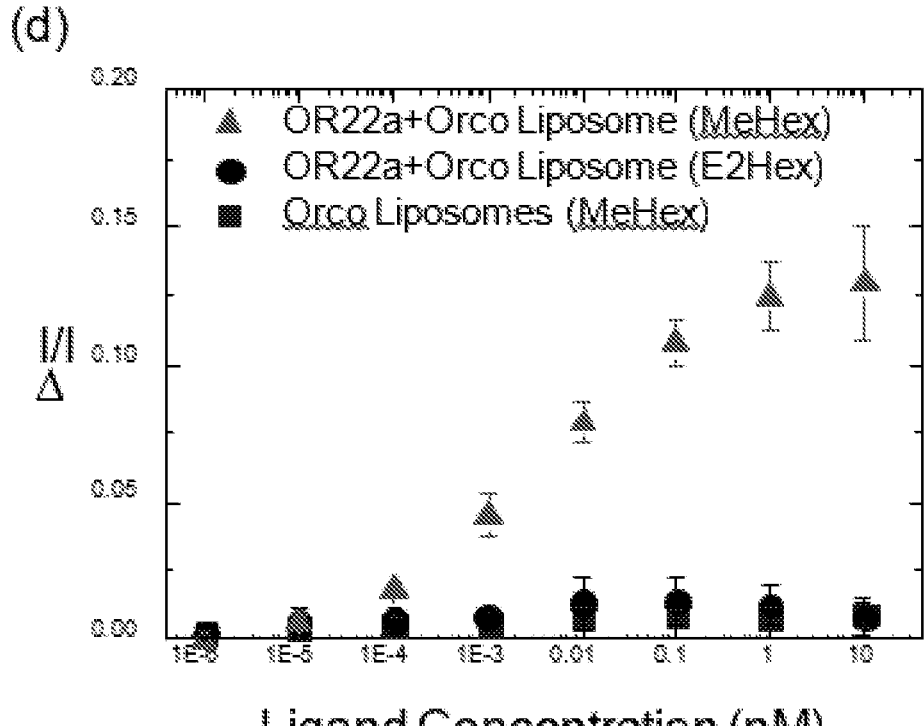
Figure 17:
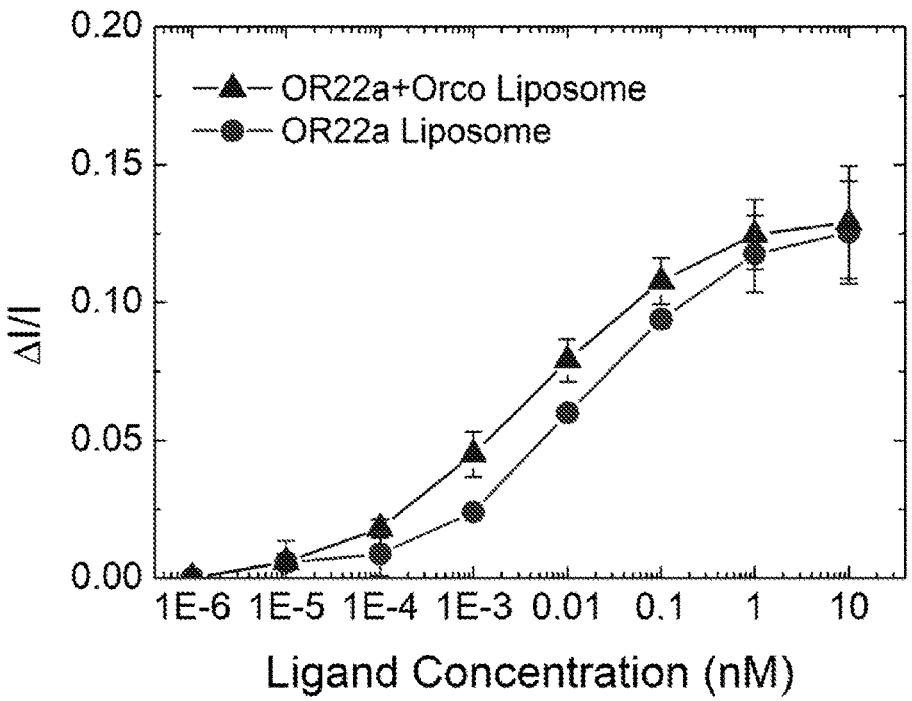
Figure 17:
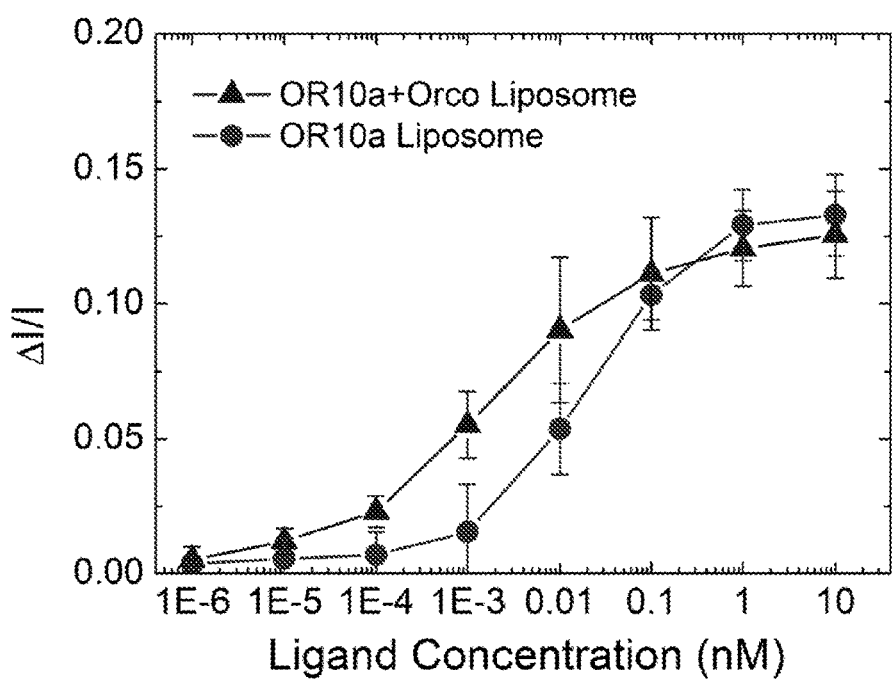

FIG. 16 shows the normalised real time sensing response of all four sensors with the addition of increasing concentrations of their positive ligands. It shows that each of the liposome based sensors with and without Orco produced a dose dependent response specific to the positive ligand and not to the control ligand. Neither empty liposomes nor Orco containing liposomes respond to the positive ligands confirming selective binding is due to the presence of the OrX. FIG. 17 summarises the effect of the presence of Orco on the response of each OrX to its positive ligand. The presence of Orco results in an increase in sensitivity as demonstrated by the shift of their dose response curves to the left and the lowering of their LODs from pM to 100 fM levels. Table 4 summarises the Ec50 and detection range for the OrX and OrX/Orco combinations.

tronic response to target ligands are observed. This confirms that although Orco is not directly involved in ligand binding, its presence in the liposomes further attenuates the sensitivity of the OrX to its target ligand.

EXAMPLE 5—EXEMPLIFICATION OF THE BILAYER SENSOR DEVICE WITH DROPLET INTERFACE BILAYERS (DIBS)

Summary

The applicants have shown that functional ionotropic olfactory receptors (ORs) have been incorporated into proteoliposomes and fused with artificial bilayers where the reversible binding of an odorant can be measured electrically.

1. Experimental Methods 1.1 Materials

Phosphate buffer saline (PBS) tablets, methyl salicylate, and methyl hexanoate were obtained from Sigma-Aldrich. All lipids were sourced from Avanti polar lipids. All other chemicals were purchased from Merck, UK, unless otherwise specified. Double-distilled 'ultrapure' water (Millipore, Milli-Q:18.2 MΩ cm) was used throughout.

1.2 Preparation of Purified OrX and Orco Subunits

OrX and Orco subunits were prepared as described in Example 1 section 1.2 with the following alteration:

Following the resuspension of the membrane pellet, the sample was centrifuged at 100,000 g for 1 h at 4° C. rather than 18° C.

1.3 Preparation of OR Associated Liposomes

OR associated liposomes were prepared as described in Example 1 section 1.3 with the following alteration:

The incubation step with Bio-Beads was performed overnight.

1.4 Preparation of Lipid Droplets

DPhPC (Avanti, 4ME 16:0 PC) was dissolved in chloroform and aliquoted before dried under a stream of nitrogen to form a thin lipid film. This was then placed in a desiccator under vacuum for 14 hours Aliquots were then stored under argon at <−20° C. Before use, undecane (Merck, UK) was added to dissolve the lipid to make a solution of 10 mg/ml. This was diluted in AR20 silicone oil (Merck, UK) and

TABLE 4

| Dose response equation, $EC_{50}$ and detection ranges of OrX and OrX/Orco based GFET biosensors. | | | | |
|---|---|---|---|---|
| Receptor | Analyte | Dose Response Equation | $EC_{50}$ | Detection Range |
| Or10a | Methyl salicylate | $y = 0.138 \times 4.62 \times 10^6 \times x^{1-0.38}/15.56 \times 10^{-12}$ M $1 + 4.62 \times 10^6 \times x^{1-0.38}$ | | $10^{-12}$ to $10^{-8}$ M |
| Or10a/Orco | Methyl salicylate | $y = 0.129 \times 1.45 \times 10^5 \times x^{1-0.56}/2.07 \times 10^{-12}$ M $1 + 1.45 \times 10^5 \times x^{1-0.56}$ | | $10^{-13}$-$10^{-8}$ M |
| Or22a | Methyl hexanoate | $y = 0.12 \times 2.73 \times 10^6 \times x^{1-0.41}/12.09 \times 10^{-12}$ M $1 + 2.73 \times 10^6 \times x^{1-0.41}$ | | $10^{-12}$ to $10^{-8}$ M |
| Or22a/Orco | Methyl hexanoate | $y = 0.131 \times 4.02 \times 10^6 \times x^{1-0.5}/3.91 \times 10^{-12}$ M $1 + 4.02 \times 10^6 \times x^{1-0.5}$ | | $10^{-13}$-$10^{-8}$ M |

3. Conclusions

This study has demonstrated the improved sensitivity of both Or10 and Or22a in the presence of Orco in olfactory biosensors based on GFET devices. Both, Or10a and Or22a embedded with the Orco subunit in liposomes which are functionalized on graphene show an increased sensitivity (fM) when compared with the receptors on their own in liposomes. Compared with results from empty liposomes and Orco liposomes functionalized graphene, no clear elecundecane (to make a final AR20 silicone oil undecane ratio 1:1) to make a 1 mg/ml solution. Undecane and AR20 silicone oil was prefiltered using a 0.22 µm filter before use.

1.5 Electrode Preparation

Silver electrodes (0.5 mm diameter, >99% purity, Merck) were cut to appropriate lengths and prepared with fine grit sandpaper before incubated in sodium hypochlorite solution (Fluka, UK) for 1 hour. The electrodes were then washed in ddH$_2$O before inserted into the electrophysiology array wells or affixed to the manipulator.

1.6 Electrophysiology Array

Figure 18:
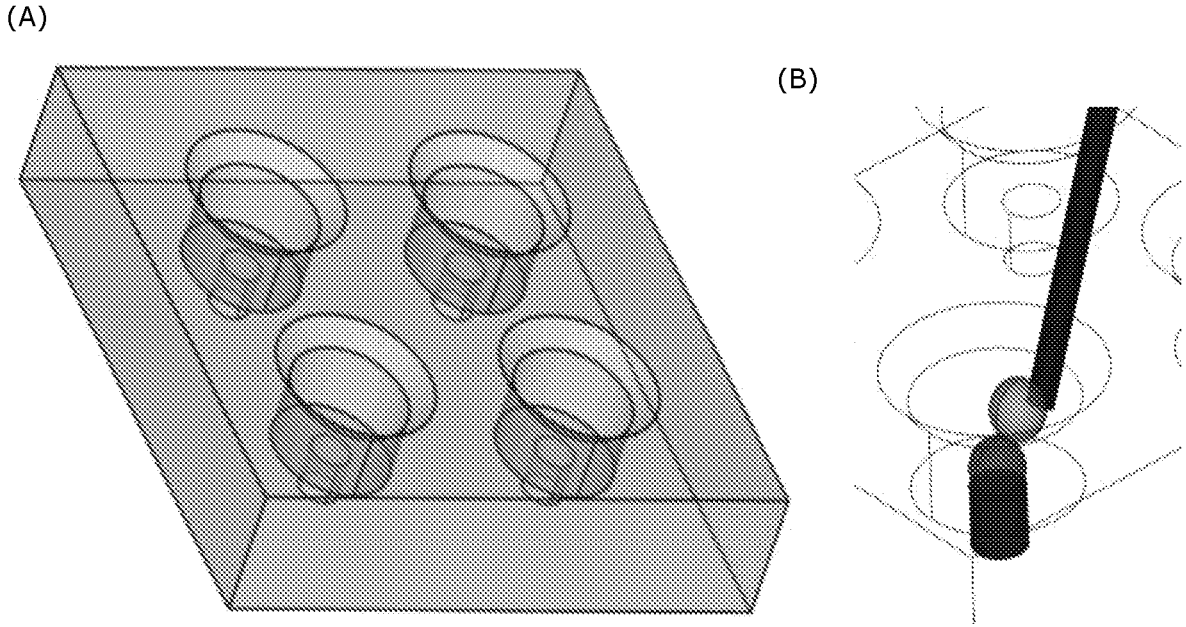
FIG. 18. Overview of PMMA platform used for the bilayer sensor device. (A) 4-chamber design of array. (B) Schematic of droplet interface bilayer (DIB) formation between droplets (red and green) deposited on the base and manipulator electrode (blue) the original PMMA shape. The PMMA shape is shown as fully transparent to adequately display the position of the electrodes within the shape.

A multiwell array made from poly(methyl methacrylate) (PMMA) was designed using computer assisted design software (FreeCAD, https://www.freecadweb.org/) and milled using a subtractive computerized numerical control (CNC) machine (Roland Modela MDX-40A). FIG. 18 shows an overview of this PMMA platform. (A) shows the 4-chamber design of array. (B) shows a schematic of DIB formation between droplets (red and green) deposited on the base and manipulator electrode (blue) the original PMMA shape.

The PMMA shape is shown as fully transparent to adequately display the position of the electrodes within the shape.

1.7 Electrophysiology Setup

The electrophysiological recordings were taken using Pico2 (Tecella, USA) amplifier within a faraday cage containing.

1.8 Droplet Interface Bilayer Formation

Bilayers were formed between two droplets formed within a PMMA chamber filled with 1 mg/ml DPhPC in undecane and AR20 silicone oil (1:1 ratio). The first step in this process was to deposit a 50 nl droplet onto the stationary silver electrode positioned at the base of the well; this droplet consisted of an aqueous solution containing 300 mM NaCl, 10 mM HEPES (pH 7.4), containing the odorant receptor proteins in proteoliposomes (at a 1:20 dilution from the proteoliposome preparation), and 0.1-1 μM of the odorant. The second droplet was mounted onto a second silver electrode which was held in the oil and lipid mixture using a YOU-3 manipulator (Narishige, Japan). The second droplet had a total volume of 50 nl containing 50 mM NaCl and 10 mM HEPES (pH 7.4). Both droplets were deposited using a 0.5 μl syringe (Hamilton, USA). To ensure that a stable phospholipid monolayer had formed around each droplet, the droplets were left on the electrodes for 5 min before being gently brought together using the YOU-3 manipulator. Once the droplets were in contact a bilayer formed spontaneously within 1 minute (as determined by visual assessment and an increase in the bilayer capacitance as measured with a capacitance voltage protocol using the Pico2 amplifier). Insertion of an active channel was determined by a change in current while clamping the voltage at 50 mV. This process took up to 45 min. If no insertion was seen at this point the experiment was discarded. Droplet interface bilayer experiments were conducted at 22.0±1.5° C.

1.9 Recording Parameters

Currents were recorded with a Pico2 or an eONE-HS amplifier (Tecella, USA and Elements, Italy, respectively) with built-in digitizers, operating in gap-free acquisition mode at a sampling frequency of 20 kHz, and using a 0.8 or 1.5 kHz low pass filter. All experiments were conducted using the voltage-clamp approach. The voltage across the membrane was clamped at various potentials, ranging from −200 mV to 200 mV.

1.10 Manual Data Analysis

Data were analysed using ANA (Dr Pusch, Genoa), EDR (Elements, Italy) and WinWCP (Dr Dempster, University of Strathclyde). Single channel currents were measured as step increases in the amplitude of the current observed. When measuring the current at different holding potentials the baseline current might be at a different level. To compensate for this, the change in current is given in relation to the baseline, as is common practice. At holding potentials below the electrochemical equilibrium value, the channel openings are shown as downward deflections. Inversely, channel openings are shown as upward deflections from the baseline when the holding potential is greater than the reversal potential.

2. Results

Figure 19:
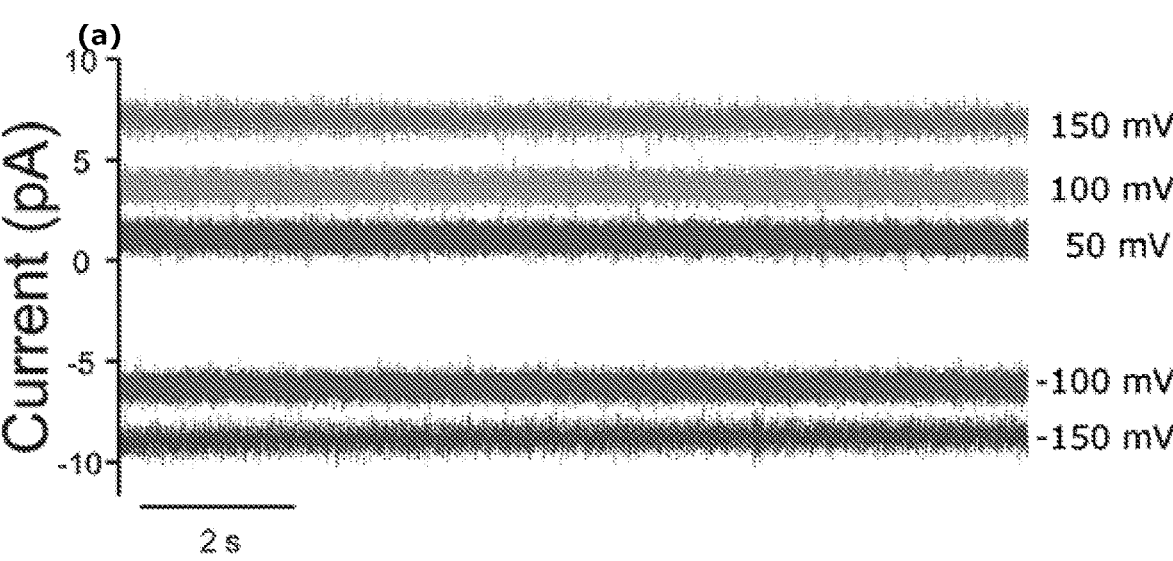
FIG. 19. Ion channel recordings from droplet interface bilayers (DIBs) containing (a) Or22a or (b) Or22a/Orco, and 10 mM methyl hexanoate, a known activator of Or22a. The DIB was formed between two aqueous droplets in a 1:1 undecane silicone oil mixture containing 1 mg/ml DPhPC, and the ion channel formation measured using the floating electrode set-up. The holding potential was varied as indicated. The reversal potential for Na$^+$ is 46 mV for the above experiments. Data was sampled at 10 kHz and filtered at 0.8 kHz.
Figure 19:
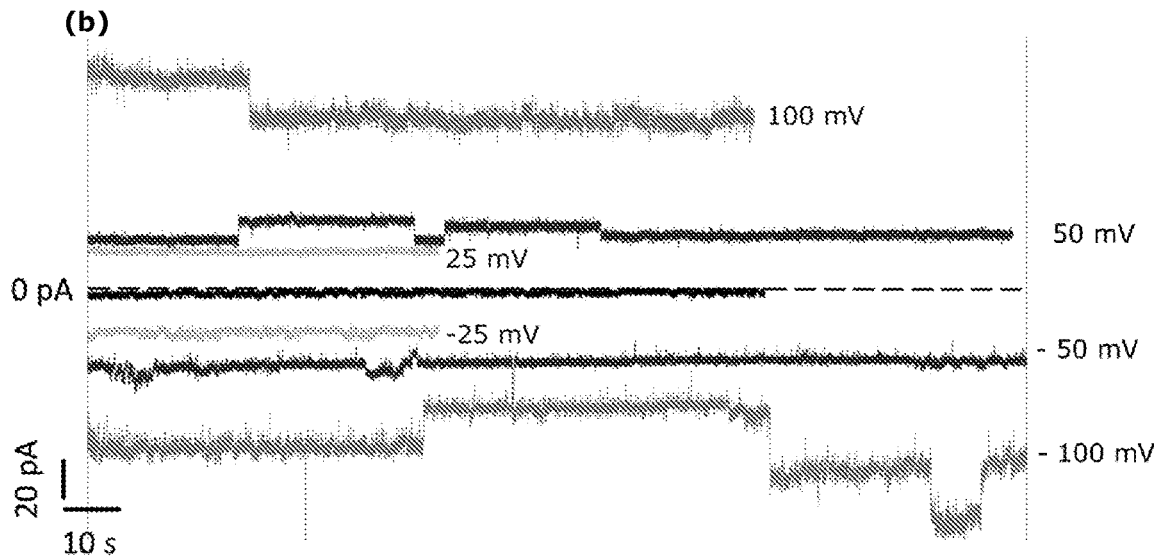
Figure 20:
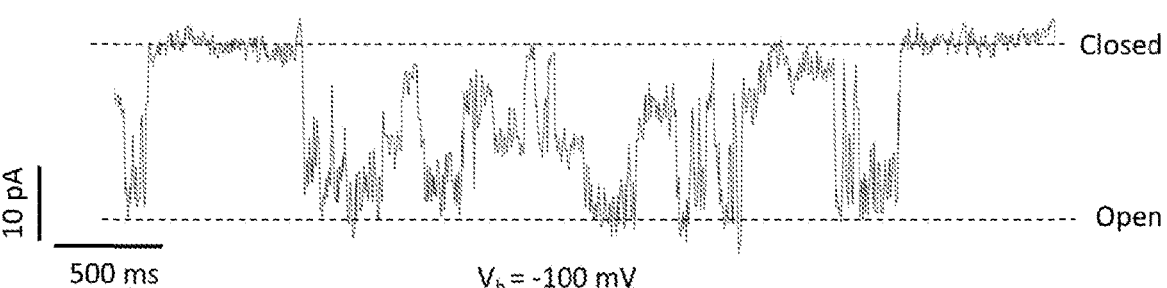
FIG. 20. Ion channel recording from a droplet interface bilayer (DIB) containing Or22a/Orco, and 10 μM methyl hexanoate. The DIB was formed between two aqueous droplets in a 1:1 undecane silicone oil mixture containing 1 mg/ml DPhPC, and the ion channel formation measured using the floating electrode set-up. The reversal potential for Na$^+$ is 46 mV for this experiment and the holding potential was −100 mV. Data was sampled at 10 kHz and filtered at 0.8 kHz.

FIG. 19 shows ion channel recordings from droplet interface bilayers (DIBs) formed between two aqueous droplets in a 1:1 undecane silicone oil mixture containing 1 mg/ml DPhPC, as measured using a floating electrode set-up (see FIG. 18). Proteoliposomes containing Or22a only (FIG. 19a) and Or22a/Orco (FIG. 19b) were fused with the DIBs to allow insertion of the receptor subunits. The solutions used contains 10 mM HEPES (pH 7.4 with NaOH), either 300 mM NaCl or 50 mM NaCl, supplemented with 10 μM Methyl hexanoate, a known Or22a agonist. For the Or22a only DIB experiment (FIG. 19a) the holding potential was varied between +/−150 mV, +/−100 mV, and +/−50 mV. No ion channel activity is observed at any holding potential indicating that Or22a cannot form an active ion channel on its own. For the Or22a/Orco DIB experiment (FIG. 19b) the holding potential was varied between +/−100 mV, +/−50 mV and +/−25 mV. In this case ion channel activity is observed at +/−100 mV, +/−50 mV and −25 mV indicating that Or22a can form an active ligand gated ion channel when combined with Orco. FIG. 20 shows a second independent Or22a/Orco DIB experiment acquired at a holding potential of −100 mV. In this case multiple open states can be identified, likely due to the insertion of multiple Or22a/Orco channel complexes.

Figure 21:
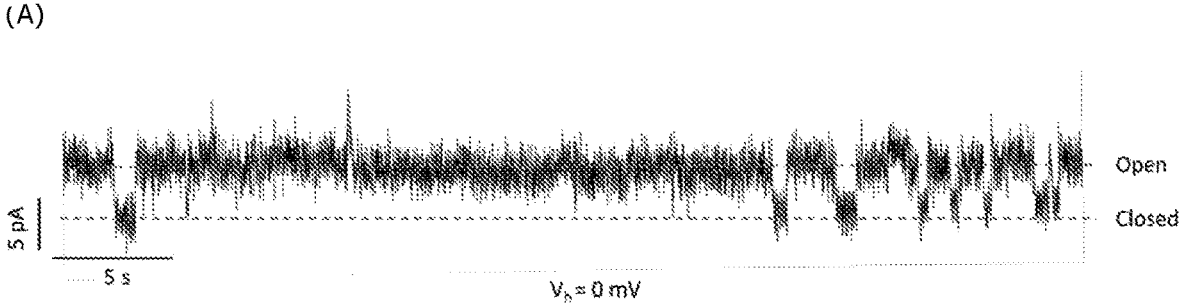
FIG. 21. (A) Ion channel recording from a droplet interface bilayer (DIB) containing Or71a, Orco, and 10 μM 4-ethyl guaiacol, a known Or71a agonist. The DIB was formed between two aqueous droplets in a 1:1 undecane silicone oil mixture containing 1 mg/ml DPhPC, as measured using the floating electrode set-up. The reversal potential for Na$^+$ is −46 mV for this experiment. Data was sampled at 10 kHz and filtered at 0.8 kHz. (B) A second ion channel recording, as described in (A).
Figure 21:
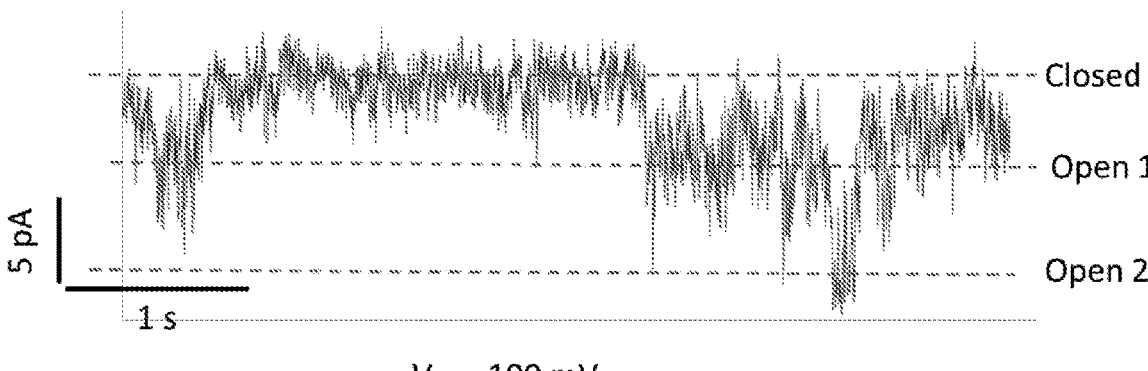

FIG. 21 shows two ion channel recordings from droplet interface bilayers (DIBs) formed between two aqueous droplets in a 1:1 undecane silicone oil mixture containing 1 mg/ml DPhPC, as measured using a floating electrode set-up (see FIG. 18) at a holding potential of 0 mV (FIG. 21a) and −100 mV (FIG. 21b). Proteoliposomes containing Orco/Or71a were fused with the DIB to allow insertion of the receptor subunits. The solutions used contains 10 mM HEPES (pH 7.4 with NaOH), either 300 mM NaCl or 50 mM NaCl, supplemented with 10 μM of the target ligand 4-ethyl guaiacol. Both DIB experiments show that Or71a in the presence of Orco can form an active ligand gated ion channel.

3. Conclusions

This study has further confirmed that the presence of Orco affects the sensitivity of OrXs in olfactory biosensors based on electronic device platforms. In this case, when two OrXs (Or22a and Or71a) are inserted independently with the Orco subunit into lipid bilayers both OrX/Orco complexes exhibit ion channel activity in the presence of a target ligand for the OrX. However in the absence of Orco this ligand gated activity is not exhibited highlighting the role of Orco in forming an active ion channel. This data demonstrates the potential to use OrX/Orco complexes in lipid bilayer based sensor devices to detect specific volatile organic compounds based on their ion channel activity response.

EXAMPLE 6—EXEMPLIFICATION OF THE SENSOR WITH SURFACE PLASMON RESONANCE IMAGING

Summary

The applicants describe a convenient SPRi sensor device using insect odorant receptor (OrX) subunits embedded in the membrane mimic including liposomes and nanodiscs in the absence and presence of the Orco sequence. Each of the OrX functionalized SPR sensors show a clear electronic response to its target ligand. The presence of Orco in the membrane mimic has an additive, or amplifying, effect on the OrX response, increasing the sensitivity of the OrX for its target ligand. The specificity of the binding is verified by testing each OrX and OrX/Orco functionalized SPRi sensors response to non-responding ligands.

1. Experimental Methods 1.2 Preparation of OR Associated Liposomes and Nanodiscs 1.2.1 Preparation of Purified OR Subunits OrX and Orco subunits are prepared as described in Example 1 section 1.2. OrX and Orco subunits have a Cysteine residue engineered at their N termini to enable their direct coupling to the gold surface of an SPRi prism.

1.2.2 Preparation of OR Associated Liposomes

OrX and Orco liposomes are prepared as described in Example 1 section 1.3

1.2.3 Preparation of OR Associated Nanodiscs

Nanodiscs are prepared using a protocol modified from Bayburt et al. 2010 and 200355[55, 56]. Nanodiscs were formed at an MSP:protein:lipid ratio of 1:0.2:150. The required amount of lipid is removed from the 100 mg/mL stock and dried under a constant stream of nitrogen gas, then further dried under vacuum overnight. The lipids are resuspended in the required volume of buffer (20 mM Tris/HCl pH 7.5, 100 mM NaCl, 50 mM sodium cholate) and sonicated, resulting in a clear lipid stock at 20 mg/mL concentration. Purified odorant receptor protein in detergent buffer is mixed with the MSP1E3D1 and POPC lipid at the required ratio and incubated on ice for 1 hour. To initiate the reconstitution by removing detergents from the system, Bio-beads SM2 (Bio-Rad #1523920) are added to the sample at a 1:1 weight:volume ratio and the mixture is incubated at 4° C. overnight with constant rotation. Bio-beads are then removed and the incorporated nanodiscs are frozen at −80° C. until required.

1.3 Preparation of OrX and OrX/Orco SPRi Sensors

OrX and OrX/Orco in liposomes or nanodiscs are immobilised as defined spots onto the gold surface of an SPRi prism according to the protocol used by Hurot et al. 2019 for the immobilisation of vertebrate odorant binding proteins (OBPs)[57]. OrX and OrX/Orco complexes are immobilised directly via the N-terminal Cysteine residue. Immobilisation occurs at an appropriate density to ensure a self-assembly of liposomes or nanodiscs on the gold surface that yields a liposome or nanodisc monolayer. This prevents the formation of additional disordered layers of liposomes or nanodiscs which prevent target ligands accessing the binding pockets of OrXs or OrX/Orco complexes directly attached to the gold layer. A monolayer that completely covers the gold surface is obtained to block non-specific binding of target ligands to the gold surface.

1.4 Detection and Analysis of Ligand Binding by OrX and OrX/Orco SPRi Sensors

The binding of VOCs to OrX and OrX/Orco liposomes or nanodiscs are detected using an appropriate SPRi apparatus and analysed as described by Hurot et al. 201957. The OrX or OrX/Orco immobilised gold surface is exposed to different concentrations (fM to nM) of target ligand or control ligand. Ligand binding is measured as a change reflectivity as compared to the baseline prior to addition of the ligand. Each experiment is carried out in triplicate to reduce the experimental and measurement errors.

2. Results

The sensing performance of OrX and OrX/Orco liposome or nanodisc functionalised SPRi sensors are tested against a positive ligand specific to the OrX subunit and a control ligand to which the OrX should not bind. The response of empty liposome and Orco liposomes, or empty nanodiscs and Orco nanodiscs functionalised SPRi sensors are also tested against the positive ligand.

In the case of both membrane display formats, the OrX subunit on its own binds sensitively to the positive ligand producing a dose response curve, but does not respond to the control ligand. When the Orco subunit is also present, the presence of Orco is expected to result in an increase in sensitivity as demonstrated by the shift of their dose response curves to the left and the lowering of their LODs. Neither empty liposomes nor Orco containing liposomes respond to the positive ligands confirming selective binding is due to the presence of the OrX.

3. Conclusions

This study is expected to demonstrate the improved sensitivity of OrXs in the presence of Orco in olfactory biosensors based on SPRi devices. It is believed that OrXs embedded with the Orco subunit in liposomes or nanodiscs which are functionalized on the gold surface of an SPRi glass prism will show an increased sensitivity when compared with the OrX receptors on their own. Compared with results from empty liposomes or nanodiscs and Orco containing liposomes or nanodiscs, respectively, no clear electronic response to target ligands are observed. This is expected to confirm that although Orco is not directly involved in ligand binding, its presence in the liposomes further attenuates the sensitivity of the OrX to its target ligand.

REFERENCES

1. Montagne, N.; de Fouchier, A.; Newcomb, R. D.; Jacquin-Joly, E., Advances in the identification and characterization of olfactory receptors in insects. *Progress in molecular biology and translational science* 2015, 130, 55-80.
2. Leary, G. P.; Allen, J. E.; Bunger, P. L.; Luginbill, J. B.; Linn, C. E., Jr.; Macallister, I. E.; Kavanaugh, M. P.; Wanner, K. W., Single mutation to a sex pheromone receptor provides adaptive specificity between closely related moth species. *Proc Natl Acad Sci* 2012, 109 (35), 14081-6.
3. Kiely, A.; Authier, A.; Kralicek, A. V.; Warr, C. G.; Newcomb, R. D., Functional analysis of a *Drosophila melanogaster* olfactory receptor expressed in Sf9 cells. *J. Neurosci. Methods* 2007, 159 (2), 189-94.
4. Jordan, M. D.; Anderson, A.; Begum, D.; Carraher, C.; Authier, A.; Marshall, S. D.; Kiely, A.; Gatehouse, L. N.; Greenwood, D. R.; Christie, D. L.; Kralicek, A. V.; Trowell, S. C.; Newcomb, R. D., Odorant receptors from the light brown apple moth (*Epiphyas postvittana*) recognize important volatile compounds produced by plants. *Chem. Senses* 2009, 34 (5), 383-94.
5. Anderson, A. R.; Wanner, K. W.; Trowell, S. C.; Warr, C. G.; Jaquin-Joly, E.; Zagatti, P.; Robertson, H.; Newcomb, R. D., Molecular basis of female-specific odorant responses in *Bombyx mori*. *Insect Biochem. Mol. Biol.* 2009, 39 (3), 189-97.
6. Corcoran, J. A.; Jordan, M. D.; Carraher, C.; Newcomb, R. D., A novel method to study insect olfactory receptor function using HEK293 cells. *Insect Biochem. Mol. Biol.* 2014.
7. Jones, P. L.; Pask, G. M.; Rinker, D. C.; Zwiebel, L. J., Functional agonism of insect odorant receptor ion channels. *Proc. Natl. Acad. Sci. USA* 2011, 108 (21), 8821-5.
8. WO2000US4995—Genes encoding insect odorant receptors and uses thereof.
9. WO2002US5414—Chemosensory gene family encoding gustatory and olfactory receptors and uses thereof.

10. WO2004US42372—In vivo odorant receptor systems and their uses.
11. WO2000US1823—Novel odorant receptors in *Drosophila*.
12. WO2002US9559—Efficient methods for isolating functional G-protein coupled receptors and identifying active effectors and efficient methods to isolate proteins involved in olfaction and efficient methods to isolate and identifying active effectors.
13. WO2012US34847—Composition for inhibition of insect sensing.
14. Misawa, N.; Mitsuno, H.; Kanzaki, R.; Takeuchi, S., Highly sensitive and selective odorant sensor using living cells expressing insect olfactory receptors. *Proc. Natl. Acad. Sci. U.S.A* 2010, 107 (35), 15340-4.
15. Mitsuno, H.; Sakurai, T.; Namiki, S.; Mitsuhashi, H.; Kanzaki, R., Novel cell-based odorant sensor elements based on insect odorant receptors. *Biosens. Bioelectron.* 2015, 65, 287-294.
16. Smart, R.; Kiely, A.; Beale, M.; Vargas, E.; Carraher, C.; Kralicek, A. V.; Christie, D. L.; Chen, C.; Newcomb, R. D.; Warr, C. G., *Drosophila* odorant receptors are novel seven transmembrane domain proteins that can signal independently of heterotrimeric G proteins. *Insect Biochem. Mol. Biol.* 2008, 38 (8), 770-80.
17. Carraher, C.; Dalziel, J.; Jordan, M. D.; Christie, D. L.; Newcomb, R. D.; Kralicek, A. V., Towards an understanding of the structural basis for insect olfaction by odorant receptors. *Insect Biochem. Mol. Biol.* 2015, 66, 31-41.
18. Hopf, T. A.; Morinaga, S.; Ihara, S.; Touhara, K.; Marks, D. S.; Benton, R., Amino acid coevolution reveals three-dimensional structure and functional domains of insect odorant receptors. *Nature communications* 2015, 6, 6077.
19. Robertson, H. M.; Warr, C. G.; Carlson, J. R., Molecular evolution of the insect chemoreceptor gene superfamily in *Drosophila melanogaster. Proc. Natl. Acad. Sci. U.S.A.* 2003, 100, 14537-14542.
20. Hallem, E. A.; Carlson, J. R., Coding of odors by a receptor repertoire. *Cell* 2006, 125 (1), 143-160.
21. Silbering, A. F.; Rytz, R.; Grosjean, Y.; Abuin, L.; Ramdya, P.; Jefferis, G. S.; Benton, R., Complementary function and integrated wiring of the evolutionarily distinct *Drosophila* olfactory subsystems. *J. Neurosci.* 2011, 31 (38), 13357-75.
22. Boyle, S. M.; McInally, S.; Ray, A., Expanding the olfactory code by in silico decoding of odor-receptor chemical space. *eLife* 2013, 2, e01120.
23. Hill, C. A.; Fox, A. N.; Pitts, R. J.; Kent, L. B.; Tan, P. L.; Chrystal, M. A.; Cravchik, A.; Collins, F. H.; Robertson, H. M.; Zwiebel, L. J., G protein-coupled receptors in *Anopheles gambiae. Science* 2002, 298 (5591), 176-8.
24. Carey, A. F.; Wang, G. R.; Su, C. Y.; Zwiebel, L. J.; Carlson, J. R., Odorant reception in the malaria mosquito *Anopheles gambiae. Nature* 2010, 464 (7285), 66-U77.
25. Wang, G. R.; Carey, A. F.; Carlson, J. R.; Zwiebel, L. J., Molecular basis of odor coding in the malaria vector mosquito *Anopheles gambiae. Proc Natl Acad Sci USA* 2010, 107 (9), 4418-4423.
26. Jones, W. D.; Nguyen, T. A.; Kloss, B.; Lee, K. J.; Vosshall, L. B., Functional conservation of an insect odorant receptor gene across 250 million years of evolution. *Curr. Biol.* 2005, 15 (4), R119-21.
27. Pitts, R. J.; Fox, A. N.; Zwiebel, L. J., A highly conserved candidate chemoreceptor expressed in both olfactory and gustatory tissues in the malaria vector *Anopheles gambiae. Proc. Natl. Acad. Sci. U.S.A* 2004, 101 (14), 5058-63.
28. Carraher, C.; Nazmi, A. R.; Newcomb, R. D.; Kralicek, A., Recombinant expression, detergent solubilisation and purification of insect odorant receptor subunits. *Protein Expr. Purif.* 2013, 90 (2), 160-9.
29. Matsubara, Y.; Murakami, Y.; Kobayashi, M.; Morita, Y.; Tamiya, E., Application of on-chip cell cultures for the detection of allergic response. *Biosens. Bioelectron.* 2004, 19 (7), 741-7.
30. Figueroa, X. A.; Cooksey, G. A.; Votaw, S. V.; Horowitz, L. F.; Folch, A., Large-scale investigation of the olfactory receptor space using a microfluidic microwell array. *Lab on a chip* 2010, 10 (9), 1120-7.
31. Hossein-Babaei, F.; Paknahad, M.; Ghafarinia, V., A miniature gas analyzer made by integrating a chemoresistor with a microchannel. *Lab on a chip* 2012, 12 (10), 1874-80.
32. Hossein-Babaei, F.; Ghafarinia, V., Gas analysis by monitoring molecular diffusion in a microfluidic channel. *Anal. Chem.* 2010, 82 (19), 8349-55.
33. Lee, S. H.; Lim, J. H.; Park, J.; Hong, S.; Park, T. H., Bioelectronic nose combined with a microfluidic system for the detection of gaseous trimethylamine. *Biosens. Bioelectron.* 2015, 71, 179-85.
34. Geertsma, E. R.; Mahmood, N. A. B. N.; Schuurman-Wolters, G. K.; Poolman, B., Membrane reconstitution of ABC transporters and assays of translocator function. *Nature Protocols* 2008, 3 (2), 256-266.
35. Hou, Y. X.; Jaffrezic-Renault, N.; Martelet, C.; Zhang, A. D.; Minic-Vidic, J.; Gorojankina, T.; Persuy, M. A.; Pajot-Augy, E.; Salesse, R.; Akimov, V.; Reggiani, L.; Pennetta, C.; Alfinito, E.; Ruiz, O.; Gomila, G.; Samitier, J.; Errachid, A., A novel detection strategy for odorant molecules based on controlled bioengineering of rat olfactory receptor 17. *Biosens. Bioelectron.* 2007, 22 (7), 1550-1555.
36. Guo, Z.; Zine, N.; Lagarde, F.; Daligault, J.; Persuy, M. A.; Pajot-Augy, E.; Zhang, A.; Jaffrezic-Renault, N., A novel platform based on immobilized histidine tagged olfactory receptors, for the amperometric detection of an odorant molecule characteristic of boar taint. *Food Chem* 2015, 184, 1-6.
37. Jordan, M. D.; Anderson, A.; Begum, D.; Carraher, C.; Authier, A.; Marshall, S. D.; Kiely, A.; Gatehouse, L. N.; Greenwood, D. R.; Christie, D. L.; Kralicek, A. V.; Trowell, S. C.; Newcomb, R. D., Odorant receptors from the light brown apple moth (*Epiphyas postvittana*) recognize important volatile compounds produced by plants. *Chem Senses* 2009, 34 (5), 383-94.
38. Kiely, A.; Authier, A.; Kralicek, A. V.; Warr, C. G.; Newcomb, R. D., Functional analysis of a *Drosophila melanogaster* olfactory receptor expressed in Sf9 cells. *J Neurosci Methods* 2007, 159 (2), 189-94.
39. Claudianos, C.; Lim, J.; Young, M.; Yan, S. Z.; Cristino, A. S.; Newcomb, R. D.; Gunasekaran, N.; Reinhard, J., Odor memories regulate olfactory receptor expression in the sensory periphery. *Eur. J. Neurosci.* 2014, 39 (10), 1642-1654.
40. Forstner, M.; Breer, H.; Krieger, J., A receptor and binding protein interplay in the detection of a distinct pheromone component in the silkmoth *Antheraea polyphemus. Int J Biol Sci* 2009, 5 (7), 745-57.
41. Grosse-Wilde, E.; Gohl, T.; Bouche, E.; Breer, H.; Krieger, J., Candidate pheromone receptors provide the basis for the response of distinct antennal neurons to pheromonal compounds. *Eur. J. Neurosci.* 2007, 25 (8), 2364-73.

42. Grosse-Wilde, E.; Svatos, A.; Krieger, J., A pheromone-binding protein mediates the bombykol-induced activation of a pheromone receptor in vitro. *Chem. Senses* 2006, 31 (6), 547-55.

43. Kumar, B. N.; Taylor, R. W.; Pask, G. M.; Zwiebel, L. J.; Newcomb, R. D.; Christie, D. L., A conserved aspartic acid is important for agonist (VUAA1) and odorant/tuning receptor-dependent activation of the insect odorant co-receptor (Orco). *Plos One* 2013, 8 (7), e70218.

44. Turner, R. M.; Derryberry, S. L.; Kumar, B. N.; Brittain, T.; Zwiebel, L. J.; Newcomb, R. D.; Christie, D. L., Mutational analysis of cysteine residues of the insect odorant co-receptor (Orco) from *Drosophila melanogaster* reveals differential effects on agonist- and odorant-tuning receptor-dependent activation. *J. Biol. Chem.* 2014, 289 (46), 31837-45.

45. Pask, G. M.; Romaine, I. M.; Zwiebel, L. J., The molecular receptive range of a lactone receptor in *Anopheles gambiae*. *Chem. Senses* 2013, 38 (1), 19-25.

46. Liu, C. C.; Liu, Y.; Walker, W. B.; Dong, S. L.; Wang, G. R., Identification and functional characterization of sex pheromone receptors in beet armyworm *Spodoptera exigua* (Hubner). *Insect Biochem. Mol. Biol.* 2013, 43 (8), 747-754.

47. Miura, N.; Nakagawa, T.; Tatsuki, S.; Touhara, K.; Ishikawa, Y., A male-specific odorant receptor conserved through the evolution of sex pheromones in *Ostrinia* moth species. *Int J Biol Sci* 2009, 5 (4), 319-330.

48. Mitsuno, H.; Sakurai, T.; Murai, M.; Yasuda, T.; Kugimiya, S.; Ozawa, R.; Toyohara, H.; Takabayashi, J.; Miyoshi, H.; Nishioka, T., Identification of receptors of main sex-pheromone components of three Lepidopteran species. *Eur. J. Neurosci.* 2008, 28 (5), 893-902.

49. Sakurai, T.; Nakagawa, T.; Mitsuno, H.; Mori, H.; Endo, Y.; Tanoue, S.; Yasukochi, Y.; Touhara, K.; Nishioka, T., Identification and functional characterization of a sex pheromone receptor in the silkmoth *Bombyx mori*. *Proc. Natl. Acad. Sci. U.S.A* 2004, 101 (47), 16653-16658.

50. Xu, P. X.; Garczynski, S. F.; Atungulu, E.; Syed, Z.; Choo, Y. M.; Vidal, D. M.; Zitelli, C. H. L.; Leal, W. S., Moth Sex Pheromone Receptors and Deceitful Parapheromones. *Plos One* 2012, 7 (7).

51. Wang, G.; Vasquez, G. M.; Schal, C.; Zwiebel, L. J.; Gould, F., Functional characterization of pheromone receptors in the tobacco budworm *Heliothis virescens*. *Insect Mol. Biol.* 2011, 20 (1), 125-133.

52. Wanner, K. W.; Nichols, A. S.; Allen, J. E.; Bunger, P. L.; Garczynski, S. F.; Linn, C. E.; Robertson, H. M.; Luetje, C. W., Sex Pheromone Receptor Specificity in the European Corn Borer Moth, *Ostrinia nubilalis*. *Plos One* 2010, 5 (1).

53. Glatz, R.; Bailey-Hill, K., Mimicking nature's noses: from receptor deorphaning to olfactory biosensing. *Prog Neurobiol* 2011, 93 (2), 270-96.

54. Du, L.; Wu, C.; Peng, H.; Zou, L.; Zhao, L.; Huang, L.; Wang, P., Piezoelectric olfactory receptor biosensor prepared by aptamer-assisted immobilization. *Sensors and Actuators B: Chemical* 2013, 187, 481-487.

55. Bayburt, T. H. & Sligar, S. G. Membrane protein assembly into Nanodiscs. *FEBS Lett.* 584, 1721-1727 (2010).

56. Bayburt, T. H. & Sligar, S. G. Self-assembly of single integral membrane proteins into soluble nanoscale phospholipid bilayers. *Protein Sci.* 12, 2476-2481 (2003).

57. Hurot C., Brenet S., Buhot A., Barou E., Belloir C., Briand L., and Hou Y. Highly sensitive olfactory biosensors for the detection of volatile organic compounds by surface plasmon resonance imaging (2019).

The invention claimed is:

1. A sensor device comprising an insect odorant receptor complex, comprising an OrX and an Orco, in electrical communication with a substrate, wherein each of the OrX and the Orco comprise seven transmembrane helices, wherein, when present in a cell membrane, each of the OrX and the Orco have a transmembrane topology having an intracellular N-terminus and an extracellular C-terminus, wherein the insect odorant receptor complex is embedded in a membrane mimic which is coupled to the substrate directly or via a linker molecule, wherein the membrane mimic is selected from a liposome, an amphipol, a detergent micelle, a nanovesicle, a nanodisc, or a surfactant, wherein the sensor device is configured to detect binding of an analyte to the OrX by detecting a change in an electrical characteristic of the substrate, wherein the substrate is selected from: a working electrode of an electrochemical cell, a channel of a carbon nanotube-field effect transistor (CNT-FET), a channel of a graphene-field effect transistor (GFET), a resonator component of a quartz crystal microbalance, or an inert metal surface on a glass prism.

2. The sensor device of claim 1, wherein the insect odorant receptor complex is present in a form that is capable of undergoing a conformational change in response binding of the analyte.

3. The sensor device of claim 1, wherein the membrane mimic is the liposome.

4. The sensor device of claim 1, wherein the membrane mimic comprises amphipathic molecules.

5. The sensor device of claim 1, wherein the sensor device is able to detect the presence of the analyte at a concentration of less than $1 \times 10^{-3}$M.

6. The sensor device of claim 5, wherein the sensor device is able to detect the presence of the analyte at a concentration of less than $1 \times 10^{-12}$M.

7. The sensor device of claim 1, wherein the electrical characteristic is selected from at least one of: conductivity, resistance, complex resistance, impedance, electrochemical impedance, electrochemical potential, flow of current, and resonance frequency of oscillations induced by an alternating electric field.

8. A method of detecting an analyte, the method comprising the steps of:
   a) binding the analyte to the insect OrX in the sensor device of claim 1, and
   b) detecting the change in the electrical characteristic of the substrate, wherein the change in the electrical characteristic of the substrate indicates detection of the analyte.

9. A method of detecting the presence of an analyte in an environment, the method comprising the steps of:
   a) exposing the sensor device of claim 1 to the environment containing the analyte,
   b) binding the analyte to the insect OrX in the sensor device, and
   c) detecting the change in the electrical characteristic of the substrate, wherein the change in the electrical characteristic of the substrate indicates the presence of the analyte in the environment.

10. A method of manufacturing the sensor device of claim 1, the method including the step of establishing the electrical communication between the insect odorant receptor complex, comprising the OrX and the Orco, and the substrate of the sensor device, wherein the sensor device is configured to detect the change in the electrical characteristic of the substrate.

11. A sensor device comprising an insect odorant receptor complex, comprising an OrX and an Orco, in electrical communication with a substrate, wherein each of the OrX and the Orco comprise seven transmembrane helices, wherein, when present in a cell membrane, each of the OrX and the Orco have a transmembrane topology having an intracellular N-terminus and an extracellular C-terminus, wherein the insect odorant receptor complex is embedded in a membrane mimic which is coupled to the substrate directly or via a linker molecule, wherein the membrane mimic is selected from a liposome, an amphipol, a nanovesicle, or a nanodisc, wherein, when the membrane mimic is the liposome, the liposome is not fused with a planar lipid bilayer membrane; wherein the sensor device is configured to detect binding of an analyte to the OrX by detecting a change in an electrical characteristic of the substrate, wherein the substrate is selected from: a working electrode of an electrochemical cell, a channel of a carbon nanotube-field effect transistor (CNT-FET), a channel of a graphene-field effect transistor (GFET), a resonator component of a quartz crystal microbalance, or an inert metal surface on a glass prism.

* * * * *